(12) United States Patent
Singh et al.

(10) Patent No.: US 9,856,474 B2
(45) Date of Patent: Jan. 2, 2018

(54) DEEP INTRONIC TARGET FOR SPLICING CORRECTION ON SPINAL MUSCULAR ATROPHY GENE

(71) Applicant: Iowa State University Research Foundation, Inc., Ames, IA (US)

(72) Inventors: Ravindra N. Singh, Ames, IA (US); Natalia N. Singh, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 60 days.

(21) Appl. No.: 14/647,952

(22) PCT Filed: Jan. 16, 2014

(86) PCT No.: PCT/US2014/011797
§ 371 (c)(1),
(2) Date: May 28, 2015

(87) PCT Pub. No.: WO2014/113540
PCT Pub. Date: Jul. 24, 2014

(65) Prior Publication Data
US 2015/0315582 A1  Nov. 5, 2015

Related U.S. Application Data

(60) Provisional application No. 61/845,521, filed on Jul. 12, 2013, provisional application No. 61/849,833, filed on Jan. 16, 2013.

(51) Int. Cl.
*A61K 48/00* (2006.01)
*C12N 15/11* (2006.01)
(Continued)

(52) U.S. Cl.
CPC ........ *C12N 15/113* (2013.01); *C12N 2310/11* (2013.01); *C12N 2310/113* (2013.01);
(Continued)

(58) Field of Classification Search
USPC ..................... 536/24.5, 23.1, 24.3
See application file for complete search history.

(56) References Cited

U.S. PATENT DOCUMENTS

| 7,176,303 | B2 * | 2/2007 | Freier ................. C07H 21/02 |
| | | | 435/5 |
| 2006/0088873 | A1 * | 4/2006 | Su ...................... C12Q 1/6827 |
| | | | 435/6.11 |
| 2012/0165394 | A1 | 6/2012 | Singh et al. |

FOREIGN PATENT DOCUMENTS

| GB | 2435928 | 9/2007 |
| WO | 2007002390 | 1/2007 |

(Continued)

OTHER PUBLICATIONS

International Bureau, "IPRP", issued in connection to International Application No. PCT/US2014/011797, 9 pages Jul. 30, 2015.
(Continued)

*Primary Examiner* — Terra C Gibbs
(74) *Attorney, Agent, or Firm* — McKee, Voorhees & Sease, PLC

(57) ABSTRACT

The present invention is directed to methods and compositions for blocking the effect of the intronic inhibitory splicing region of intron 7 of the SMN2 gene. The compositions and methods of the instant invention include short oligonucleotide reagents (e.g., oligoribonucleotides) that effectively target sites in the SMN2 pre-mRNA, thereby modulating the splicing of SMN2 pre-mRNA to include exon 7 in the processed transcript. The target regions include a unique RNA structure and a 6-nucleotide long sequence that is essential for initiating a long distance steric inhibitory interaction. The identified region provides a novel target deep within SMN2 intron 7. Intronic targets are highly desirable as annealing of an ASO to an intron does not interfere with translation and transport of mRNA. The
(Continued)

invention also provides opportunity to employ a short antisense oligonucleotide or a small compound against the unique RNA structure responsible of SMN2 exon 7 skipping in SMA.

58 Claims, 34 Drawing Sheets

(51) Int. Cl.
      *C07H 21/02*       (2006.01)
      *C07H 21/04*       (2006.01)
      *C12N 15/113*      (2010.01)

(52) U.S. Cl.
    CPC .. *C12N 2310/314* (2013.01); *C12N 2310/315* (2013.01); *C12N 2310/321* (2013.01); *C12N 2310/3231* (2013.01); *C12N 2310/3233* (2013.01); *C12N 2310/345* (2013.01); *C12N 2310/3521* (2013.01); *C12N 2320/33* (2013.01)

(56) References Cited

FOREIGN PATENT DOCUMENTS

| WO | 2010148249 | 12/2010 |
|---|---|---|
| WO | 2012170725 | 12/2012 |
| WO | 2012170725 A2 | 12/2012 |

OTHER PUBLICATIONS

Singh, Natalia N. et al., "An intronic structure enabled by a long-distance interaction serves as a novel target for splicing correction in spinal muscular atrophy" Nucleic Acids Research, vol. 41, No. 17 pp. 8144-8165, Jul. 16, 2013.

International Searching Authority, "The International Search Report and The Written Opinion of the International Searching Authority" issued in connection with PCT/US2014/011797, dated Apr. 11, 2014.

Lawler et al., "A Unique Long-Distance Interaction in Pre-mRNA Splicing," Department of Biomedical Sciences, Iowa State University, Sep. 2010, 1 page.

Singh et al., "A Deep Intronic Target for Splicing Correction in Spinal Muscular Atrophy Gene," Department of Biomedical Sciences, Iowa State University, Nov. 20, 2012, 28 pages.

Singh et al., "A Deep Intronic Target for Splicing Correction in Spinal Muscular Atrophy Gene," Department of Biomedical Sciences, Iowa State University, Nov. 26, 2012, 29 pages.

Singh et al., "An Antisense Oligonucleotide Uncovers the Critical Role of an Intronic Position within a Therapeutic Target of Spinal Muscular Atrophy," Department of Biomedical Sciences, Iowa State University, Oct. 2011, 1 page.

Singh et al., "An Antisense Oligonucleotide Uncovers the Critical Role of an Intronic Position within a Therapeutic Target of Spinal Muscular Atrophy," Department of Biomedical Sciences, Iowa State University, Oct. 2012, 1 page.

Singh et al., "Position-Specific Impact of Small RNAs on Alternative Pre-mRNA Splicing," Department of Biomedical Sciences, Iowa State University, Dec. 2012, 1 page.

Singh et al., "Role of a Unique RNA-RNA Long Distance Interaction in Spinal Muscular Atrophy," Department of Biomedical Sciences, Jun. 2012, 1 page.

\* cited by examiner

DEEP INTRONIC TARGET FOR SPLICING CORRECTION ON SPINAL MUSCULAR ATROPHY GENE

CROSS-REFERENCE TO RELATED APPLICATIONS

This is a National Phase application claiming priority to PCT/US2014/11797 filed Jan. 16, 2014 which claims priority under 35 U.S.C. §119 to provisional applications U.S. Ser. No. 61/845,521 filed Jul. 12, 2013 and Ser. No. 61/849,883 filed Jan. 16, 2013, all of which are herein incorporated by reference in their entireties.

GRANT REFERENCE

This invention was made with government support under NIH Grant No. NS055925 awarded by the United States National Institutes of Health. The government has certain rights in the invention.

BACKGROUND OF THE INVENTION

Alternative splicing increases the coding potential of human genome by producing multiple proteins from a single gene (Black, D. L. 2003. Annu. Rev. Biochem. 72:291-336). It is also associated with a growing number of human diseases (Faustino, N. A., and T. A. Cooper. 2003. Genes Dev. 17:419-437; Garcia-Blanco, M. A., et al. 2004. Nat. Biotechnol. 22:535-546; Pagani, F., and F. E. Baralle. 2004. Nat. Rev. Genet. 5:389-396).

Spinal Muscular Atrophy (SMA) is an often-fatal genetic disorder resulting from the loss of the Survival Motor Neuron (SMN) protein encoded by the Survival Motor Neuron (SMN) gene. The SMN genes, SMN1 and SMN2, are located on chromosome 5 and SMA is caused by the loss of SMN1 from both chromosomes. SMN2, while being almost identical to SMN1, is less effective at making the SMN protein. The severity of SMA is affected by the efficiency at which SMN2, of which there are several copies, produces the SMN protein.

SMN1 encodes a ubiquitously expressed 38 kDa SMN protein that is necessary for snRNP assembly, an essential process for cell survival (Wan, L., et al. 2005. Mol. Cell. Biol. 25:5543-5551). A nearly identical copy of the gene, SMN2, fails to compensate for the loss of SMN1 because of exon 7 skipping, producing an unstable truncated protein, SMNΔ7 (Lorson, C. L., et al. 1998. Nat. Genet. 19:63-66). SMN1 and SMN2 differ by a critical C to T substitution at position 6 of exon 7 (C6U in transcript of SMN2) (Lorson, C. L., et al. 1999. Proc. Natl. Acad. Sci. USA 96:6307-6311; Monani, U. R., et al. 1999. Hum. Mol. Genet. 8:1177-1183). C6U does not change the coding sequence, but is sufficient to cause exon 7 skipping in SMN2.

Current treatment for SMA of prevention and management of the secondary effect of chronic motor unit loss. Currently, there are no drug therapies available for the treatment or prevention of SMA.

Antisense oligonucleotide (ASO) or antisense oligonucleotide analog (AON analog)-based technology, used mostly for RNA down regulation, recently has been adapted to alter the splicing process (Kole et al., Acta Biochim Pol. (2004) 51, 373-8). Techniques that trick the splicing machinery to alter splicing of SMN2 pre-mRNAs are likely to have high therapeutic value.

SUMMARY OF THE INVENTION

The present invention is based, in part, on the discovery that antisense targeting, blocking and/or sequestration of an intronic sequence in the SMN2 gene can enhance production of full-length SMN2 transcripts (exon 7-containing transcripts) upon splicing. In particular, the present inventors have identified a critical SMN2 intron 7 region that harbors a 23-nucleotide (23-nt) inhibitory sequence as the desirable therapeutic target. Accordingly, the invention is directed to effective use of blocking agents targeting this 23-nt inhibitory sequence that is termed as Intronic Splicing Silencer N2 or ISS-N2 (SEQ ID NO: 12).

An efficient removal of SMN2 intron 7 by splicing is critical to generate the full-length messenger RNA (mRNA) and consequently the full-length SMN protein to ameliorate the symptoms of SMA. Applicants have previously identified a single critical base, $^{10}$C which must be targeted and which interacts with distant sequences in a steric fashion to inhibit SMN2 intron 7 splicing. See United States Published Application 2011/0269820 filed Apr. 26, 2011 the disclosure of which is herein incorporated by reference in its entirety. Applicants had found that this critical base, and sequences 5' thereof, which did not include any previously known target motifs worked better than any targets discovered to date, and created the opportunity to generate sequences as short as 5-mers that were effective in repairing splicing.

Applicants have now identified that the $^{10}$C mediated long-distance interaction (LDI) is linked to ISS-N2 that is located in the second half of intron 7. Residues of ISS-N2 (SEQ ID NO: 12) are predicted to form Internal Stems Through LDIs (ISTLs). Applicants define ISTLs as RNA:RNA duplex structures formed by continuous base-pairing of 7 or more residues of complementary RNA strands that are separated from each other by more than 80 nucleotides. There are three ISTLs within intron 7: ISTL1, ISTL2 and ISTL3. Notably, ISS-N2 incorporates the 3' strands of ISTL1, ISTL2 and ISTL3. Thus, ISS-N2 provides the basis of a very complex and unique structure comprised of three juxtaposed RNA helices. In particular, applicants have now identified the critical LDI site-1 (LS-1) GCAGAC which is positioned in the 3'-strand of ISTL1 GCAGACUU. ISTL1 is formed by intronic sequences separated from each other by more than 280 nucleotides away. An antisense oligonucleotide (ASO)-mediated blocking of LS-1 and flanking intronic sequences within ISS-N2 fully corrected the SMN2 exon 7 splicing and restored high levels of SMN protein in SMA patient cells. Applicants have also demonstrated this in a mouse model of SMA. The invention thus includes, blocking oligonucleotide reagents (e.g., modified antisense oligonucleotide analogs) to inhibit these critical LDI target sequences. Treatment of cells derived from SMA patients with the oligonucleotide reagent compositions of the instant invention will effectively restore the production of the full-length SMN protein. These results demonstrate the ability of an oligonucleotide reagent to suppress the negative effect of a deep intronic silencer (ISS-N2) and/or associated inhibitory RNA structures (ISTL1, ISTL2, ISTL3). The deep intronic silencer also provides a novel target site for inhibition of the intron 7 aberrant splicing and includes oligonucleotides designed to block a $^{10}$C interacting companion region of intron 7: a six nucleotide target sequence (LS-1) in the second half of intron 7.

The present invention therefore is directed to compositions capable of blocking the inhibitory effects of the newly-discovered SMN2 long distance interaction site. Agents capable of blocking the inhibitory effect of ISS-N2 including LS-1 have high value as SMA therapeutics. Featured agents capable of blocking the splice-inhibitory effect of the SMN2 long distance interaction site include, but are not limited to, e.g., agents that disrupt the interaction of a target domain-interacting protein with the target sequence, agents that sequester a target interacting protein, agents that disrupt the structure of the target domain (ISSN-2 (SEQ ID NOs: 12), ISTL1 (GCAGACUU), ISTL2 (CAGACCA) and ISTL3 (CUAGUAGG)) and/or surrounding regions.

In exemplary embodiments, the instant invention is directed to oligonucleotide reagents (e.g., antisense oligonucleotide analogs) that block the effect on pre-mRNA splicing of the SMN2 sequence via direct interaction and/or hybridization with the target sequence. Such RNA-complementary oligonucleotide reagents may be modified by art-recognized means to improve their in vivo stabilities and/or bioaccessibility. The instant invention is also directed to methods for identifying target domain-interacting proteins, as such methods are enabled by discovery and characterization of the target sequence.

In one aspect, the instant invention is directed to an isolated oligonucleotide reagent (e.g., an antisense oligonucleotide analog) typically of from bout 15 to about 40 nucleotides in length, comprising a nucleotide sequence which is complementary to ISS-N2 or its components including LS-1 and the 3' strands of ISTL1, ISTL2 and ISTL3.

In another aspect, the instant invention is directed to an isolated oligonucleotide reagent (e.g., an antisense oligonucleotide analog) which targets a six nucleotide sequence motif (GCAGAC) from $290^{th}$ to $295^{th}$ positions of intron 7. Termed herein as the LDI site-1 or LS-1.

In an additional aspect, the instant invention is directed to an isolated oligonucleotide reagent (e.g., an antisense oligonucleotide analog) which is complementary to the 6-mer sequence 5'-GCAGAC-3'.

In a further aspect, the instant invention is directed to an isolated oligonucleotide reagent (e.g., an antisense oligonucleotide analog) which is complementary to the 3'-strand of ISTL1, a sequence which includes residues from $290^{th}$-$297^{th}$ positions of intron 7.

In another aspect, the instant invention is directed to an antisense oligonucleotide analog (AON analog) AON reagent (e.g., an antisense oligonucleotide analog) which is greater than 90% complementary to the sequence 5'-CUAGUAGGCAGACCAGCAGACUU-3 (SEQ ID NO:12).

Applicants have demonstrated that the 6-mer target (LS-1) is present in a 23-nt long inhibitory region (ISS-N2) that spans from the $275^{th}$ to $297^{th}$ positions of intron 7.

In a further aspect, the instant invention is directed to an isolated oligonucleotide reagent of 15 to 40 nucleotides (e.g., an antisense oligonucleotide analog) which is complementary to a sequence which includes the sequences from $290^{th}$-$295^{th}$ positions of intron 7 GCAGAC as well as additional consecutive 5' or 3' sequences from the $271^{th}$ to $310^{th}$ position so that the oligonucleotide specifically targets the $290^{th}$ to $295^{th}$ bases.

In an additional aspect, the instant invention is directed to an isolated oligonucleotide reagent comprising the sequence 5'-GUCUGC-3' and which targets positions 290-295 of intron 7 of SMN2.

In another aspect, the instant invention is directed to an isolated oligonucleotide reagent comprising a sequence greater than 80% identical to GUCUGC which targets positions 290-295 of intron 7 of SMN2.

In another aspect, the instant invention is directed an isolated oligonucleotide reagent of 7-5-bases comprising GUCUGC and additional sequence 5' or 3' thereof so that said oligonucleotide targets the $290^{th}$-$295^{th}$ bases of intron 7 of SMN2.

In another aspect the instant invention is directed an isolated oligonucleotide reagent which is complementary to a sequence which includes bases from $275^{st}$ to $297^{th}$ positions of intron 7.

In an additional aspect, the instant invention is directed to an isolated oligonucleotide typically from about 15 to about 40 bases in length, comprising the sequence 5'-GUCUGC-3' and which targets positions 290-295 of intron 7 of SMN2 and includes SEQ ID NO:4, 5, 6, 7, 8 or 13.

In another aspect, the instant invention is directed to an oligonucleotide reagent comprising a sequence greater than 80% identical to SEQ ID NO: 4, 5, 6, 7, 8 or 13 which targets ISS-N2 of intron 7 of SMN2.

In yet another aspect, the invention is directed to an antisense oligonucleotide analog of 15 to 40 bases of SEQ ID NO: 4, 5, 6, 7, 8, or 13 wherein uracil bases are optionally thymine bases.

In yet another aspect, the invention includes an antisense oligonucleotide analog of 15-40 nucleotides in length of SEQ ID NO:6.

As described in the examples, an antisense oligonucleotide "ASO 283-297" (SEQ ID NO: 6), which sequestered the entire 3' strands of ISTL1 and ISTL2, was shown to be the most effective antisense oligonucleotide, whose stimulatory effect was comparable to that of a known antisense compound, F14, which targets ISS-N1 (see FIG. 11A, lanes 6 and 11). This antisense oligonucleotide was also shown to effectively stimulate SMN2 exon 7 inclusion and up-regulate SMN protein levels in SMA patient cells (see FIG. 11B). A noticeable increase in the level of SMN-interacting protein Gemin2 was also seen (FIG. 11B, left panel). The stimulatory effect of ASO 283-297 on SMN2 exon 7 splicing and levels of SMN and Gemin2 was comparable to that of Anti-N1, a 20-mer ASO that targets ISS-N1 (FIG. 11B). Taken together, these results represent the first example in which an antisense oligonucleotide annealing to a deep intronic sequence corrects aberrant splicing and restores high levels of a full-length protein in a cell-based model of a genetic disease.

Accordingly, another aspect of the invention is directed to an antisense oligonucleotide analog of 15 to 40 nucleotides in length comprising a nucleotide sequence which is complementary to and which targets nucleotides 283-297 of intron 7 of the SMN2 gene. In one embodiment, the antisense oligonucleotide analog is 15-40 bases and comprises at least 6, 7, 8, 9, 10, 11, 12, 13, 14 or 15 contiguous bases of SEQ ID NO: 6. In another embodiment, the antisense oligonucleotide analog is 20 to 25 bases and includes SEQ ID NO: 6. In yet another embodiment, the antisense oligonucleotide analog is 15 to 40 bases and comprises a sequence set forth in SEQ ID NO:6, wherein uracil bases are optionally thymine bases. In another embodiment, the antisense oligonucleotide analog is a morpholino oligomer of 15 to 40 bases and comprises a sequence set forth in SEQ ID NO:6, wherein uracil bases are thymine.

Another aspect of the invention is directed to an antisense oligonucleotide analog of 15 to 40 nucleotides in length comprising a nucleotide sequence which is complementary to and which targets nucleotides 281-295 of intron 7 of the SMN2 gene. In one embodiment, the antisense oligonucleotide analog is 15-40 bases and comprises at least 6, 7, 8, 9, 10, 11, 12, 13, 14, or 15 contiguous bases of SEQ ID NO: 5. In another embodiment, the antisense oligonucleotide analog is 20 to 25 bases and includes SEQ ID NO: 5. In yet another embodiment, the antisense oligonucleotide analog is 15 to 40 bases and comprises a sequence set forth in SEQ ID NO:6, wherein uracil bases are optionally thymine bases. In another embodiment, the antisense oligonucleotide analog is a morpholino oligomer of 15 to 40 bases and comprises a sequence set forth in SEQ ID NO: 5, wherein uracil bases are thymine.

In yet another aspect, the invention is directed to an antisense oligonucleotide analog of 15 to 40 nucleotides in length comprising a nucleotide sequence which is complementary to and which targets nucleotides 275-297 of intron 7 of the SMN2 gene. In one embodiment, the antisense oligonucleotide analog is 15-40 bases and comprises at least 6, 7, 8, 9, 10, 11, 12, 13, 14, 15, 16, 17, 18, 19, 20, 21, 22 or 23 contiguous bases of SEQ ID NO: 13. In another embodiment, the antisense oligonucleotide analog is 20 to 25 bases and includes SEQ ID NO: 13. In yet another embodiment, the antisense oligonucleotide analog is 15 to 40 bases and comprises at least 10 bases of the nucleotide sequence set forth in SEQ ID NO: 13, wherein uracil bases are optionally thymine bases. In another embodiment, the antisense oligonucleotide analog is a morpholino oligomer of 15 to 40 bases and comprises at least 10 bases of the nucleotide sequence set forth in SEQ ID NO: 13, wherein uracil bases are thymine.

In one embodiment, the oligonucleotide is modified by the substitution of at least one nucleotide with a modified nucleotide, such that in vivo stability is enhanced as compared to a corresponding unmodified oligonucleotide. In a related embodiment, the modified nucleotide is a sugar-modified nucleotide. In another embodiment, the modified nucleotide is a nucleobase-modified nucleotide.

In an additional embodiment, the modified nucleotide is a 2'-deoxy ribonucleotide. In certain embodiments, the 2'-deoxy ribonucleotide is 2'-deoxy adenosine or 2'-deoxy guanosine. In another embodiment, the modified nucleotide is a 2'-O-methyl (e.g., 2'-O-methylcytidine, 2'-O-methylpseudouridine, 2'-O-methylguanosine, 2'-O-methyluridine, 2'-O-methyladenosine, 2'-O-methyl) ribonucleotide. In another embodiment, the modified nucleotide is 2'-O-(2-methoxyethyl) or MOE moiety (e.g. MOE thymidine, MOE uridine, MOE cytidine, MOE adenosine, and MOE guanosine) (Geary et al., 2001, J Pharmacology Experimental Therapy, 296:890-897). In an additional embodiment, the modified nucleotide is selected from the group consisting of a 2'-fluoro, 2'-amino and 2'-thio modified ribonucleotide. In a further embodiment, the modified nucleotide is selected from the group consisting of 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine and 2'-amino-butyryl-pyrene-uridine. In an additional embodiment, the modified nucleotide is selected from the group consisting of 5-bromo-uridine, 5-iodo-uridine, 5-methyl-cytidine, ribo-thymidine, 2-aminopurine, 5-fluoro-cytidine, and 5-fluoro-uridine, 2,6-diaminopurine, 4-thio-uridine, and 5-amino-allyl-uridine. In an another embodiment, the modified nucleotide is selected from the group consisting of 2'-O-(2-methoxyethyl) thymidine, 2'-O-(2-methoxyethyl) uridine, 2'-O-(2-methoxyethyl) cytidine, 2'-O-(2-methoxyethyl) adenosine, and 2'-O-(2-methoxyethyl) guanosine (Geary et al., 2001, J Pharmacology Experimental Therapy, 296:890-897).

In a further embodiment, the modified nucleotide is a backbone-modified nucleotide. In one embodiment the modification includes a morpholino group. In another embodiment, the backbone-modified nucleotide contains a phosphorothioate group. In another embodiment, the modified nucleotide is a locked nucleic acid (LNA).

Another embodiment is directed to a composition comprising an oligonucleotide of the invention. In certain embodiments, the composition further comprises a pharmaceutical carrier.

An additional embodiment of the invention is directed to a method of enhancing the level of exon 7-containing SMN2 mRNA relative to exon 7-deleted SMN2 mRNA in a cell or cell extract, comprising contacting the cell or cell extract with an oligonucleotide (e.g., an antisense oligonucleotide analog) of the invention, such that the level of exon 7-containing SMN2 mRNA relative to exon-deleted SMN2 mRNA in the cell or cell extract is enhanced. In one embodiment, the cell or cell extract is a spinal muscular atrophy (SMA) patient-derived neuronal cell, muscle cell or fibroblast, or extract thereof. In certain embodiments, the cell or cell extract is selected from the group consisting of an embryonic stem cell, an embryonic stem cell extract, a neuronal stem cell and a neuronal stem cell extract.

A related embodiment of the invention is directed to a method of enhancing the level of exon 7-containing SMN2 mRNA relative to exon 7-deleted SMN2 mRNA in an organism, comprising administering to the organism an oligonucleotide of the invention (e.g., an antisense oligonucleotide analog), such that the level of exon 7-containing SMN2 mRNA relative to exon 7-deleted SMN2 mRNA in the organism is enhanced. In one embodiment, the organism is a mammal. In another embodiment, the organism is a human. In certain embodiments, the human has spinal muscular atrophy (SMA).

Another embodiment of the invention is directed to a method of treating spinal muscular atrophy (SMA) in a patient, comprising administering to the patient an oligonucleotide of the invention (e.g., an antisense oligonucleotide analog) in a dose effective to enhance the level of exon 7-containing SMN2 mRNA relative to exon-deleted SMN2 mRNA in cells of the patient, such that SMA in the patient is treated.

A further embodiment is directed to a method for inhibiting an SMN2 pre-mRNA intronic splicing silencer site in a cell or cell extract comprising contacting the cell with an oligonucleotide of the invention (e.g., an antisense oligonucleotide analog), such that the SMN2 intronic splicing silencer site is inhibited. In a related embodiment, the instant invention is directed to a method for inhibiting an SMN2 pre-mRNA intronic splicing silencer site in an organism comprising administering to the organism an oligonucleotide of the invention, such that the SMN2 intronic splicing silencer site is inhibited. Another embodiment is directed to a method for inhibiting an SMN2 pre-mRNA intronic splicing silencer site in a subject with SMA comprising administering to the subject an oligonucleotide of the invention (e.g., an antisense oligonucleotide analog), such that the SMN2 intronic splicing silencer site is inhibited.

An additional aspect of the invention is directed to a method for identifying a protein that interacts with ISTL1, ISTL2 and ISTL3 structure as well as sequences set forth as herein, SEQ ID NOS:1, (GCAGAC), 14, (GCAGACUU), (CAGACCA), (CUAGUAGG), comprising contacting a cell or cell extract with the sequence under conditions sufficient for the sequence to interact with a protein in the cell or cell extract; and isolating the sequence and interacting protein, such that the protein that interacts with the target sequence is identified. In one embodiment, the method further comprises UV-crosslinking the sequence to the interacting protein. In an additional embodiment, the cell or cell extract is of mammalian origin. In certain embodiments, the cell or cell extract is of human origin.

Another aspect of the invention is directed to a method of enhancing the level of exon 7-containing SMN2 mRNA relative to exon 7-deleted SMN2 mRNA in a cell or cell extract, comprising contacting the cell or cell extract with an oligonucleotide or nucleotide targeted blocking agent of the invention, such that the level of exon 7-containing SMN2 mRNA relative to exon-deleted SMN2 mRNA in the cell or cell extract is enhanced. A related aspect of the invention is directed to a method of enhancing the level of exon 7-containing SMN2 mRNA relative to exon-deleted SMN2 mRNA in an organism, comprising contacting the organism with an oligonucleotide SNM2 blocking agent, such that the level of exon 7-containing SMN2 mRNA relative to exon-deleted SMN2 mRNA in the organism is enhanced.

In one embodiment, the blocking agent is selected from the group consisting of a small molecule, a peptide, a polynucleotide, an antibody or biologically active portion thereof, a peptidomimetic, and a non-peptide oligomer. In an additional embodiment, the blocking agent is a small molecule.

In an additional aspect, the invention is directed to a method of treating amyotrophic lateral sclerosis (ALS) in a patient, comprising administering to the patient the oligonucleotide of the invention in a dose effective to enhance the level of exon 7-containing SMN2 mRNA relative to exon 7-deleted SMN2 mRNA in cells of the patient.

In an additional embodiment, the oligonucleotide reagent of the invention is a ribozyme.

Other features and advantages of the invention will be apparent from the following detailed description and claims.

BRIEF DESCRIPTION OF THE DRAWINGS

References in the figures all are made with reference to SEQ ID NO: 14, the intron 7 sequence.

Figure 6A:
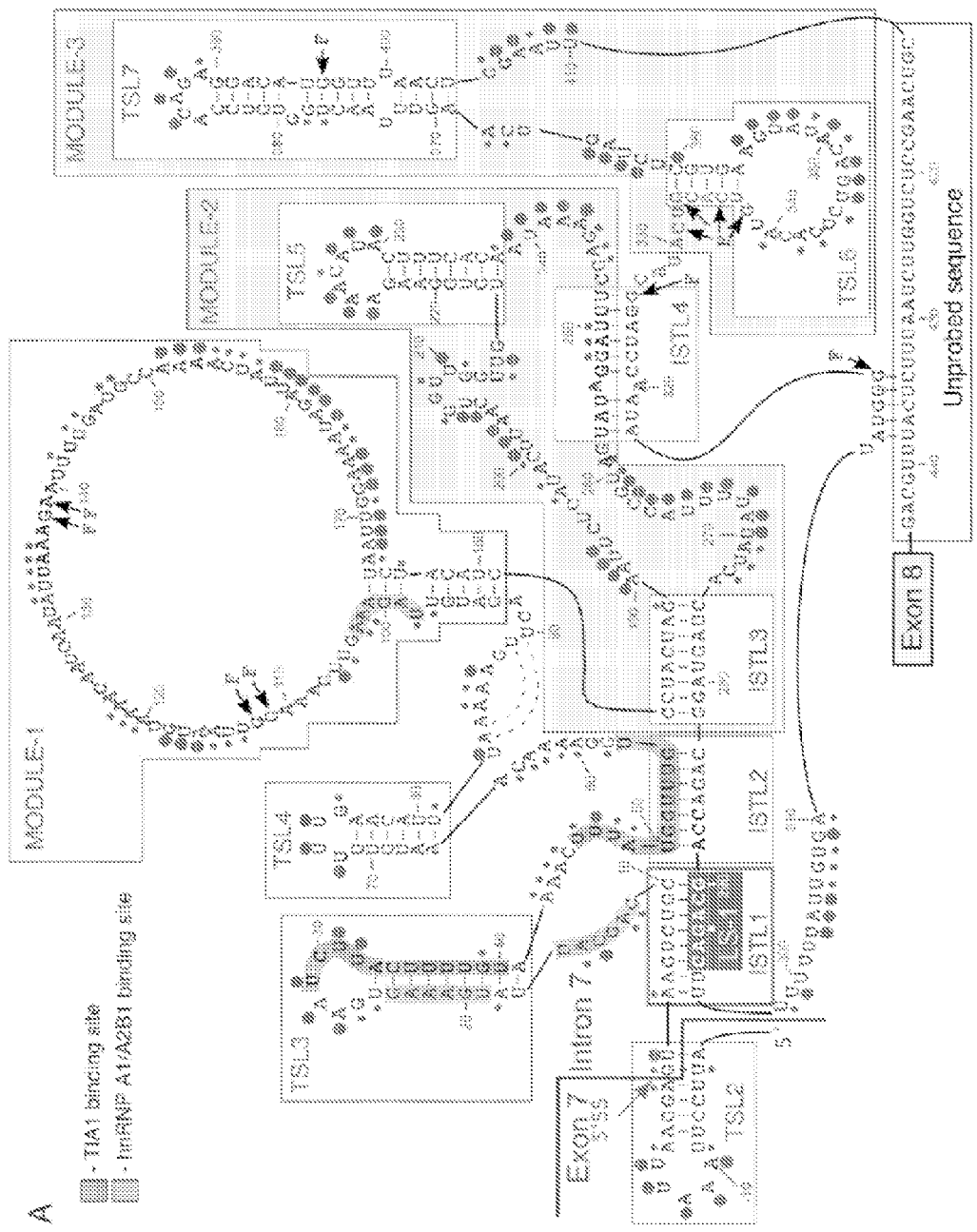
Figure 6B:
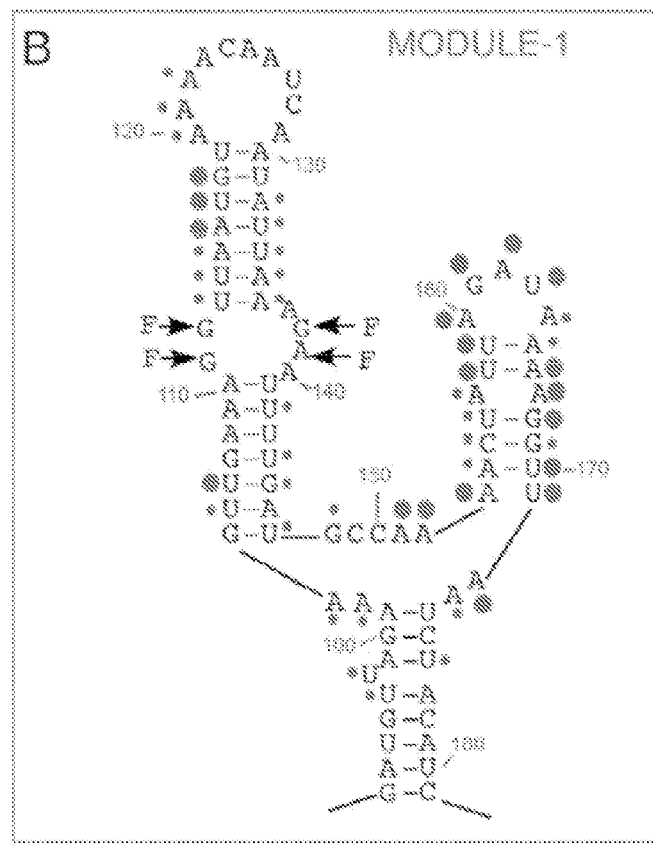
Figure 6C:
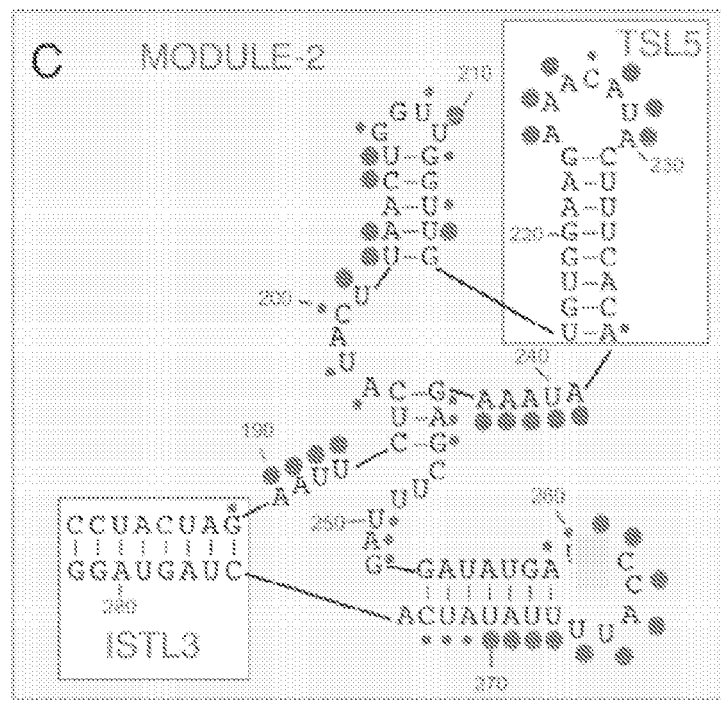

FIG. 6A-6C show the secondary structure of SMN2 intron 7. (A) SHAPE-derived structure of SMN2 intron 7 (SEQ ID NO: 101). This structure is based on combined results produced with ten extension primers (Table 4). Large circles indicate nucleotides with normalized 1M7 reactivity >0.5, small circles indicate nucleotides with normalized 1M7 reactivity between 0.3 and 0.5. Locations of modules, ISTLs and TSLs have been indicated. Positions corresponding to RTase falloffs are marked with "F". Nucleotides marked in gray (numbered 326 to 338) constitute a region with unconfirmed structure due to multiple falloffs. Alternative secondary structures of Module 1 (B) (SEQ ID NO: 102) and Module 2 (C) (SEQ ID NO: 103) as predicted by mfold. Descriptions of abbreviations are given in the main body of the text as well as in the Table 1.

Figure 7A:
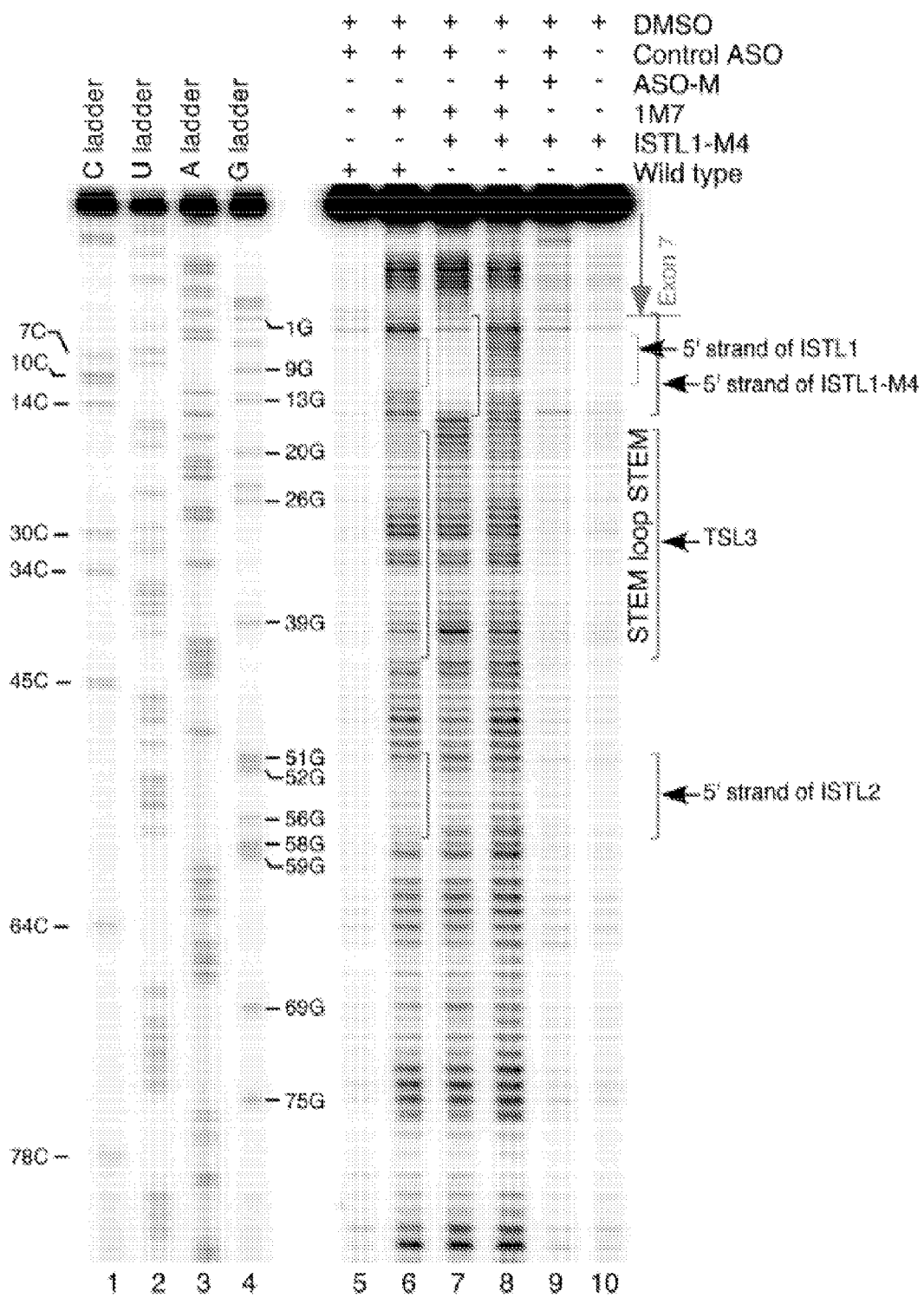
Figure 7B:
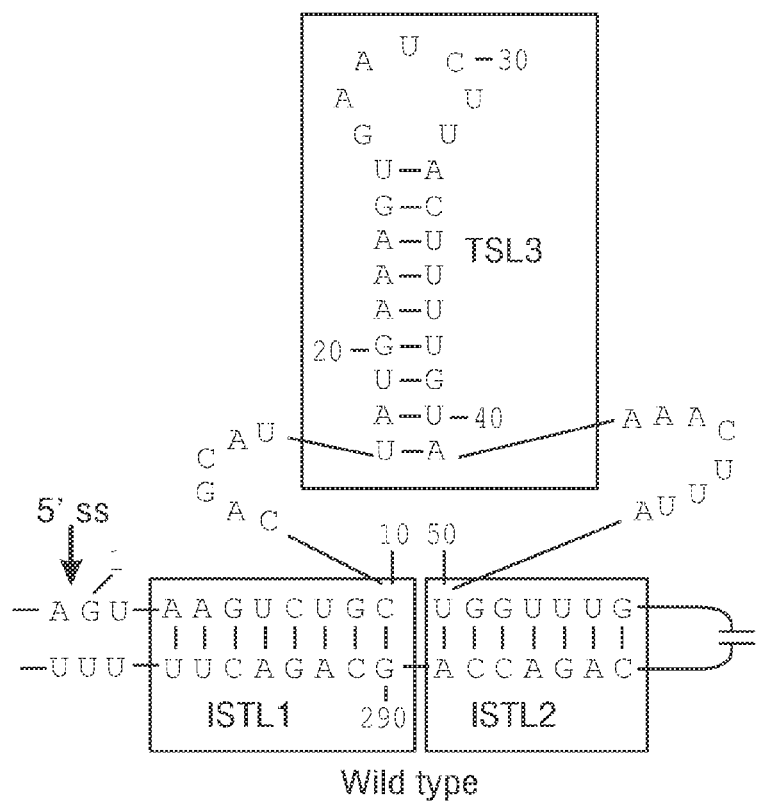
Figure 7B:
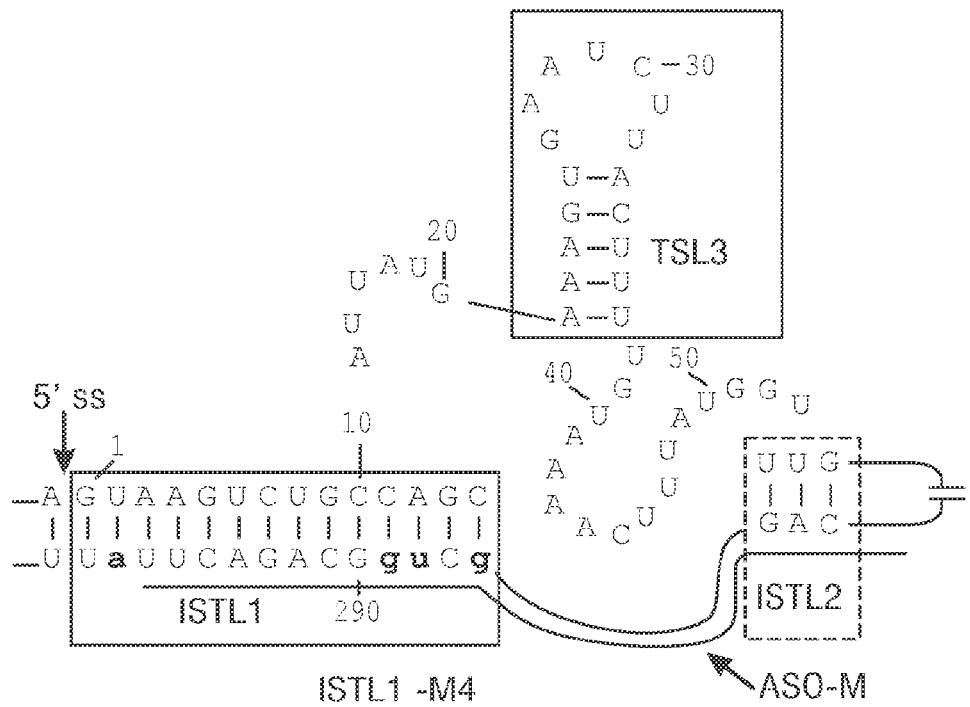
Figure 7C:
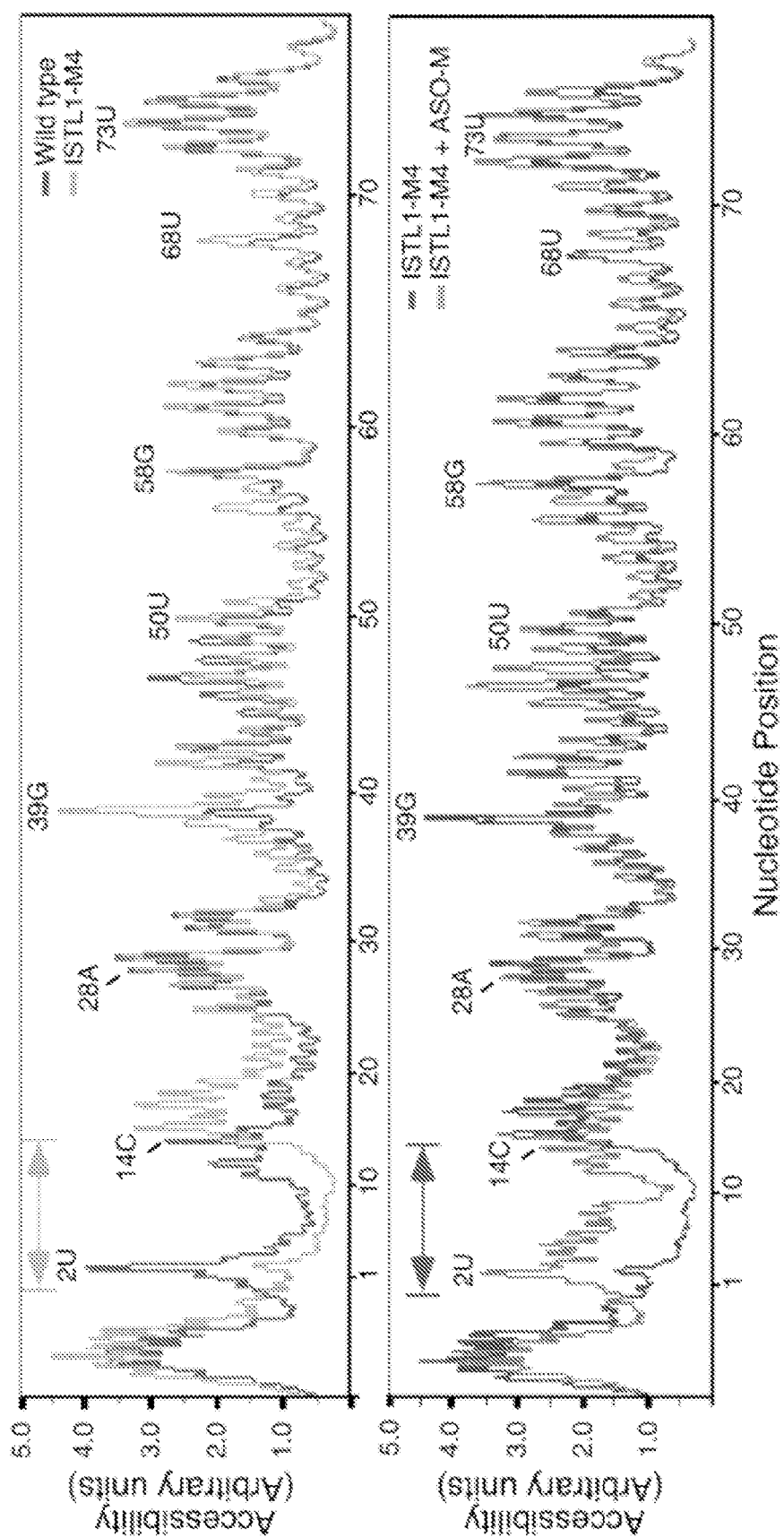

FIG. 7A-7C show the validation of the engagement of the 5' strand of ISTL1 in structure formation. (A) SHAPE results for the 5' portion of intron 7 of the wild type and ISTL1-M4 mutant RNAs generated using Primer#10. Based on the sequencing ladders, positions of residues and locations of structures are marked on the gel. (B) Abridged mfold predicted structure of SMN2 intron 7 (SEQ ID NOs: 47, 90, 104). The probed structure is in agreement with the mfold predicted structure. Nucleotide substitutions are shown in small-case letters. Annealing site of ASO-M is indicated. Abbreviations are the same as in FIG. 6. (C) Alignment of raw peak profiles for the wild type and mutant RNAs. Nucleotides that constitute the 5' strand of ISTL1 in the mutant RNA are marked. Peak profiles were generated using MultiGauge Software version 3.0 (FujiFilm).

Figure 8A:
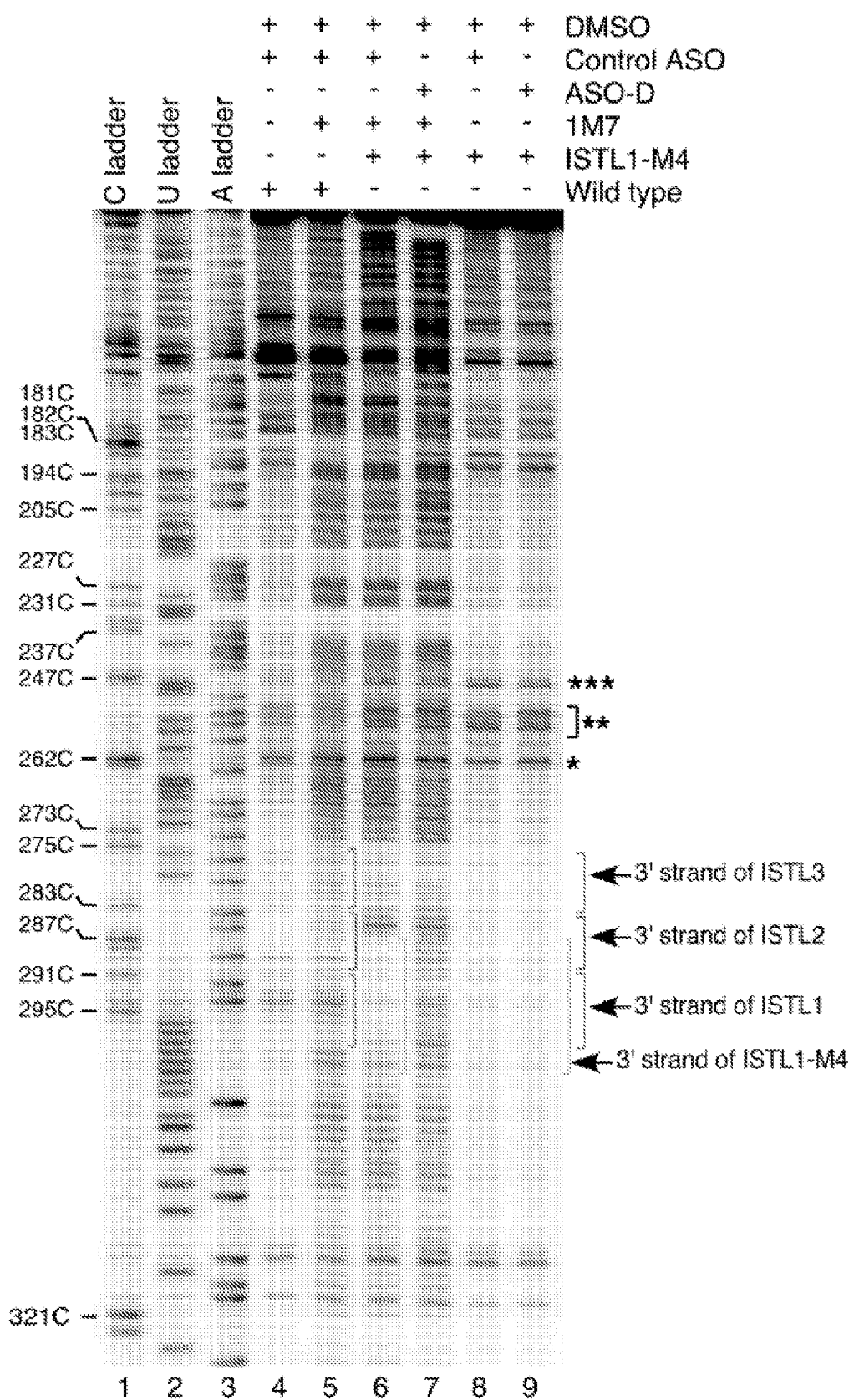
Figure 8B:
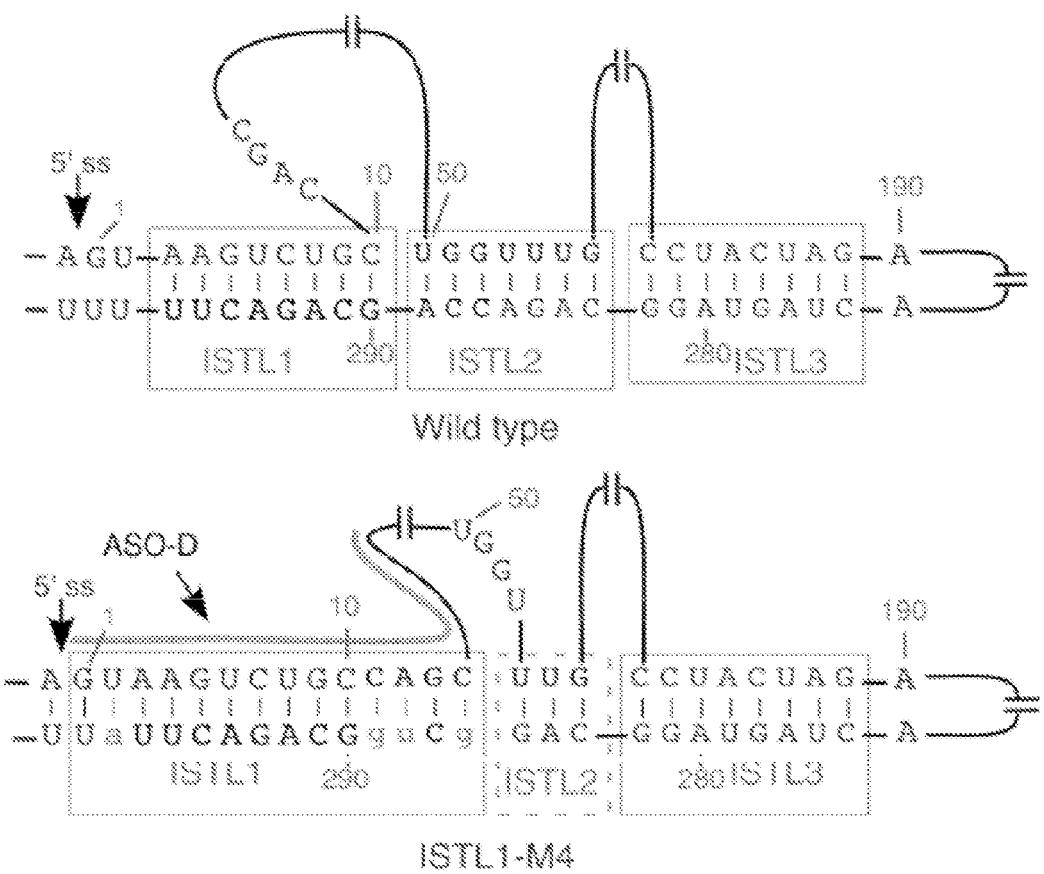
Figure 8C:
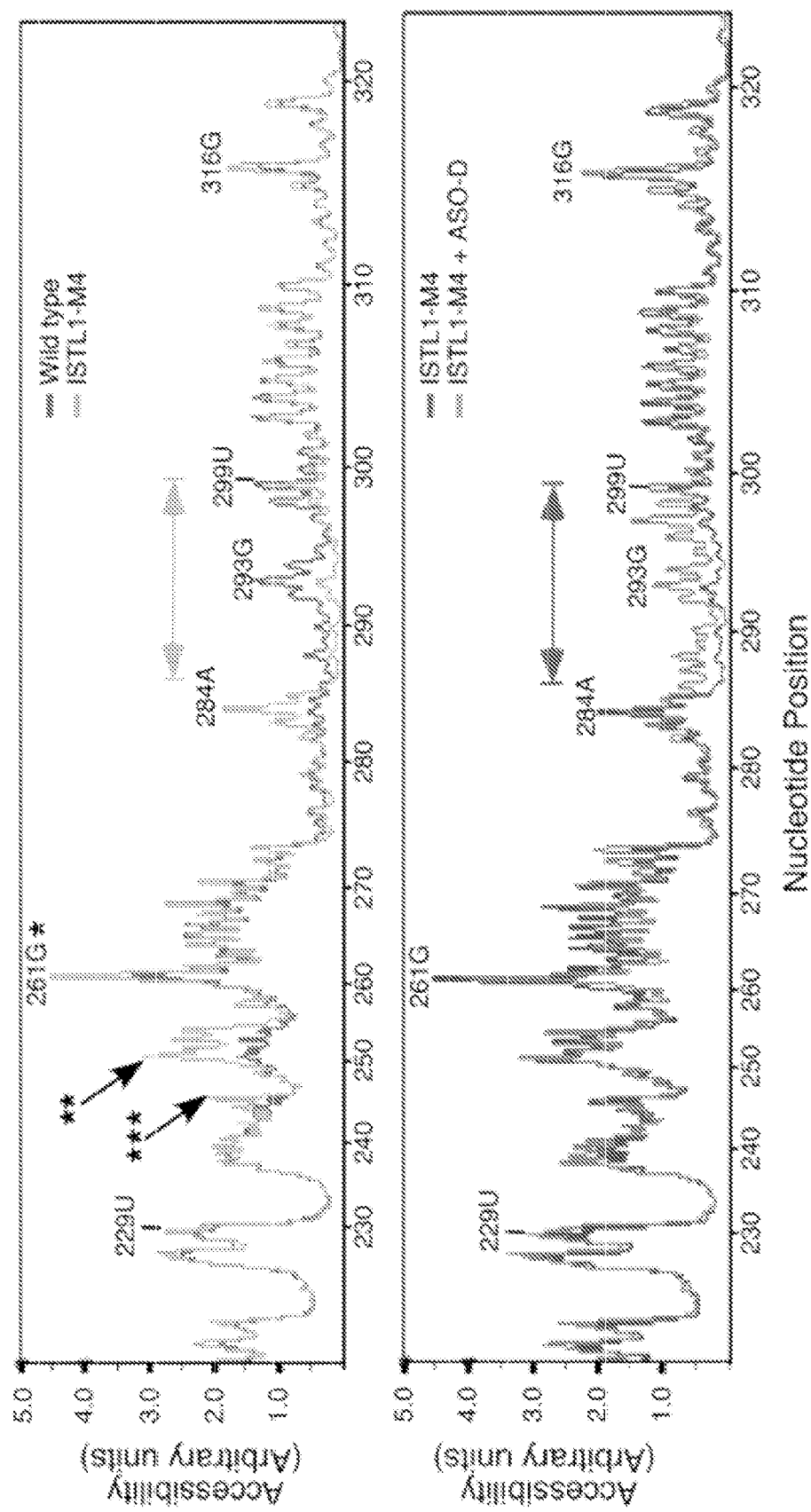

FIG. 8A-8C show the validation of the engagement of the 3' strand of ISTL1 in structure formation. (A) SHAPE results for the middle portion of intron 7 of the wild type and ISTL1-M4 mutant RNA generated using Primer#17. Based on the sequencing ladders, positions of residues and locations of structures are marked on the gel. (B) Abridged mfold predicted structure of SMN2 intron 7 (SEQ ID NOs: 105-107). The probed structure is in agreement with the mfold predicted structure. Nucleotide substitutions are shown in small-case letters. Annealing site of ASO-D is indicated. (C) Alignment of raw peak profiles of the wild type and mutant RNAs. Nucleotides that constitute the 3' strand of ISTL1 in the mutant RNA are marked. Peak profiles were generated using MultiGauge Software version 3.0 (FujiFilm). RTase falloff products are marked by stars.

Figure 9A:
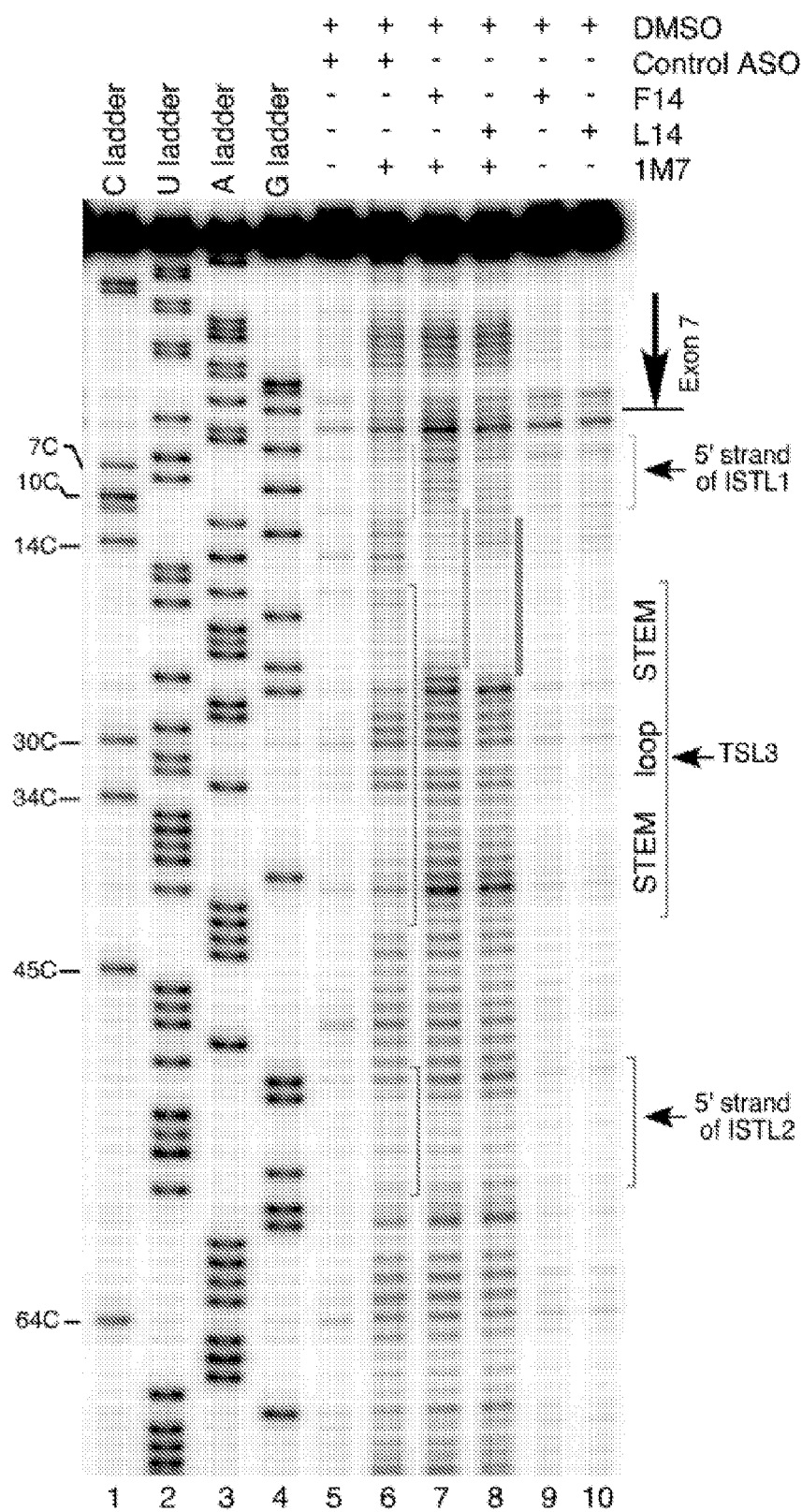
Figure 9B:
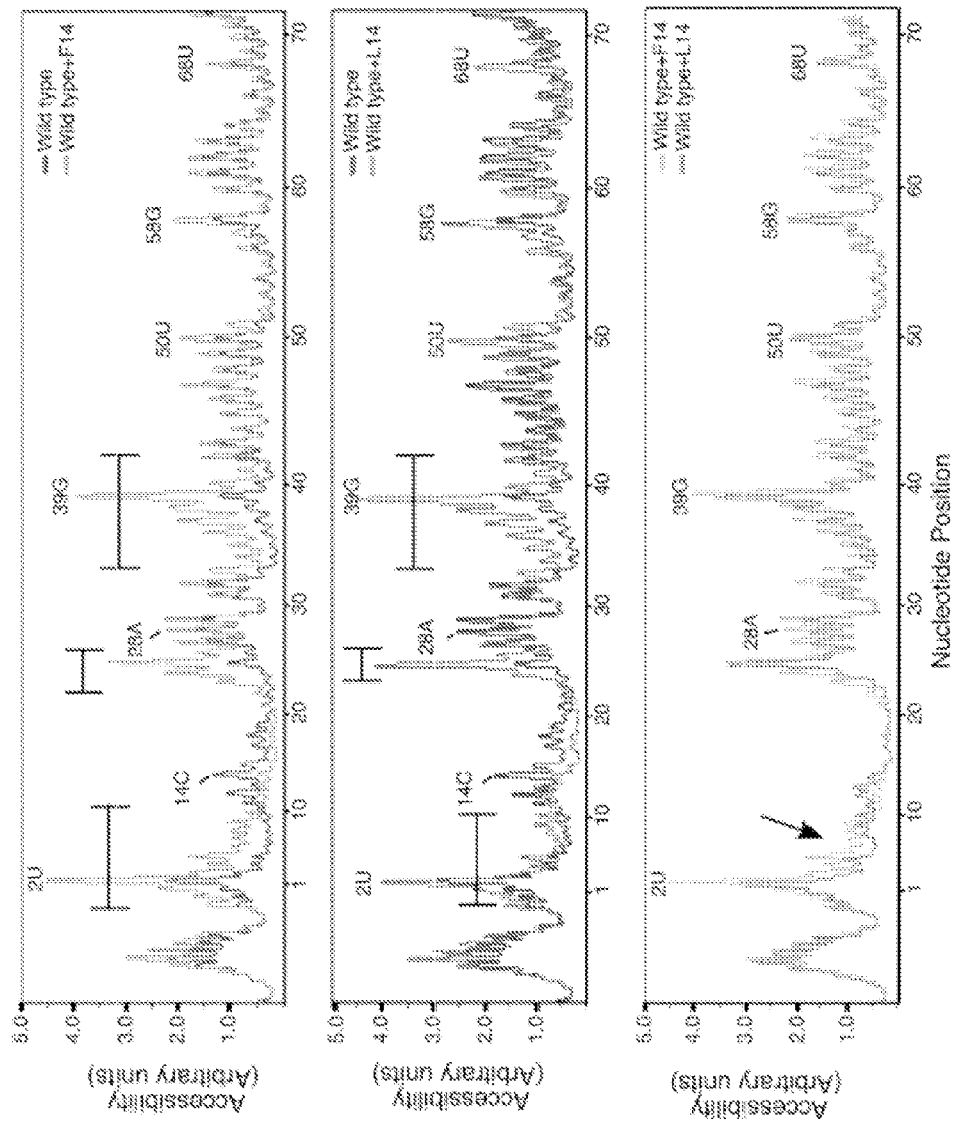

FIGS. 9A and 9B show the effect of F14 and L14 on RNA secondary structure of SMN2 intron 7. (A) SHAPE results for the wild type RNA probed in the presence of F14 and L14. Primer#10 was used to identify 1M7 modification sites. Based on the sequencing ladders, positions of residues and locations of structures are marked on the gel. Annealing positions of F14 and L14 are marked by light gray and dark gray bars, respectively. (B) Alignment of raw peak profiles for the wild type RNA refolded and probed with F14 or L14. Nucleotides that display higher reactivity towards 1M7 in the presence of F14 and L14 are indicated. The region where nucleotides are more reactive with 1M7 in the presence of F14 than in the presence of L14 is indicated by an arrow.

Figure 10A:
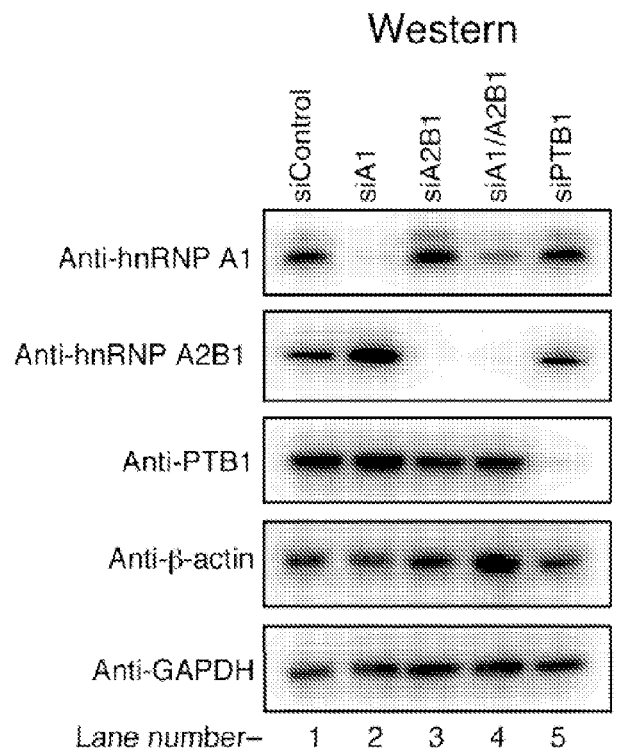
Figure 10B:
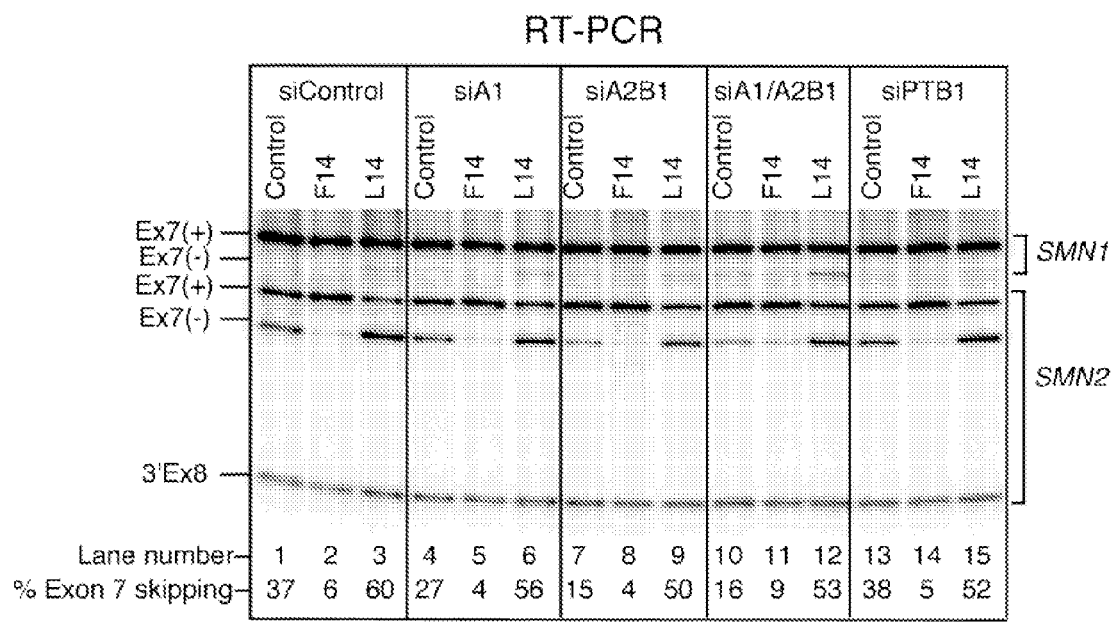

FIGS. 10A and 10B show the effect of depletion of hnRNP A1/A2B1 and PTB1 on $^{10}$C-mediated LDI. (A) Western blot results showing the effect of indicated siRNAs on the level of corresponding proteins. (B) Splicing pattern of the endogenous SMN exon 7 in the presence of the control ASO (10-mer), F14 and L14 in HeLa cells treated with different siRNAs. Control ASO was the same as described in FIG. 2. Spliced products amplified by RT-PCR were digested with DdeI to distinguish between the transcripts from SMN1 and SMN2 pre-mRNA (25). 3'Ex8 represents the cleavage product of DdeI digestion of SMN2 exon 8. The percentage of SMN2 exon skipping was calculated as in (31).

Figure 11A:
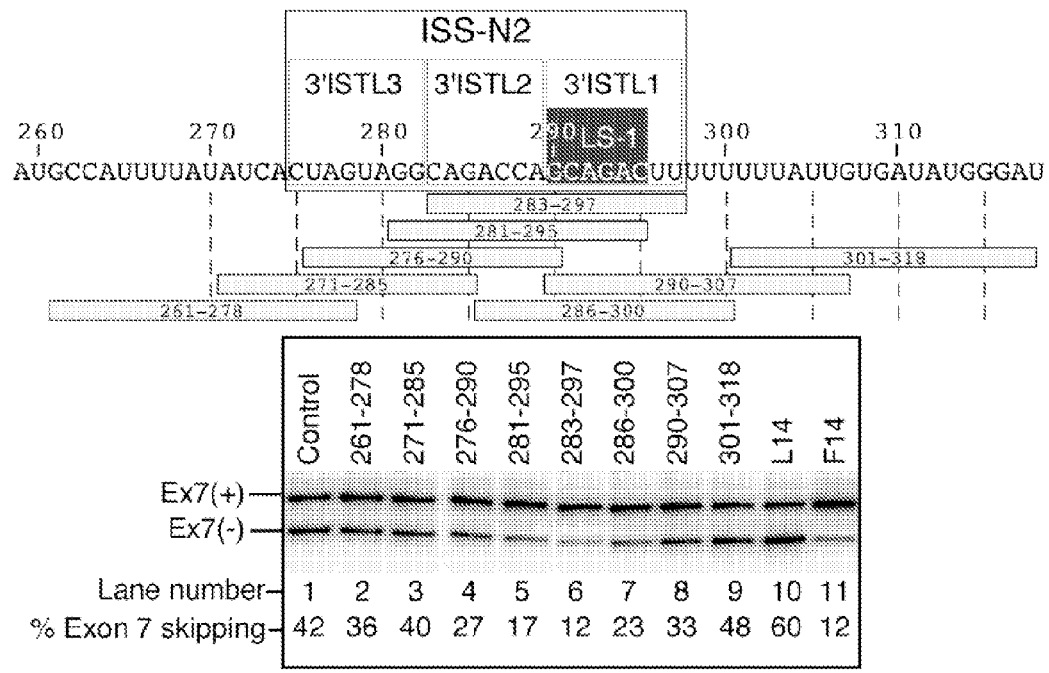
Figure 11B:
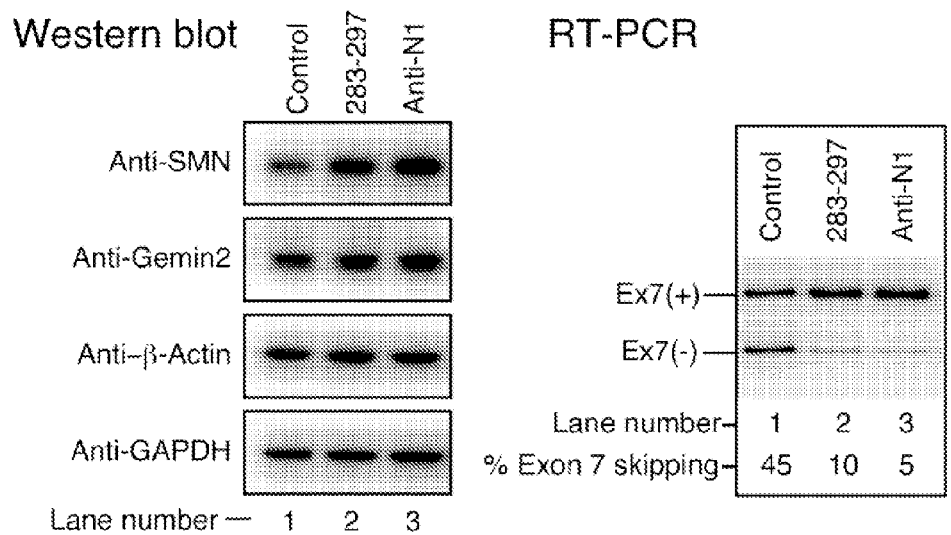

FIGS. 11A and 11B show the effect of ASOs on splicing of endogenous SMN2 exon 7 in SMA patient cells. (A) Diagrammatic representation of the region of intron 7 targeted by the indicated ASOs (SEQ ID NO: 108). Numbering of nucleotides starts from the beginning of intron 7. Areas corresponding to the 3' strands of ISTLs as well as ISS-N2 are indicated. ASOs are shown as horizontal bars. ASO name indicates the first and the last position of their target site in intron 7. SMA patient fibroblasts (GM03813) were transfected with 15 nM of a given ASO and total RNA was harvested at 24 h post transfection. Control ASO was the same as described in FIG. 2. Results were analyzed as described in (35). (B) Effect of the stimulatory ASOs on levels of cellular proteins in SMA patient cells. GM03813 cells were transfected with 40 nM of a given ASO and cells were harvested at 48 h post transfection. Splicing pattern and protein levels were determined as in (35).

Figure 12:
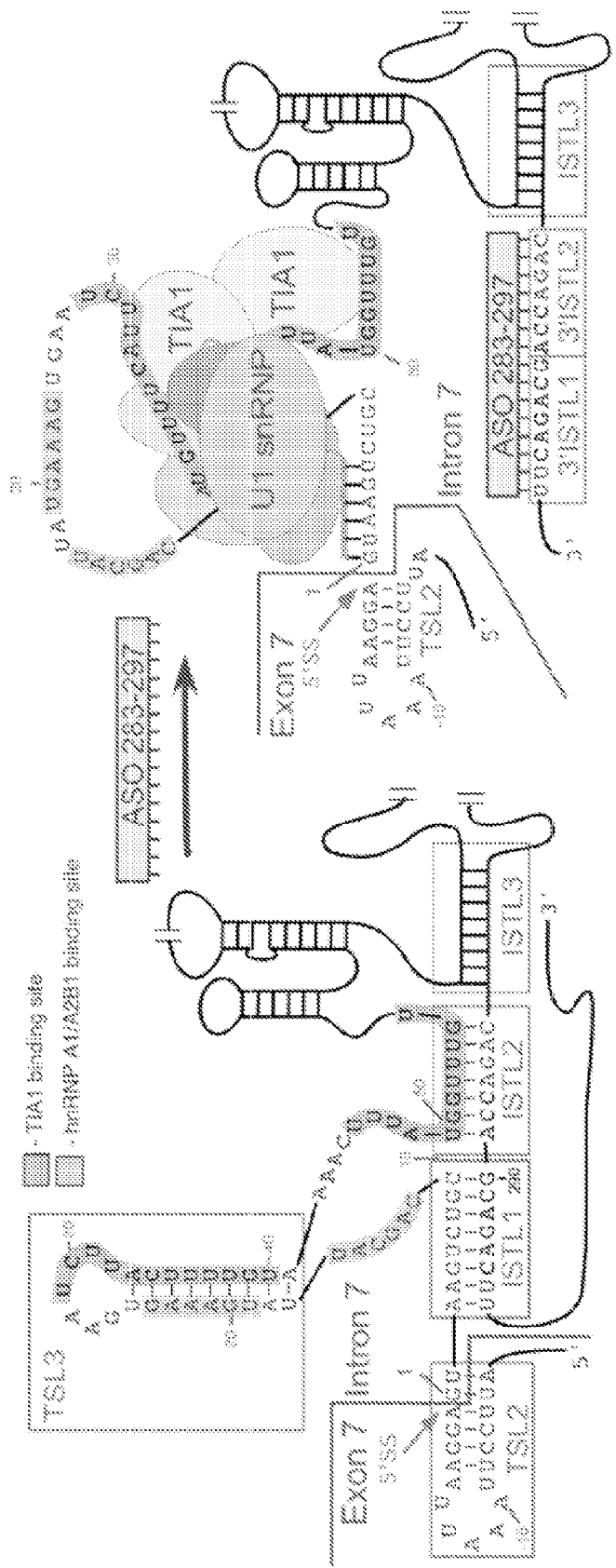

FIG. 12 shows a model of ASO-mediated correction of SMN2 exon 7 splicing. Only portions of exon 7 and intron 7 are shown (not to scale) (SEQ ID NOs: 109-112). Presented structure is based on the SHAPE results (see FIG. 5). Structural elements of interest are highlighted. Splicing factors are indicated by circles. Annealing sites of ASO 283-297 and U1 snRNA are shown. Sequestration of the 3' strands of ISTL1 and ISTL2 by ASO 283-297 releases the 5' strand of ISTL1 and disrupts TSL3. This structural rearrangement leads to enhanced recruitment of U1 snRNP at the 5' ss of exon 7 and possibly TIA1.

Figure 13A:
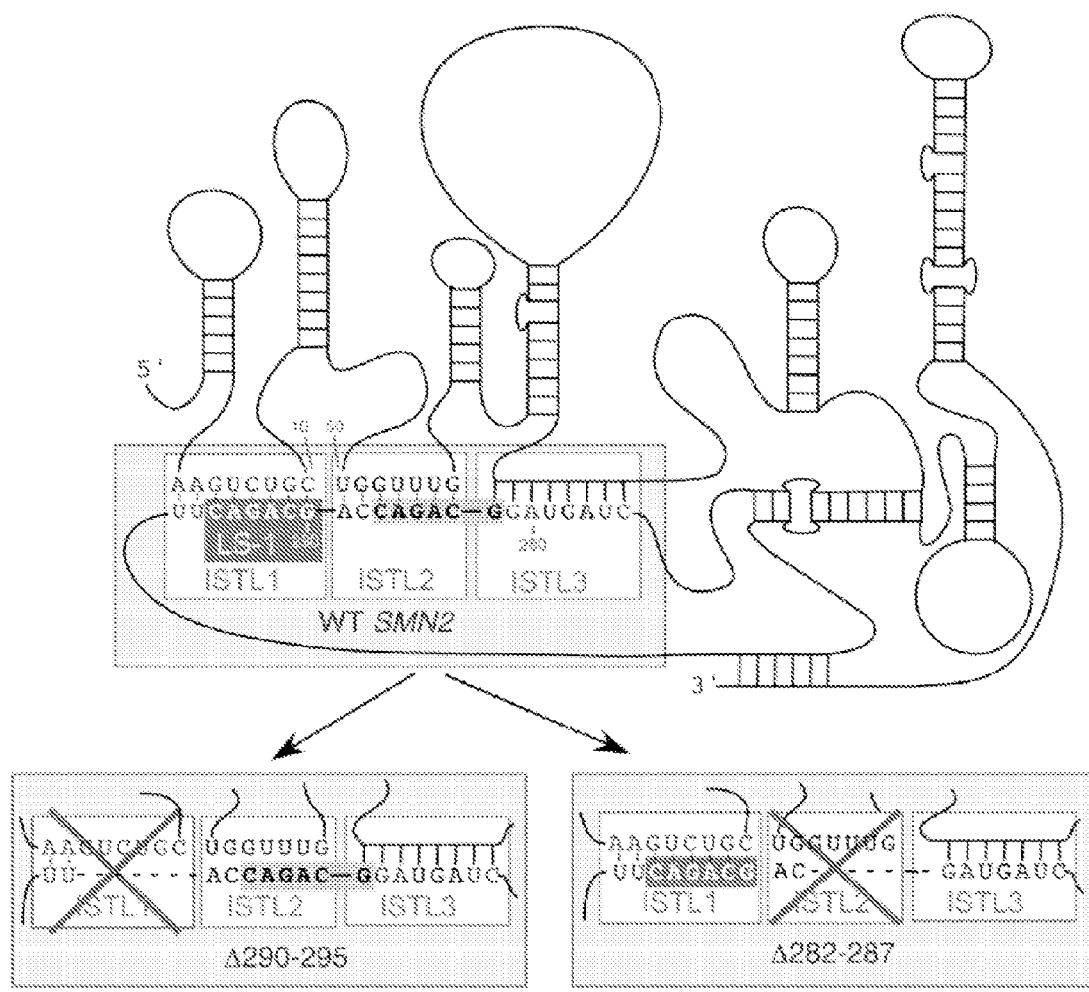
Figure 13B:
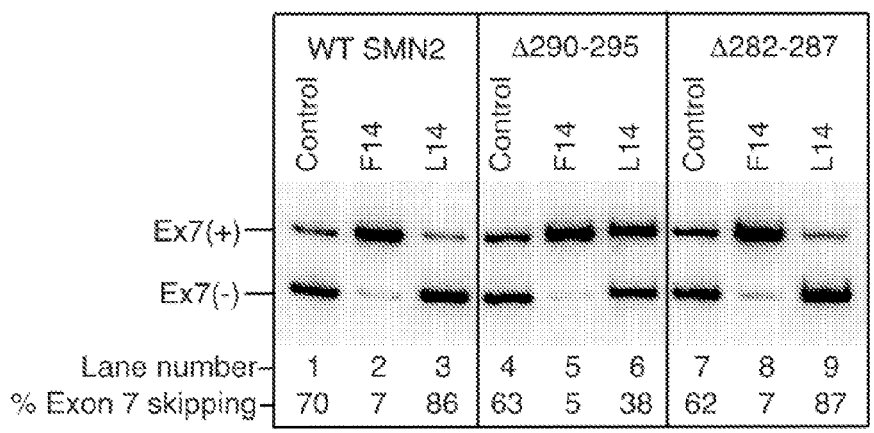

FIGS. 13A and 13B show the effect of GCAGAC motif deletion on the ability of L14 to promote exon 7 skipping. (A) Diagrammatic representation of intron 7 structure (SEQ ID NOs: 12, 113, 114). Sequence and structural contexts of GCAGAC motifs are highlighted. Numbering of nucleotides starts from the beginning of intron 7. (B) In vivo splicing pattern of the wild type SMN2 minigene and the deletion mutants shown in panel (A) in the presence of the indicated ASOs. Deletion of GCAGAC motif in the region from position 290 to 295 but not from 282 to 287 abrogated the negative effect of L14 on exon 7 splicing. Exon 7-included (+) and exon 7-skipped (−) spliced products are indicated. Control represents transfection with 10-mer ASO (Table 2). Results were analyzed as described FIG. 2B. Abbreviation Ex7 stands for exon 7.

Figure 14:
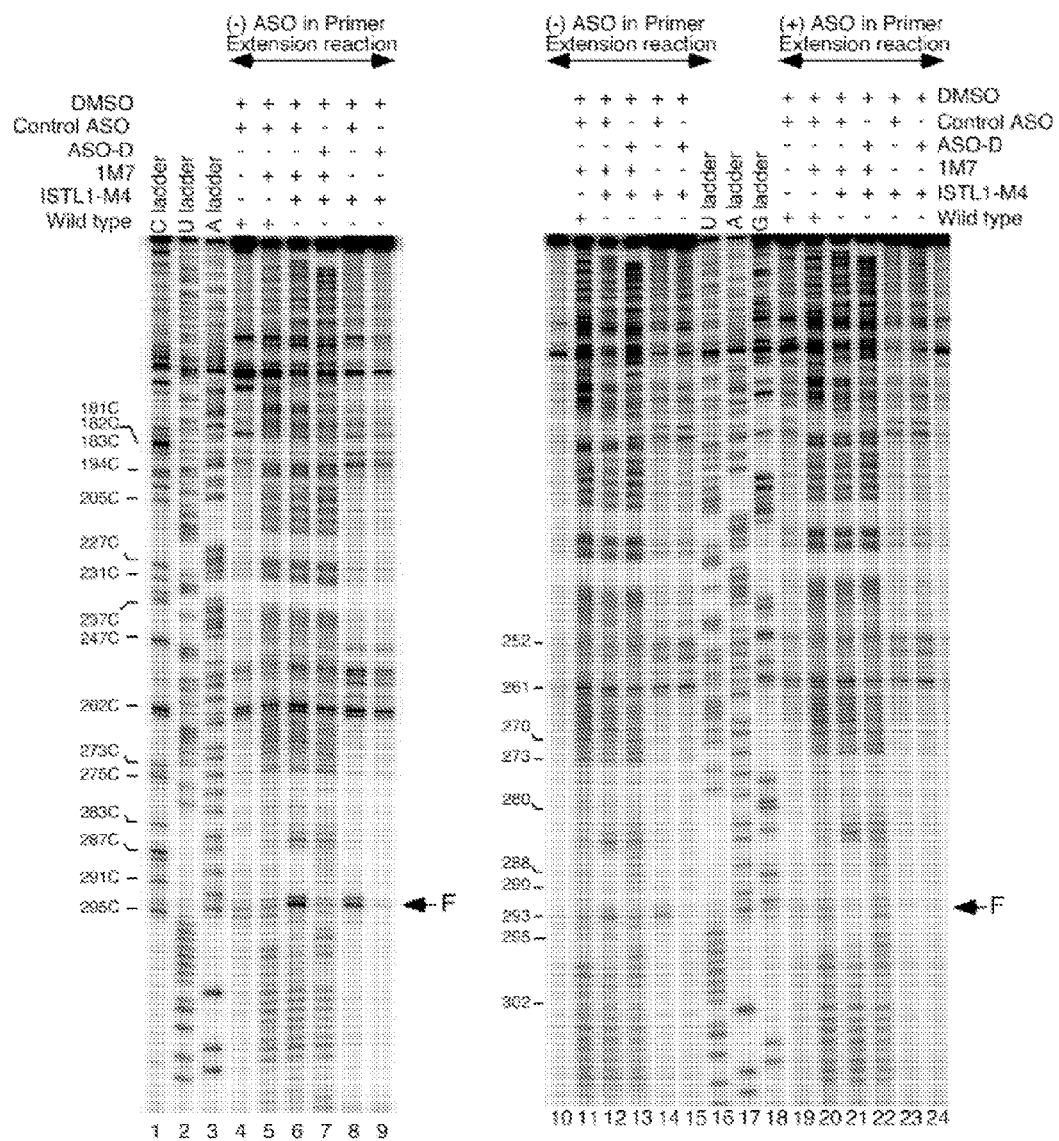

FIG. 14 shows the strengthening of ISTL1 structure in the mutant is corroborated by falloff products in primer extension reactions. The wild type and ISTL1-M4 mutant RNAs were subjected to 1M7 modification. Modification sites were identified by primer extension using primer#17 (left panel) or primer#315 (right panel). Extension reactions with primer#17 and primer #315 were performed on RNA substrates generated and subjected to 1M7 modification at different times. Primer extension products were separated on denaturing 6% polyacrylamide gels. Presence and absence of ASO-D in primer extension reactions are indicated by (+) and (−), respectively. "Falloff" bands corresponding to positions 292 and 293 in both 1M7 treated and untreated mutant RNA are indicated by arrows (lanes 6 and 8 for primer#17 and lanes 12 and 14 for primer#315). When ASO-D was added to primer extension reaction, these bands disappeared in ISTL1-M4 samples (lanes 21 to 23 for primer#315; also see FIG. 8, lanes 6 and 8 for primer#17). Therefore, we attribute 292 and 293 falloff products to a strong RNA structure.

Figure 15A:
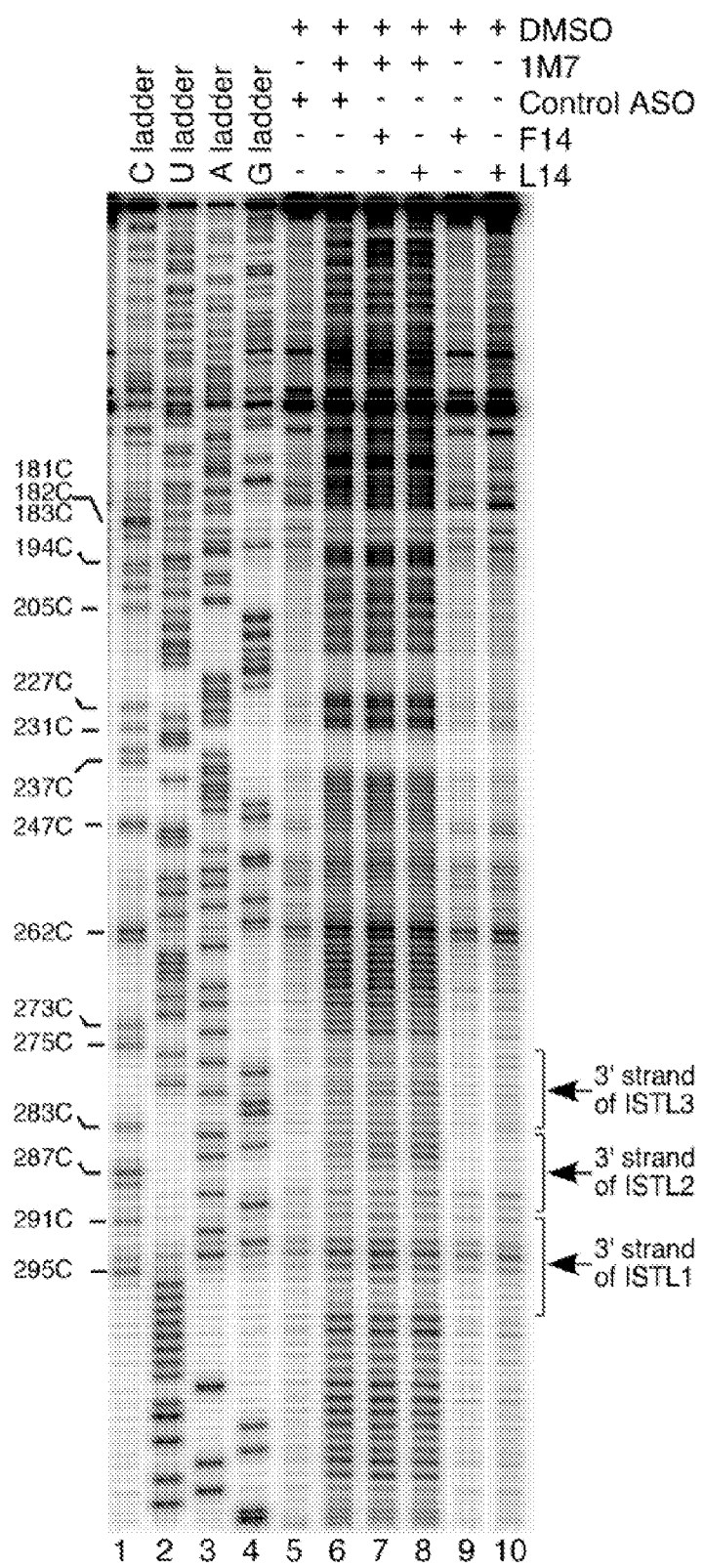
Figure 15B:
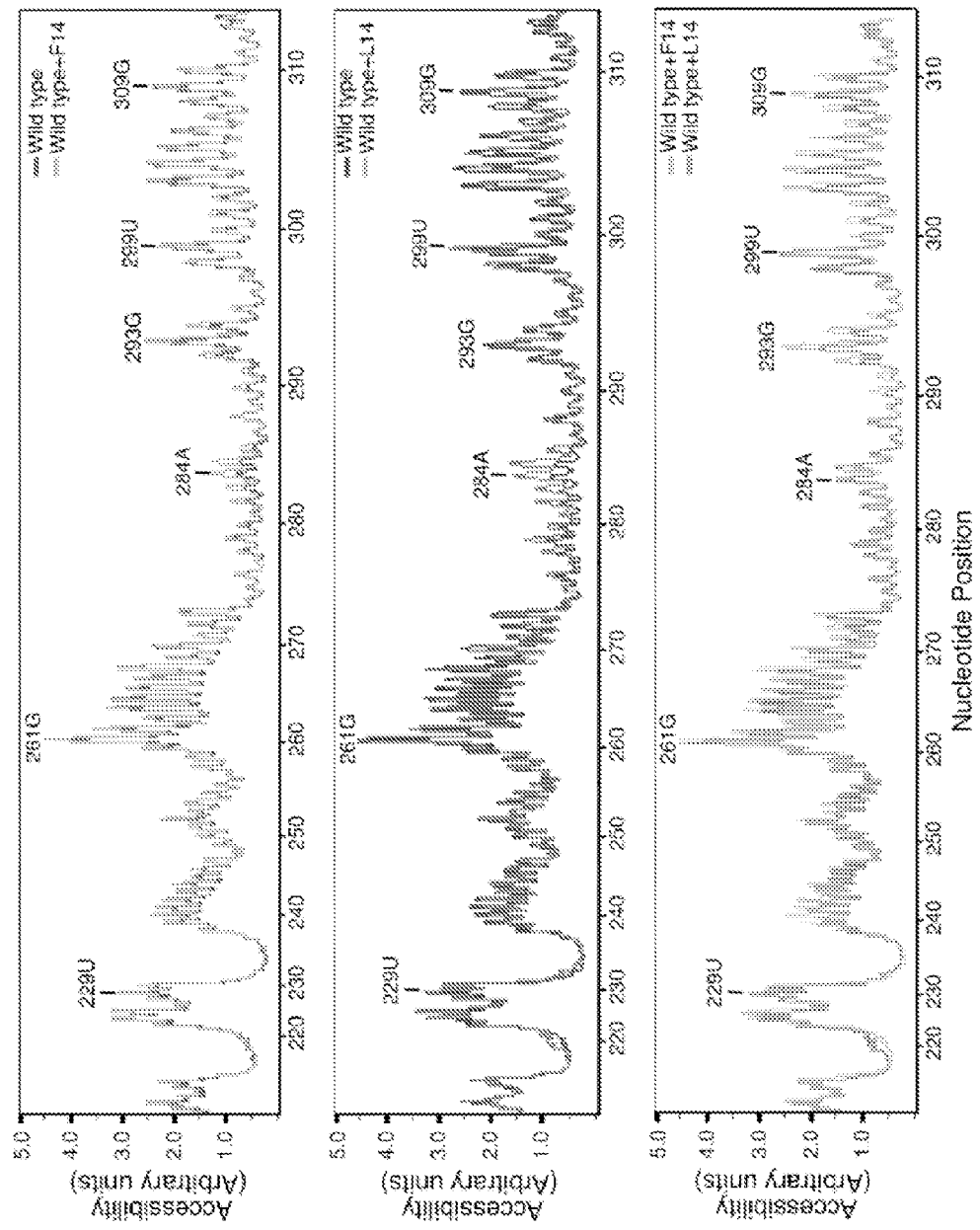

FIGS. 15A and 15B show the effect of F14 and L14 on RNA secondary structure of the middle portion of intron 7 probed by SHAPE. (A) SHAPE results for the wild type intron 7 in the presence of F14 and L14. RNA substrate refolded in the presence of the control ASO, F14 or L14 was subjected to 1M7 modification. Modification sites were then identified by primer extension using primer#17. Primer extension products were separated on denaturing 6% polyacrylamide gels. Based on the sequencing ladders, positions of residues and locations of structures are marked on the gel. (B) Alignment of raw peak profiles for the wild type RNA refolded and probed with F14 versus with L14.

Figure 16:
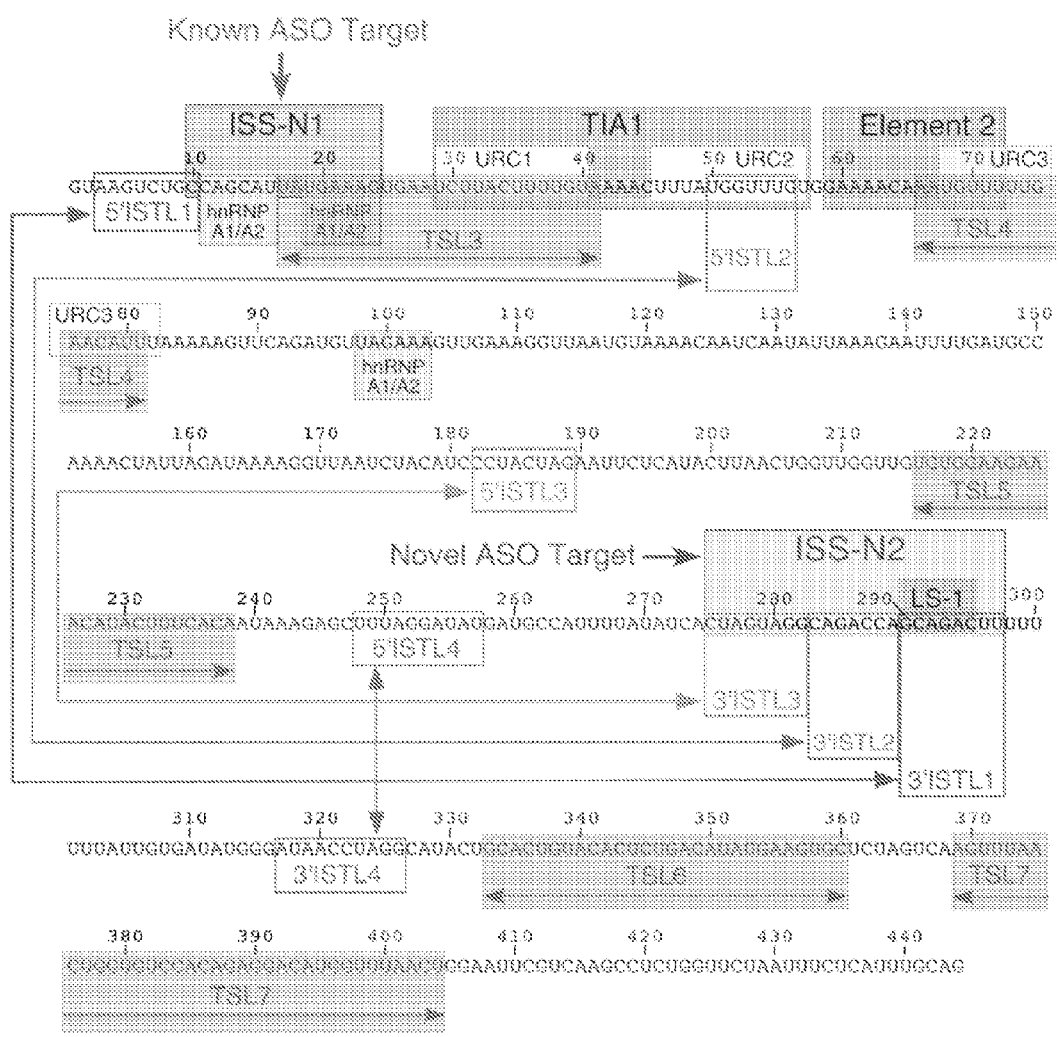

FIG. 16 shows the relative positioning of the structural and splicing cis-elements on the linear structure of SMN2 intron 7. Entire SMN2 intron 7 sequence is shown (SEQ ID NO: 14). Numbering starts from the first position of intron 7. Double arrow within a box represents a TSL, whereas, a double arrow outside of the box in specific color shows the 5' and 3' strands of a particular ISTL. ISS-N2, a novel therapeutic target, is comprised of the 3' strands of ISTL1, ISTL2 and ISTL3. Descriptions of abbreviations are given in the main body of the text as well as in the Table 1.

Figure 17:
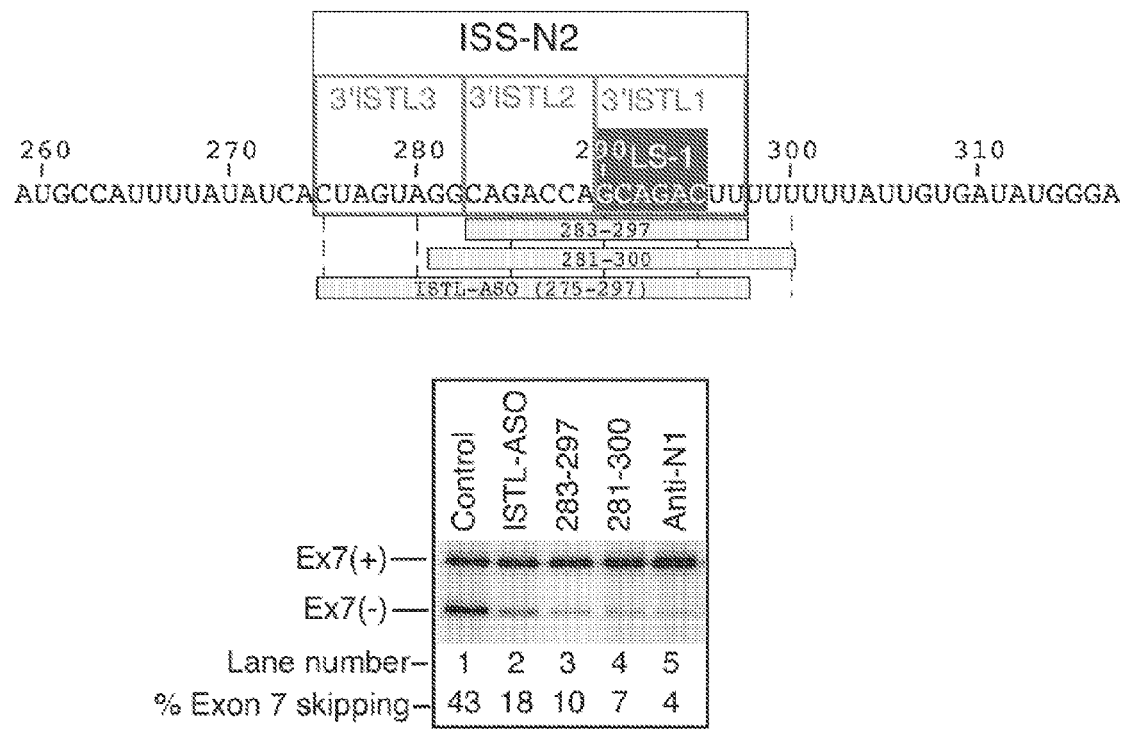

FIG. 17 shows the effect of ISS-N2 targeting ASOs on SMN2 exon 7 splicing in SMA patient cells with the longer 23 base ASO ISTL (SEQ ID NO: 13). Experiments were performed with 20 nM ASOs and splicing pattern was determined 24 h post transfection. All ISS-N2 targeting ASOs including ISTL-ASO promoted SMN2 exon 7 inclusion in SMA patient cells (SEQ ID NO: 115).

Figure 18:
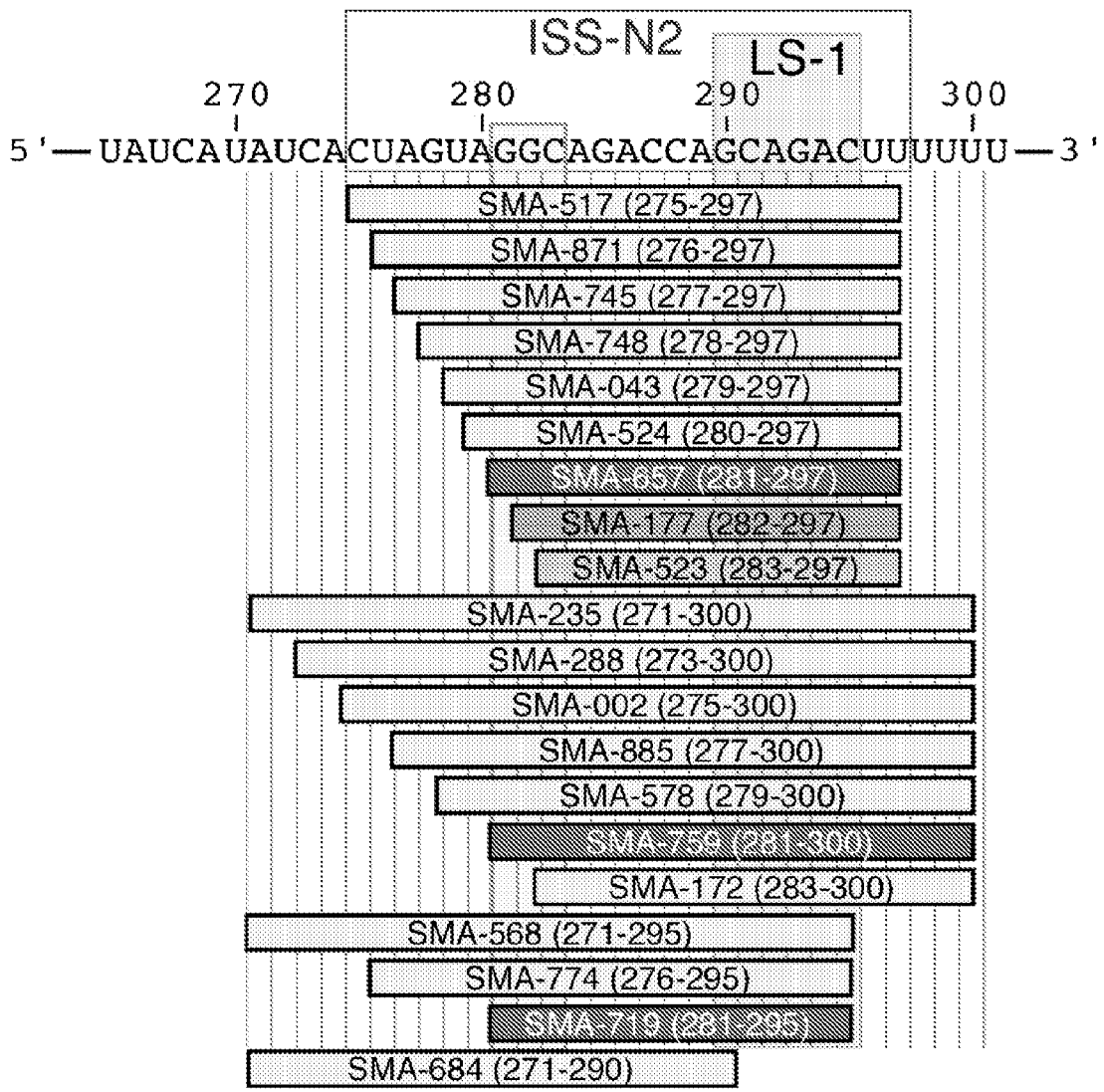

FIG. 18 is a schematic representation of antisense target (ISS-N2) within SMN2 intron 7. Role of ISS-N2 on SMN2 exon 7 splicing has been recently described (Singh et al., 2013). Numbering starts from the first position of intron 7 (SEQ ID NO: 116). Horizontal bars represent ASOs. Horizontal bars in dark gray colors represent the most effective ISS-N2-targeting ASOs in promoting SMN2 exon 7 inclusion. GCC sequence and LS-1 are highlighted.

Figure 19:
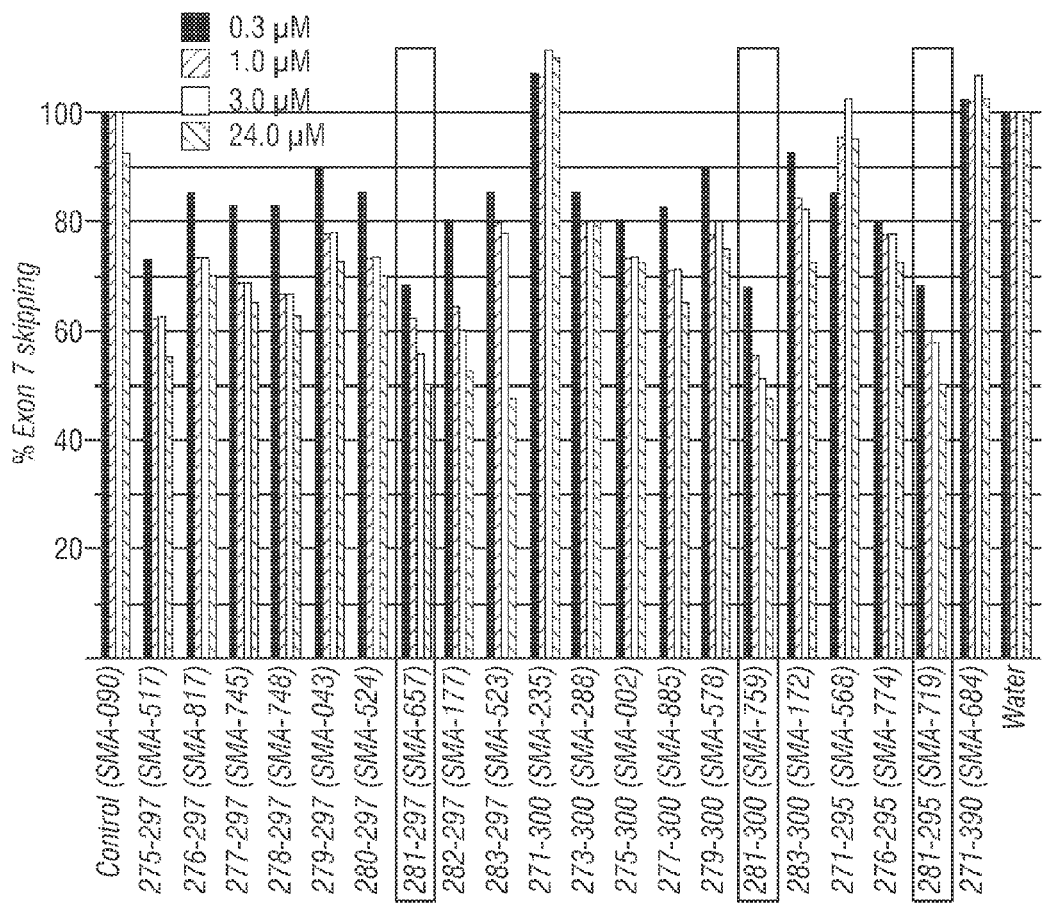

FIG. 19 shows the effect of morpholino ASOs on splicing of SMN2 exon 7 in SMA patient cells. ASOs were delivered into SMA type I patient fibroblasts (GM 03813) using Nucleofector technology, and the effect on splicing of exon 7 was tested ~24 hours later by RT-PCR using total RNA prepared from nucleofected cells. Effect of a given ASO on SMN2 exon 7 splicing was compared with the mock (water) nucleofected sample. Skipping of SMN2 exon 7 in water-transfected sample was considered as 100%. SMA-759 (ASO 281-300), SMA-657 (ASO 281-297) and SMA-719 (ASO 281-295) emerged as three lead ISS-N2-targeting morpholino ASOs. A control ASO (SMA-090) with scrambled sequence produced a negligible effect on SMN2 exon 7 splicing at all concentrations tested.

Figure 20:
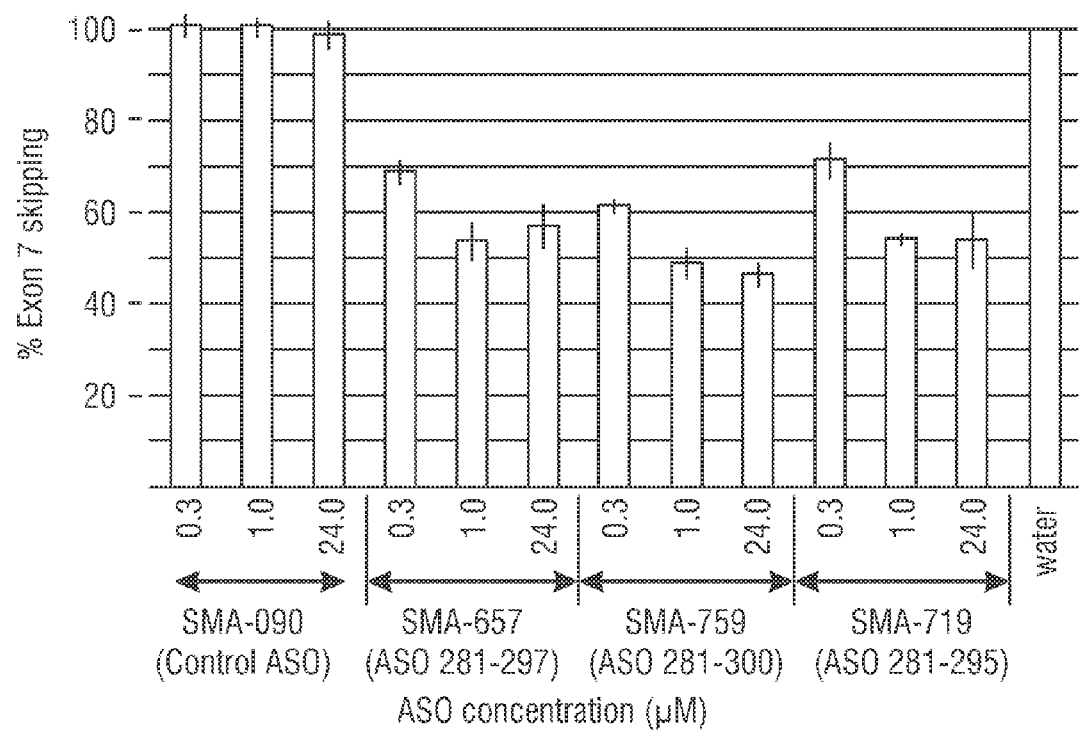

FIG. 20 shows the effect of lead morpholino ASOs on splicing of SMN2 exon 7 in SMA patient cells. Experiments were performed similarly as in FIG. 2, except effect of ASOs on SMN2 exon 7 splicing was determined ~48 hours post nucleofection. Bars represent an average of three independent experiments performed for each ASO concentration. All three ISS-N2-targeting lead ASOs (SMA-657, SMA-759 and SMA-719) showed substantial inclusion of SMN2 exon 7 at 1 µM concentration. A control ASO (SMA-090) with scrambled sequence produced a negligible effect on SMN2 exon 7 splicing at all concentrations tested.

DETAILED DESCRIPTION OF THE INVENTION

The present invention relates to the discovery that targeting ISS-N2 including a critical six base sequence in the second half of intron 7 of the SMN2 gene enhances production of full-length SMN2 transcripts (transcripts containing exon 7) by abrogating an inhibitory LDI during splicing. In particular, the present inventors have identified a 23-nucleotide long inhibitory region that spans from $275^{th}$ to $297^{th}$ positions in intron 7 and a particularly critical 6 base sequence of from $290^{th}$ to $295^{th}$ positions for design of novel intronic inhibitory sequence elements. Previous targets and inhibitory sequence elements included a critical single nucleotide in intron 7, $^{10}C$ that somehow prevents formation of catalytic core for SMN2 exon 7 splicing. Applicants have now demonstrated that the inhibitory effect on unpaired $^{10}C$ is dependent on a long-distance interaction involving downstream intronic target sequences based on long-distance steric interactions including LS-1 sequence, which is located within ISS-N2, a novel and complex regulatory element. Applicants have also demonstrated that $^{10}C$-associated LDI is realized through an inhibitory RNA:RNA duplex, ISTL1, which is close to the 5' slice site of exon 7. Thus sequestration of ISTL1 that harbors LS-1 promotes SMN2 exon 7 inclusion in patient cells.

Accordingly, the invention is directed to effective use of blocking compounds, in particular, oligonucleotide reagents (e.g., antisenseoligonucleotide analogs) to inhibit this intronic splice-inhibitory sequence target. The region from the $275^{th}$ to $297^{th}$ positions (SEQ ID NO: 12) of intron 7 and particularly the 6-mer sequence motif (GCAGAC) were identified to play a dominant role in production of exon 7-deleted SMN2 transcripts. Oligonucleotide reagents complementary to these regions will enhance inclusion of exon 7 during splicing of SMN2 transcript in SMA fibroblasts, thus restoring production of full-length SMN2 mRNA transcripts.

The invention is also directed to therapies that displace and/or disrupt the critical target sequences identified herein. These results demonstrated for the first time a critical target site initiated by long distance interaction involving a deep intronic sequence.

The present invention provides compositions for blocking the novel intronic splicing silencer, ISS-N2 that harbors complex sequence and structure motifs within SMN2 intron 7. In particular, the invention provides compositions comprising oligonucleotide reagents (e.g., antisense agents or dsDNA cassettes) that block the splice inhibitory effects of the intron 7 target sequences, thereby modulating splicing of the SMN2 pre-mRNA to include exon 7 in processed forms of the transcript. Agents capable of blocking the inhibitory effect of this region will possess high value as SMA therapeutics. Such agents can also be used in treatment of diseases associated with high susceptibility to oxidative stress such as exposure to Paraquat and induced Parkinson's disease, as well as amyotrophic lateral sclerosis (ALS), another neurological disease characterized by low levels of SMN protein (Veldink, J. H., et al. 2005 Neurology 65(6): 820-5). The invention therefore provides agents capable of blocking the splice-inhibitory effect of the SMN2 intron 7. The invention also provides avenues to disrupt the inhibitory RNA-protein interaction(s) with the target sequences disclosed herein, agents that sequester target sequence and agents that disrupt the structure of the target sequence herein and/or surrounding region.

In exemplary embodiments, the instant invention is directed to oligonucleotide reagents capable of promoting SMN2 exon 7 splicing via direct interaction and/or hybridization with a novel silencer (ISS-N2) located deep within intron 7. To enhance the therapeutic value of such RNA-complementary oligonucleotides, the invention is further directed to compositions comprising modified forms of such oligonucleotides, e.g., phosphorothioate-, 2'-O-methyl-, morpholino, etc.-modified oligonucleotides, as such modifications have been recognized in the art as improving the stability of oligonucleotides in vivo. The instant invention also is directed to methods for identifying target sequence-interacting proteins, as such methods are enabled by the instant discovery and characterization of the critical sequence targeted by $^{10}$C which enables long distance interaction and inhibition.

So that the invention may be more readily understood, certain terms are first defined.

The term "nucleoside" refers to a molecule having a purine or pyrimidine base covalently linked to a ribose or deoxyribose sugar. Exemplary nucleosides include adenosine, guanosine, cytidine, uridine, inosine, and thymidine. The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms.

The term "RNA" or "RNA molecule" or "ribonucleic acid molecule" refers to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

The term "antisense oligonucleotide analog" or "nucleotide analog" or "altered nucleotide" or "modified nucleotide" refers to a non-standard nucleotide, including non-naturally occurring ribonucleotides or deoxyribonucleotides. Preferred nucleotide analogs are modified at any position so as to alter certain chemical properties of the nucleotide yet retain the ability of the nucleotide analog to perform its intended function. Examples of positions of the nucleotide which may be derivatized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., August 2000 10(4):297-310.

Nucleotide analogs may also comprise modifications to the sugar portion of the nucleotides. For example the 2' OH-group may be replaced by a group selected from H, OR, R, F, Cl, Br, I, SH, SR, NH$_2$, NHR, NR$_2$, COOR, or OR, wherein R is substituted or unsubstituted C$_1$-C$_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. April 2000 10(2): 117-21, Rusckowski et al. Antisense Nucleic Acid Drug Dev. October 2000 10(5):333-45, Stein, Antisense Nucleic Acid Drug Dev. October 2001 11(5): 317-25, Vorobjev et al. Antisense Nucleic Acid Drug Dev. April 2001 11(2):77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro.

As used herein the term "antisense oligonucleotide analog" includes but is not limited to a "morpholino oligomer" or "PMO" which refers to an oligonucleotide having a backbone which supports a nucleobase capable of hydrogen bonding to typical polynucleotides, wherein the polymer lacks a pentose sugar backbone moiety, but instead contains a morpholino ring. Thus, in a PMO a morpholino ring structure supports a base pairing moiety, to form a sequence of base pairing moieties which is typically designed to hybridize to a selected antisense target in a cell or in a subject being treated. An exemplary "morpholino" oligomer comprises morpholino subunit structures linked together by phosphoramidate or phosphorodiamidate linkages, joining the morpholino nitrogen of one subunit to the 4' exocyclic carbon of an adjacent subunit, each subunit comprising a purine or pyrimidine nucleobase effective to bind, by base-specific hydrogen bonding, to a base in a polynucleotide. Morpholino oligomers (including antisense oligomers) are detailed, for example, in U.S. Pat. Nos. 5,698,685; 5,217,866; 5,142,047; 5,034,506; 5,166,315; 5,185,444; 5,521,063; 5,506,337 and pending U.S. patent application Ser. Nos. 12/271,036; 12/271,040; and PCT publication number WO/2009/064471 all of which are incorporated herein by reference in their entirety.

Within the oligonucleotide structure, the phosphate groups are commonly referred to as forming the "internucleoside linkages" of the oligonucleotide. The naturally occurring internucleoside linkage of RNA and DNA is a 3' to 5' phosphodiester linkage. A "phosphoramidate" group comprises phosphorus having three attached oxygen atoms and one attached nitrogen atom, while a "phosphorodiamidate" group comprises phosphorus having two attached oxygen atoms and two attached nitrogen atoms. In the uncharged or the cationic intersubunit linkages of the PMO and/or PMOX oligomers described herein, one nitrogen is always pendant to the backbone chain. The second nitrogen, in a phosphorodiamidate linkage, is typically the ring nitrogen in a morpholino ring structure.

"PMOX" refers to phosporodiamidate morpholino oligomers having a phosphorus atom with (i) a covalent bond to the nitrogen atom of a morpholino ring and (ii) a second covalent bond to the ring nitrogen of a 4-aminopiperdin-1-yl (i.e. APN) or a derivative of 4-aminopiperdin-1-yl. PMOX oligomers are disclosed in PCT application No. PCT/US 11/38459 (published as WO/2011/150408), herein incorporated by reference in its entirety. "PMOapn" or "APN" refers to a PMOX oligomer where a phosphorus atom is linked to a morpholino group and to the ring nitrogen of a 4-aminopiperdin-1-yl (i.e. APN).

As used herein, the term "intronic splicing silencer-N1" or "ISS-N1" refers to the 15 nucleotide sequence 5'-CCAGCAUUAUGAAAG-3' (SEQ ID NO: 35) previously known target within intron 7 of SMN.

As used herein, the term "intronic splicing silencer-N2" or "ISS-N2" refers to the 23 nucleotide sequence 5'-CUAGUAGGCAGACCAGCAGACUU-3' (SEQ ID NO: 12), an entirely novel target within intron 7 of SMN.

The term "oligonucleotide" refers to a short polymer of nucleotides and/or nucleotide analogs. An "oligonucleotide reagent" of the invention includes any agent, compound or composition that contains one or more oligonucleotides, and includes, e.g., reagents comprising both single stranded and/or double stranded (ds) oligonucleotide compositions, including, e.g., single stranded RNA, single stranded DNA, DNA/DNA and RNA/DNA hybrid compositions, as well as derivatized/modified compositions thereof. Such "oligonucleotide reagents" may also include amplified oligonucleotide products, e.g., polymerase chain reaction (PCR) products. An "oligonucleotide reagent" of the invention may also include art-recognized compositions designed to mimic the activity of oligonucleotides, such as morpholinos (PMO), locked nucleic acid (LNA), and peptide nucleic acid (PNA) molecules.

The term "oligoribonucleotide" refers to a short polymer of ribonucleotides and/or ribonucleotide analogs.

An "oligoribonucleotide" of the invention can include one or a few deoxyribonucleotides or deoxyribonucleotide analogs in order to enhance the stability and/or bioaccessibility of the molecule, in order that ISS-N2 blocking activity occurs absent degradation of the target RNA (i.e., absent the RNase H degradation triggered by oligodeoxyribonucleotides or DNA:RNA hybridization).

Preferably, the oligonucleotide reagent molecules/agents of the invention act (or are effective) at a concentration (e.g., have an IC50) in the nanomolar range, for example, less than 500 nM, preferably less than 400 nM, more preferably less than 300, 250, 200, 150, 100, 75, 50, 25, 10, 5, 2 or 1 nM.

Preferred oligonucleotide analogs are modified oligonucleotides having a length of about 5 to 50 nucleotides (or nucleotide analogs), e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nucleotides (or nucleotide analogs). In preferred embodiments, oligonucleotide reagent molecules/agents are modified oligonucleotides having a length of about 15 to 40, 20-40, 20-30, or 15-30 nucleotides (or nucleotide analogs). In other embodiments, oligonucleotide reagent molecules/agents are modified oligonucleotides having a length of about 3 to 80 nucleotides (or nucleotide analogs), or for example, about 3-10, 10-15, 15-20, 20-25, 25-30, 30-35, 35-40, 40-45, 45-50, 50-55, 55-60, 60-65, 65-70, 70-75, 75-80 or more nucleotides (or nucleotide analogs). Preferably the oligonucleotide includes at least 10, 11, 12, 13, 14, 15 or more consecutive bases of SEQ ID NO:1, 4, 5, 6, 7, 8, 9, or 13 with length of 15 to 40, 15 to 30, or 20 to 30.

The term "agent" and "compound" are used interchangeably herein.

As used herein, the term "nuclease-resistant oligonucleotide" refers to any oligonucleotide that has been modified to inhibit degradation by enzymes such as, for example, the exonucleases and endonucleases known to be present in the eukaryotic cell. RNA molecules (e.g., RNA oligonucleotides) are particularly at risk of degradation when combined with a composition comprising a cell extract or when introduced to a cell or organism, and a "ribonuclease-resistant" oligonucleotide is thus defined as an oligonucleotide reagent molecule/agent that is relatively resistant to ribonuclease enzymes (e.g., exonucleases), as compared to an unmodified form of the same oligonucleotide. Preferred oligonucleotide reagent molecules/agents of the invention include those that have been modified to render the oligonucleotide relatively nuclease-resistant or ribonuclease-resistant. In a preferred embodiment, the oligonucleotide reagents of the invention have been modified with a 2'-O-methyl group (e.g., 2'-O-methylcytidine, 2'-O-methylpseudouridine, 2'-O-methylguanosine, 2'-O-methyluridine, 2'-O-methyladenosine, 2'-O-methyl) and additionally comprise a phosphorothioate backbone.

The terms "2'-O-methyl modification", "phosphorothioate modification" and "locked nucleic acid" (LNA; oligonucleotides comprising at least one 2'-C,4'-C-oxy-methylene-linked bicyclic ribonucleotide monomer), as used herein, possess their art-recognized meanings.

The term "antisense" refers generally to any approach reliant upon agents, e.g., single-stranded oligonucleotides, that are sufficiently complementary to a target sequence to associate with the target sequence in a sequence-specific manner (e.g., hybridize to the target sequence). Exemplary uses of antisense in the instant application involve use of an antisense oligonucleotide analog that hybridizes to a target pre-mRNA molecule and blocks an activity/effect (e.g., splicing pattern) of the targeted pre-mRNA sequence, but antisense approaches commonly are used to target DNA or RNA for transcriptional inhibition, translational inhibition, degradation, etc. Antisense is a technology that can be initiated by the hand of man, for example, to modulate splicing and/or silence the expression of target genes.

As used herein, the term "antisense oligonucleotide analog" "antisense oligonucleotide" or "ASO" or "AON" are all used interchangeably and refer to a nucleic acid (in preferred embodiments, an RNA) (or analog thereof), having sufficient sequence complementarity to a target RNA (i.e., the RNA for which splice site selection is modulated) to block a region of a target RNA (e.g., pre-mRNA) in an effective manner. In exemplary embodiments of the instant invention, such blocking of the ISS-N1 or ISS-N2 domain in SMN2 pre-mRNA serves to modulate splicing, either by masking a binding site for a native protein that would otherwise modulate splicing and/or by altering the structure of the targeted RNA. In preferred embodiments of the instant invention, the target RNA is a target pre-mRNA (e.g., SMN2 pre-mRNA). An antisense oligonucleotide having a "sequence sufficiently complementary to a target RNA sequence to modulate splicing of the target RNA" means that the antisense agent has a sequence sufficient to trigger the masking of a binding site for a native protein that would otherwise modulate splicing and/or alters the three-dimensional structure of the targeted RNA. Likewise, an oligonucleotide reagent having a "sequence sufficiently complementary to a target RNA sequence to modulate splicing of the target RNA" means that the oligonucleotide reagent has a sequence sufficient to trigger the masking of a binding site for a native protein that would otherwise modulate splicing and/or alters the three-dimensional structure of the targeted RNA. As used herein, the terms "ISS-N2 blocking agent," "ISS-N2 blocker," and "ISS-N2 blocking compound" refer to any agent (e.g., oligonucleotide, oligoribonucleotide, small molecule, etc.) that is capable of inhibiting the effect of the SMN2 ISS-N2 site and its interaction with $^{10}$C (e.g., lessen the inhibition of SMN2 exon 7 inclusion during splicing that is caused by the long distance interaction between the two). As used herein, the terms "LS-1 blocking agent," "LS-1 blocker," and "LS-1 blocking compound" refer to any agent (e.g., oligonucleotide, oligoribonucleotide, small molecule, etc.) that is capable of inhibiting the effect of the SMN2 LS-1 site and its interaction with $^{10}$C (e.g., lessen the inhibition of SMN2 exon 7 inclusion during splicing that is caused by the long distance interaction between the two). As used herein, the terms "ISTL abrogating agent," "ISTL blocker," and "ISTL blocking compound" refer to any agent (e.g., oligonucleotide, oligoribonucleotide, small molecule, etc.) that is capable of inhibiting the effect of the SMN2 ISTL1/ISTL2/ISTL3 sites and its interaction with its complementary partner strand.

As used herein, the term "antisense strand" as it pertains to an oligonucleotide reagent refers to a strand that is substantially complementary to a section of about 10-50 nucleotides, e.g., about 15-30, 16-25, 18-23 or 19-22 nucleotides of the pre-mRNA targeted for modulation of splicing. The antisense strand has sequence sufficiently complementary to the desired target pre-mRNA sequence to direct target-specific modulation of RNA splicing (e.g., complementarity sufficient to trigger the formation of a desired target mRNA through modulation of splicing via, e.g., altered recruitment of the splicing machinery or process).

As used herein, the "5' end", as in the 5' end of an antisense strand, refers to the 5' terminal nucleotides, e.g., between one and about 5 nucleotides at the 5' terminus of the antisense strand. As used herein, the "3' end", as in the 3' end of a sense strand, refers to the region, e.g., a region of between one and about 5 nucleotides, that is complementary to the nucleotides of the 5' end of the complementary antisense strand.

An oligonucleotide reagent "that directs altered RNA splicing of a gene" is an oligonucleotide that has a sequence sufficiently complementary to the target mRNA encoded by a gene to trigger altered splicing of the target mRNA by the splicing machinery or process, or, alternatively, is an oligonucleotide reagent that disrupts ISTL1 or blocks LS-1 sequence.

As used herein, the term "isolated sequence" (e.g., "isolated oligonucleotide" or "isolated oligoribonucleotide") refers to sequences which are substantially free of other cellular material, or culture medium when produced by recombinant techniques, or substantially free of chemical precursors or other chemicals when chemically synthesized.

As used herein, the term "SMA" refers to spinal muscular atrophy, a human autosomal recessive disease that is often characterized by underexpression of SMN protein in affected individuals.

The term "substituted", particularly with respect to an alkyl, alkoxy, thioalkoxy, or alkylamino group, refers to replacement of a hydrogen atom on carbon with a heteroatom-containing substituent, such as, for example, halogen, hydroxy, alkoxy, thiol, alkylthio, amino, alkylamino, imino, oxo (keto), nitro, cyano, or various acids or esters such as carboxylic, sulfonic, or phosphonic. It may also refer to replacement of a hydrogen atom on a heteroatom (such as an amine hydrogen) with an alkyl, carbonyl or other carbon containing group.

As used herein, the term "target" refers to a RNA region, and specifically, to a region identified by $275^{th}$ to $297^{th}$ positions of intron 7, particularly the 6-mer GCAGAC which is responsible for the deletion of exon 7 and is associated with SMA.

The term "target sequence" refers to a portion of the target RNA against which the oligonucleotide analog is directed, that is, the sequence to which the oligonucleotide analog will hybridize by Watson-Crick base pairing of a complementary sequence.

The term "targeting sequence" is the sequence in the antisense oligonucleotide analog that is complementary (meaning, in addition, substantially complementary) to the target sequence in the RNA genome. The entire sequence, or only a portion, of the analog compound may be complementary to the target sequence. For example, in an analog having 25 bases, only 12-14 may be targeting sequences. Typically, the targeting sequence is formed of at least 5, 6, 7, 8, 9, 10, 11, 12, 13, 14, 15, 16, 17, 18, 19, 20, 21, 22, or 23 or more contiguous bases in the analog, but may alternatively be formed of non-contiguous sequences that when placed together, e.g., from opposite ends of the analog, constitute sequence that spans the target sequence.

Target and targeting sequences are described as "complementary" to one another when hybridization occurs in an antiparallel configuration. A targeting sequence may have "near" or "substantial" complementarity to the target sequence and still function for the purpose of the present invention, that is, still be "complementary." Preferably, the oligonucleotide analog compounds employed in the present invention have at most one mismatch with the target sequence out of 10 nucleotides, and preferably at most one mismatch out of 20. Alternatively, the antisense oligomers employed have at least 90% sequence homology, and preferably at least 95% sequence homology, with the exemplary targeting sequences as designated herein. For purposes of complementary binding to an RNA target, and as discussed below, a guanine base may be complementary to either an adenine or uracil RNA base.

An oligonucleotide analog "specifically hybridizes" to a target polynucleotide if the oligomer hybridizes to the target under physiological conditions, with a $T_m$ substantially greater than 45° C., preferably at least 50° C., and typically 60° C.-80° C. or higher. Such hybridization preferably corresponds to stringent hybridization conditions. At a given ionic strength and pH, the $T_m$ is the temperature at which 50% of a target sequence hybridizes to a complementary polynucleotide. Again, such hybridization may occur with "near" or "substantial" complementary of the antisense oligomer to the target sequence, as well as with exact complementarity.

A "nuclease-resistant" oligomeric molecule (oligomer) refers to one whose backbone is substantially resistant to nuclease cleavage, in non-hybridized or hybridized form; by common extracellular and intracellular nucleases in the body; that is, the oligomer shows little or no nuclease cleavage under normal nuclease conditions in the body to which the oligomer is exposed.

A "heteroduplex" refers to a duplex between an oligonucleotide analog and the complementary portion of a target RNA. A "nuclease-resistant heteroduplex" refers to a heteroduplex formed by the binding of an antisense oligomer to its complementary target, such that the heteroduplex is substantially resistant to in vivo degradation by intracellular and extracellular nucleases, such as RNAse H, which are capable of cutting double-stranded RNA/RNA or RNA/DNA complexes.

"Treatment" of an individual or a cell is any type of intervention provided as a means to alter the natural course of the individual or cell. Treatment includes, but is not limited to, administration of e.g., a pharmaceutical composition, and may be performed either prophylactically, or subsequent to the initiation of a pathologic event or contact with an etiologic agent. The related term "improved therapeutic outcome" relative to a patient diagnosed as infected with a particular virus, refers to a slowing or diminution in the growth of virus, or viral load, or detectable symptoms associated with infection by that particular virus.

As used herein the term "compound" includes any reagent which is tested using the assays of the invention to determine whether it modulates splice site modulation, e.g., oligonucleotide reagent-mediated splicing modulation. More than one compound, e.g., a plurality of compounds, can be tested at the same time for their ability to modulate splicing in a screening assay.

In one embodiment, test compounds comprise any selection of the group consisting of a small molecule (e.g., an organic molecule having a molecular weight of about 1000 Da or less), a peptide, a polynucleotide, an antibody or biologically active portion thereof, a peptidomimetic, and a non-peptide oligomer.

A gene "involved" in a disorder includes a gene, the normal or aberrant expression or function of which effects or causes a disease or disorder or at least one symptom of said disease or disorder.

Various methodologies of the invention include a step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an oligonucleotide reagent methodology, as described herein. For example, a transcription rate, mRNA level and/or splicing pattern, translation rate, protein level, biological activity, cellular characteristic or property, genotype, phenotype, etc. can be determined prior to introducing an oligonucleotide reagent (e.g., an oligonucleotide, compound, etc., that alters splicing of target pre-mRNA in a sequence-specific manner) of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

As used herein, "nucleobase" (Nu), "base pairing moiety" or "base" are used interchangeably to refer to a purine or pyrimidine base found in native DNA or RNA (uracil, thymine, adenine, cytosine, guanine and hypoxanthine), as well as analogs of the naturally occurring purines and pyrimidines, that confer improved properties, such as binding affinity to the oligonucleotide. Exemplary analogs include hypoxanthine (the base component of the nucleoside inosine); 5-methyl cytosine; C5-propynyl-modified pyrimidines, 9-(aminoethoxy)phenoxazine (G-clamp) and the like.

Further examples of base pairing moieties include, but are not limited to, uracil, thymine, adenine, cytosine, and guanine having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). The modified nucleobases disclosed in Chiu and Rana, RNA, 2003, 9, 1034-1048, Limbach et al. Nucleic Acids Research, 1994, 22, 2183-2196 and Revankar and Rao, Comprehensive Natural Products Chemistry, vol. 7, 313, are also contemplated.

Further examples of base pairing moieties include, but are not limited to, expanded-size nucleobases in which one or more benzene rings has been added. Nucleic base replacements described in the Glen Research catalog (www.glenresearch.com); Krueger A T et al, Acc. Chem. Res., 2007, 40, 141-150; Kool, E T, Acc. Chem. Res., 2002, 35, 936-943; Benner S. A., et al., Nat. Rev. Genet., 2005, 6, 553-543; Romesberg, F. E., et al., Curr. Opin. Chem. Biol., 2003, 7, 723-733; Hirao, I., Curr. Opin. Chem. Biol., 2006, 10, 622-627, are contemplated as useful for the synthesis of the oligomers described herein. Some examples of these expanded-size nucleobases are shown below:

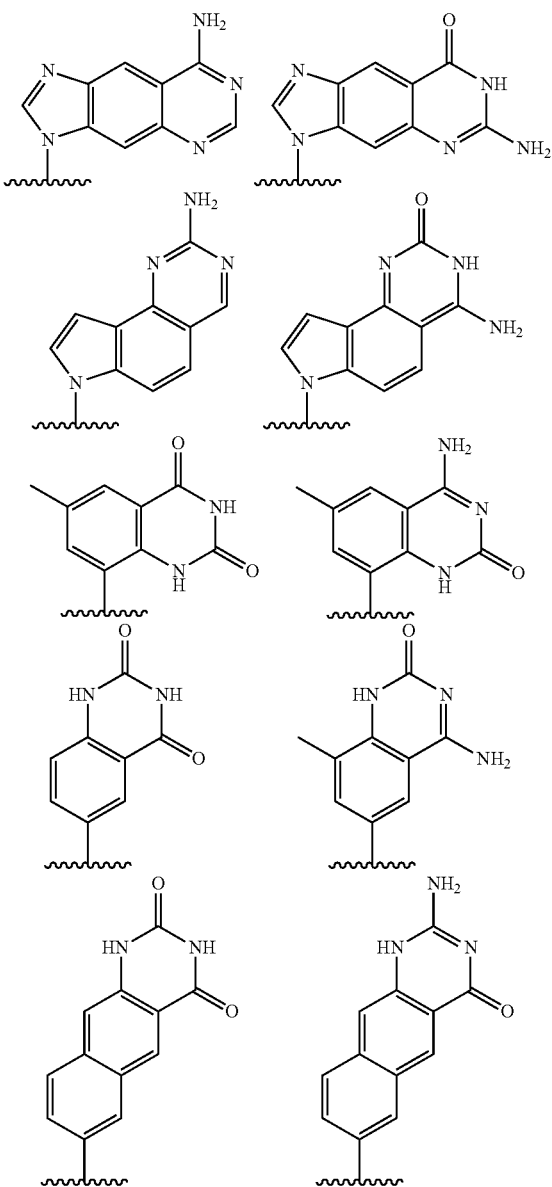

A nucleobase covalently linked to a ribose, sugar analog or morpholino comprises a nucleoside. "Nucleotides" are composed of a nucleoside together with one phosphate group.

The phosphate groups covalently link adjacent nucleotides to one another to form an oligonucleotide. As used herein, an "oligonucleotide" is a linear sequence of nucleotides, or nucleotide analogs, that allows the nucleobase to hybridize to a target sequence in an RNA by Watson-Crick base pairing, to form an oligonucleotide:RNA heteroduplex within the target sequence. The terms "antisense oligonucleotide", "antisense oligomer", "oligomer" and "compound" may be used interchangeably to refer to an oligonucleotide.

A "morpholino oligomer" or "PMO" refers to an oligonucleotide having a backbone which supports a nucleobase capable of hydrogen bonding to typical polynucleotides, wherein the polymer lacks a pentose sugar backbone moiety, but instead contains a morpholino ring. Thus, in a PMO a morpholino ring structure supports a base pairing moiety, to form a sequence of base pairing moieties which is typically designed to hybridize to a selected antisense target in a cell or in a subject being treated. An exemplary "morpholino" oligomer comprises morpholino subunit structures linked together by phosphoramidate or phosphorodiamidate linkages, joining the morpholino nitrogen of one subunit to the 4' exocyclic carbon of an adjacent subunit, each subunit comprising a purine or pyrimidine nucleobase effective to bind, by base-specific hydrogen bonding, to a base in a polynucleotide. Morpholino oligomers (including antisense oligomers) are detailed, for example, in U.S. Pat. Nos. 5,698,685; 5,217,866; 5,142,047; 5,034,506; 5,166,315;

U.S. Pat. Nos. 5,185,444; 5,521,063; 5,506,337 and pending U.S. patent application Ser. No. 12/271,036;

Ser. No. 12/271,040; and PCT publication number WO/2009/064471 all of which are incorporated herein by reference in their entirety.

Within the oligonucleotide structure, the phosphate groups are commonly referred to as forming the "internucleoside linkages" of the oligonucleotide. The naturally occurring internucleoside linkage of RNA and DNA is a 3' to 5' phosphodiester linkage. A "phosphoramidate" group comprises phosphorus having three attached oxygen atoms and one attached nitrogen atom, while a "phosphorodiamidate" group comprises phosphorus having two attached oxygen atoms and two attached nitrogen atoms. In the uncharged or the cationic intersubunit linkages of the PMO and/or PMOX oligomers described herein, one nitrogen is always pendant to the backbone chain. The second nitrogen, in a phosphorodiamidate linkage, is typically the ring nitrogen in a morpholino ring structure.

"PMOX" refers to phosporodiamidate morpholino oligomers having a phosphorus atom with (i) a covalent bond to the nitrogen atom of a morpholino ring and (ii) a second covalent bond to the ring nitrogen of a 4-aminopiperdin-1-yl (i.e. APN) or a derivative of 4-aminopiperdin-1-yl. PMOX oligomers are disclosed in PCT application No.

PCT/US 11/38459 (published as WO/2011/150408), herein incorporated by reference in its entirety. "PMOapn" or "APN" refers to a PMOX oligomer where a phosphorus atom is linked to a morpholino group and to the ring nitrogen of a 4-aminopiperdin-1-yl (i.e. APN).

As used herein, LNA refers to locked nucleic acid oligonucleotides. "LNA" are a member of a class of modifications called bridged nucleic acid (BNA). BNA is characterized by a covalent linkage that locks the conformation of the ribose ring in a C30-endo (northern) sugar pucker. For LNA, the bridge is composed of a methylene between the 2'-0 and the 4'-C positions. LNA enhances backbone preorganization and base stacking to increase hybridization and thermal stability.

An oligonucleotide "specifically hybridizes" to a target polynucleotide if the oligomer hybridizes to the target under physiological conditions, with a Tm substantially greater than 45° C., preferably at least 50° C., and typically 60° C.-80° C. or higher. Such hybridization preferably corresponds to stringent hybridization conditions. At a given ionic strength and pH, the Tm is the temperature at which 50% of a target sequence hybridizes to a complementary polynucleotide. Such hybridization may occur with "near" or "substantial" complementarity of the antisense oligomer to the target sequence, as well as with exact complementarity.

A targeting sequence may have "near" or "substantial" complementarity to the target sequence and still function for the purpose of the present invention, that is, still be "complementary." Preferably, the oligonucleotide analog compounds employed in the present invention have at most one mismatch with the target sequence out of 10 nucleotides, and preferably at most one mismatch out of 20. Alternatively, the antisense oligomers employed have at least 90% sequence homology, and preferably at least 95% sequence homology, with the exemplary targeting sequences as designated herein.

"An electron pair" refers to a valence pair of electrons that are not bonded or shared with other atoms.

Various aspects of the invention are described in further detail in the following subsections.

1. Oligonucleotide Reagents and Splice Site Alteration

The present invention is directed to oligonucleotide reagents, e.g., antisense oligonucleotides, suitable for use in blocking a domain of a target RNA (in exemplary embodiments, a pre-mRNA is blocked, thereby modulating splice site selection of the mRNA splicing machinery) both in vitro and in vivo. In vivo methodologies are useful for both general splice site modulatory purposes as well as in therapeutic applications in which blocking of a target mRNA domain (e.g., enhancement of splice site selection via oligonucleotide reagent-mediated inhibition of a splice site inhibitor domain) is desirable. Oligonucleotide reagents of the invention are of any size and/or chemical composition sufficient to block a target RNA (e.g., pre-mRNA), in particular exemplary embodiments, the reagent is of any size and/or chemical composition sufficient to inhibit the intron 7 long distance interaction site (ISS-N2, 3'ISTL1, LS-1) of SMN2. In exemplary embodiments, the oligonucleotide reagents of the invention are oligonucleotides of between about 5-300 nucleotides (or modified nucleotides), preferably between about 10-100 nucleotides (or modified nucleotides; e.g., ribonucleotides or modified ribonucleotides), for example, between about 15-35, e.g., about 15-20, 20-25, 25-30, 30-35 (31, 32, 33, 34, 35), or 35-40 nucleotides (or modified nucleotides; e.g., ribonucleotides or modified ribonucleotides). Oligonucleotide reagents are preferably sufficiently-complementary to target RNA sequences, in particular embodiments, the short intron 7 novel domain sequence of the SMN2 pre-mRNA. In exemplary embodiments of the invention, oligonucleotide reagents comprise oligonucleotides that contain phosphorothioate and 2'-O-methyl (e.g., 2'-O-methylcytidine, 2'-O-methylpseudouridine, 2'-O-methylguanosine, 2'-O-methyluridine, 2'-O-methyladenosine, 2'-O-methyl) modifications. Many other forms of oligonucleotide modification may be used to generate oligonucleotide reagents of the instant invention, including, for example, locked nucleic acids (oligonucleotides comprising at least one 2'-C,4'-C-oxy-methylene-linked bicyclic ribonucleotide monomer), with one of skill in the art recognizing other modifications capable of rendering an oligonucleotide reagent effective for inducing inclusion of a target exon during RNA splicing (especially as relates to in vivo stability of the oligonucleotide reagents-refer to "Modifications" section below).

An oligonucleotide reagent can be, for example, about 5, 10, 15, 20, 25, 30, 35, 40, 45, or 50 or more nucleotides in length. An oligonucleotide reagent of the invention can be constructed using chemical synthesis and enzymatic ligation reactions using procedures known in the art. For example, an oligonucleotide reagent (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the oligonucleotide reagent can be produced biologically using an expression vector into which a nucleic acid has been sub-cloned, e.g., in an antisense orientation (i.e., RNA transcribed from the inserted nucleic acid will be of an antisense orientation to a target nucleic acid of interest, described further in the following subsection).

The oligonucleotide reagents of the invention are typically administered to a subject or generated in situ such that they hybridize with or bind to cellular pre-mRNA and/or genomic DNA comprising an intron 7 splice silencing sequence identified herein to thereby inhibit exclusion of an exon during splicing. The hybridization can be by conventional nucleotide complementarity to form a stable duplex, or, for example, in the case of an oligonucleotide reagent which binds to DNA duplexes, through specific interactions in the major groove of the double helix. Examples of a route of administration of oligonucleotide reagents of the invention include direct injection at a tissue site or infusion of the antisense nucleic acid into an appropriately-associated body fluid, e.g., cerebrospinal fluid. Alternatively, oligonucleotide reagents can be modified to target selected cells and then administered systemically. For example, for systemic administration, oligonucleotide reagents can be modified such that they specifically bind to receptors or antigens expressed on a selected cell surface, e.g., by linking the oligonucleotide reagents to peptides or antibodies which bind to cell surface receptors or antigens. The oligonucleotide reagents can also be delivered to cells using the vectors described herein. To achieve sufficient intracellular concentrations of the oligonucleotide reagents, vector constructs in which the oligonucleotide reagent is placed under the control of a strong pol II or pol III promoter are preferred.

An oligonucleotide reagent of the invention can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, Nucleic Acids Res. 15:6625-6641). The oligonucleotide reagent can also comprise a 2'-o-methylribonucleotide (Inoue et al., 1987, Nucleic Acids Res. 15:6131-6148) or a chimeric RNA-DNA analogue (Inoue et al., 1987, FEBS Lett. 215:327-330).

In various embodiments, the oligonucleotide reagents of the invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acid molecules (see Hyrup et al., 1996, Bioorganic & Medicinal Chemistry 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) Proc. Natl. Acad. Sci. USA 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra; Perry-O'Keefe et al., 1996, Proc. Natl. Acad. Sci. USA 93:14670-675). In certain embodiments of the instant invention, PNAs can also be generated to target the critical intron 7 sequences identified herein.

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) Nucleic Acids Res. 24(17):3357-63. For example, a DNA chain can be synthesized on a solid support using standard phosphoramidite coupling chemistry and modified nucleoside analogs. Compounds such as 5'-(4-methoxytrityl)amino-5'-deoxythymidine phosphoramidite can be used as a link between the PNA and the 5' end of DNA (Mag et al., 1989, Nucleic Acids Res. 17:5973-88). PNA monomers are then coupled in a step-wise manner to produce a chimeric molecule with a 5' PNA segment and a 3' DNA segment (Finn et al., 1996, Nucleic Acids Res. 24(17): 3357-63). Alternatively, chimeric molecules can be synthesized with a 5' DNA segment and a 3' PNA segment (Peterser et al., 1975, Bioorganic Med. Chem. Lett. 5: 1119-11124).

In certain embodiments of the present invention, a PNA compound that binds to a short intron 7 SMN2 target sequence can be generated additionally to contain one or more charged groups. Such tethering of charged groups to anti-intron 7 SMN2 target compounds can improve the delivery and/or activity of the anti-intron 7 SMN2 compounds of the invention, or also can be used to minimize non-specific effects potentially associated with alternative other formulations of the oligonucleotide reagents of the instant invention. In one embodiment, the oligonucleotide reagents of the invention can be generated as phosphono-PNA molecules (pPNAs), wherein one or more phosphate groups are attached to and/or incorporated into the backbone of the oligonucleotide reagent (refer to Efimov, V., et al. 2003 Nucleosides, Nucleotides & Nucleic Acids 22(5-8): 593-599, incorporated in its entirety herein by reference).

In further embodiments, the oligonucleotide reagents of the invention can be generated as gripNA™ compounds. GripNA™ molecules are a form of negatively charged PNA, which exhibit greater sequence specificity compared to conventional oligonucleotide reagents (e.g., antisense/gene silencing reagents) (refer to "Custom gripNA™ Synthesis Service" handbook (version B2, available through Active-Motif at www.activemotif.com) and to U.S. Pat. No. 6,962, 906, incorporated in its entirety herein by reference).

In additional embodiments, the oligonucleotide reagents of the invention can be generated as steroid-conjugated PNAs. For example, a steroid (e.g., glucocorticoid) dexamethasone can be linked to a PNA of the instant invention, as described in Rebuffat, A. G., et al. (FASEB J. 2002 16(11): 1426-8, the entire contents of which are incorporated herein by reference). The oligonucleotide reagents of the invention can also be produced as tricycle-DNA molecules ((tc)-DNAs) that are splice site-targeted, as described in Ittig, D., et al. (Nucleic Acids Res. 2004 32(1):346-53, the entire contents of which are incorporated herein by reference).

As noted above, the substantially uncharged oligonucleotide may be modified, in accordance with an aspect of the invention, to include charged linkages, e.g., up to about 1 per every 2-5 uncharged linkages, such as about 4-5 per every 10 uncharged linkages. In certain embodiments, optimal improvement in antisense activity may be seen when about 25% of the backbone linkages are cationic. In certain embodiments, enhancement may be seen with a small number e.g., 10-20% cationic linkages, or where the number of cationic linkages are in the range 50-80%, such as about 60%.

In certain embodiments, the antisense compounds can be prepared by stepwise solid-phase synthesis, employing methods detailed in the references cited above, and below with respect to the synthesis of oligonucleotides having a mixture or uncharged and cationic backbone linkages. In some cases, it may be desirable to add additional chemical moieties to the antisense compound, e.g., to enhance pharmacokinetics or to facilitate capture or detection of the compound. Such a moiety may be covalently attached, according to standard synthetic methods. For example, addition of a poly ethylene glycol moiety or other hydrophilic polymer, e.g., one having 1-100 monomeric subunits, may be useful in enhancing solubility.

A reporter moiety, such as fluorescein or a radiolabeled group, may be attached for purposes of detection. Alternatively, the reporter label attached to the oligomer may be a ligand, such as an antigen or biotin, capable of binding a labeled antibody or streptavidin. In selecting a moiety for attachment or modification of an antisense compound, it is generally of course desirable to select chemical compounds of groups that are biocompatible and likely to be tolerated by a subject without undesirable side effects.

As noted above, certain of the antisense compounds (e.g., morpholinos or PMO) can be constructed to contain a selected number of cationic linkages interspersed with uncharged linkages of the type described above. The intersubunit linkages, both uncharged and cationic, preferably are phosphorus-containing linkages, having the structure:

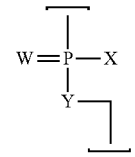

where
W is S or O, and is preferably O,
X=$R_1$, $NR^{11}R^{12}$ or $OR^{16}$,
Y=O or $NR^{17}$,
and each said linkage in the oligomer is selected from:
(a) uncharged linkage (a), where each of $R^{11}$, $R^{12}$, $R^{16}$ and $R^{17}$ is independently selected from hydrogen and $C_1$-$C_6$ alkyl; or
(b1) cationic linkage (b1), where $R_1$ is a moiety of the formula

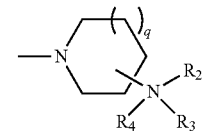

q is 0, 1, 2, 3 or 4;
$R_2$ is selected from the group consisting of hydrogen, $C_1$-$C_5$ alkyl, and a formamidinyl moiety, and
$R_3$ is selected from the group consisting of hydrogen and $C_1$-$C_5$ alkyl, or
$R_2$ and $R_3$ are joined to form a 5-7 membered heterocyclic ring optionally containing an oxygen heteroatom, where the ring may be optionally substituted with a substituent selected from the group consisting of $C_1$-$C_5$ alkyl, phenyl, halogen, and aralkyl;
$R_4$ is selected from the group consisting of null, hydrogen, $C_1$-$C_6$ alkyl and aralkyl;
(b2) cationic linkage (b2), where X=$NR^{11}R^{12}$ and Y=O, and $NR^{11}R^{12}$ represents an optionally substituted piperazino group of the formula

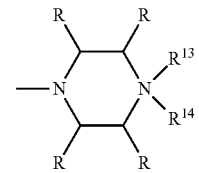

where
each R is independently H or $CH_3$,
$R^{14}$ is H, $CH_3$, or null, and
$R^{13}$ is selected from H, $C_1$-$C_6$ alkyl, 5-7 membered substituted or unsubstituted aryl, heteroaryl or heterocylic ring containing up to 2 heteroatoms selected from the groups consisting of N and O, C(=NH) NH$_2$, Z-L-NRR, Z-L-NHC(=NH) NH$_2$, Z-L-COOH, Z-L-SH, Z-L-PPh$_3$, Z-L-R$^{21}$-R$^{22}$, cholate, and [C(O)CHR'NH]$_m$H, where: Z is C(O) or a direct bond, L is an optional linker up to 18 atoms in length, preferably up to 12 atoms, and more preferably up to 8 atoms in length, having bonds selected from alkyl, alkoxy, and alkylamino, R' is a side chain of a naturally occurring amino acid or a one- or two-carbon homolog thereof, m is 1 to 6, preferably 1 to 4; R$^{21}$ is a 5-7 membered aryl ring, and R$^{22}$ is a 5-7 membered heteroaryl ring containing up to 4 heteroatoms selected from the groups consisting of N and O;

(b3) cationic linkage (b3), where X=NR$^{11}$R$^{12}$ and Y=O, R$^{11}$=H or CH$_3$ and R$^{12}$=LNR$^{13}$R$^{14}$R$^{15}$, where L, R$^{13}$, and R$^{14}$ are as defined above, and R$^{15}$ is H, C$_1$-C$_6$ alkyl, or C$_1$-C$_6$ (alkoxy) alkyl; and (b4) cationic linkage (b4), where Y=NR$^{17}$ and X=OR$^{16}$, and R$^{17}$=LNR$^{13}$R$^{14}$R$^{15}$, where L, R$^{13}$, R$^{14}$ and R$^{15}$ are as defined above, and R$^{16}$ is H or C$_1$-C$_6$ alkyl;

and at least one said linkage is selected from cationic linkages (b1), (b2), (b3) and (b4).

In certain embodiments, an oligomer may include at least two consecutive linkages of type (a) (i.e. uncharged linkages). In further embodiments, at least 5% of the linkages in the oligomer are cationic linkages (i.e. type (b1), (b2), (b3) or (b4)); for example, 10% to 60%, and preferably 20-50% linkages may be cationic linkages.

In one embodiment, at least one linkage is of the type (b1), where, q is 1, R$_2$ and R$_3$ are hydrogen and R$_4$ is null.

In one embodiment, at least one linkage is of type (b2), where, preferably, each R is H, R$^{14}$ is H, CH$_3$, or null, and R$^{13}$ is selected from H, C$_1$-C$_6$ alkyl, C(=NH) NH$_2$, and C(O)-L-NHC(=NH)NH$_2$. The latter two embodiments of R$^{13}$ provide a guanidinyl moiety, either attached directly to the piperazine ring, or pendant to a linker group L, respectively.

For ease of synthesis, the variable Z in R$^{13}$ is preferably C(O) (carbonyl), as shown.

The linker group L, as noted above, contains bonds in its backbone selected from alkyl (e.g., —CH$_2$—CH$_2$—), alkoxy (—C—O—), and alkylamino (e.g., —CH$_2$—NH—), with the proviso that the terminal atoms in L (e.g., those adjacent to carbonyl or nitrogen) are carbon atoms. Although branched linkages (e.g., —CH$_2$—CHCH$_3$—) are possible, the linker is preferably unbranched. In one embodiment, the linker is a hydrocarbon linker. Such a linker may have the structure —(CH$_2$)$_n$—, where n is 1-12, preferably 2-8, and more preferably 2-6.

The morpholino subunits (nucleotide) have the structure:

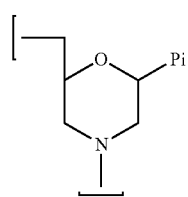

(i)

where Pi is a base-pairing moiety, and the linkages depicted above connect the nitrogen atom of (i) to the 5' carbon of an adjacent subunit. The base-pairing moieties Pi may be the same or different, and are generally designed to provide a sequence which binds to a target nucleic acid.

The use of embodiments of linkage types (b1), (b2) (b3) and (b4) above to link morpholino subunits may be illustrated graphically as follows:

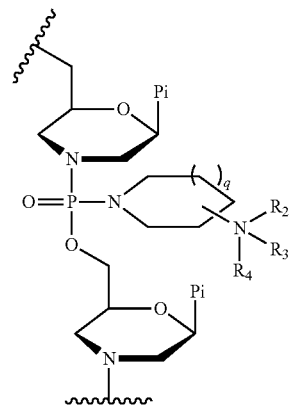

(b1)

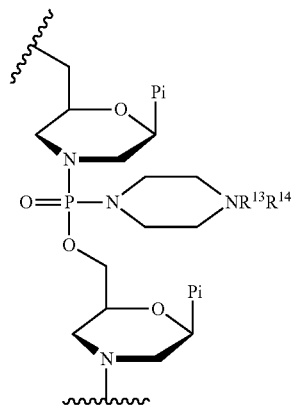

(b2)

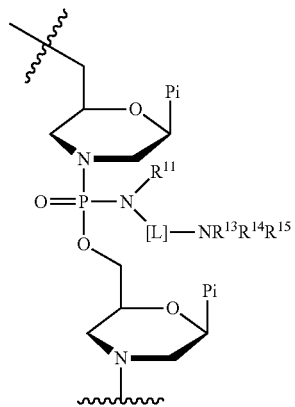

(b4)

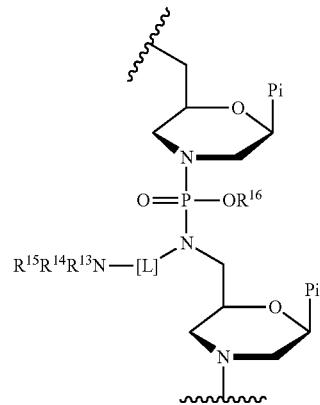

(b3)

Preferably, but not necessarily, all cationic linkages in the oligomer are of the same type; i.e. all of type (b1), all of type (b2), all of type (b3) or all of type (b4).

In further embodiments, the cationic linkages are selected from linkages (b2') and (b2") as shown below, where (b2') is referred to herein as a "Pip" linkage and (b2") is referred to herein as a "GuX" linkage:

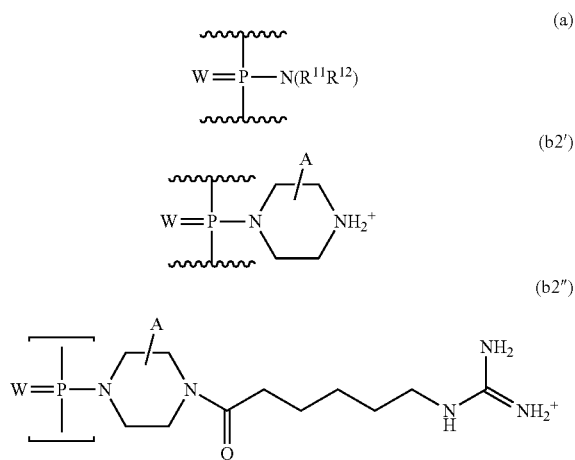

In the structures above, W is S or O, and is preferably O; each of $R^{11}$ and $R^{12}$ is independently selected from hydrogen and $C_1$-$C_6$ alkyl, and is preferably methyl or ethyl; and A represents hydrogen or $C_1$-$C_6$ alkyl on one or more carbon atoms in (b2') and (b2"). Preferably, the ring carbons in the piperazine ring are unsubstituted; however, they may include non-interfering substituents, such as methyl. Preferably, at most one or two carbon atoms is so substituted. In further embodiments, at least 10% of the linkages are of type (b2') or (b2"); for example, 10%-60% and preferably 20% to 50%, of the linkages may be of type (b2') or (b2").

In certain embodiments, the oligomer contains no linkages of the type (b2') above. Alternatively, the oligomer contains no linkages of type (b2) where each R is H, $R^{13}$ is H or $CH_3$, and $R^{14}$ is H, $CH_3$, or null.

The morpholino subunits may also be linked by non-phosphorus-based intersubunit linkages, as described further below, where at least one linkage is modified with a pendant cationic group as described above.

Other oligonucleotide analog linkages which are uncharged in their unmodified state but which could also bear a pendant amine substituent could be used. For example, a 5'-nitrogen atom on a morpholino ring could be employed in a sulfamide linkage or a urea linkage (where phosphorus is replaced with carbon or sulfur, respectively) and modified in a manner analogous to the 5'-nitrogen atom in structure (b4) above.

Oligomers having any number of cationic linkages are provided, including fully cationic-linked oligomers. Preferably, however, the oligomers are partially charged, having, for example, 10%-80%. In preferred embodiments, about 10% to 60%, and preferably 20% to 50% of the linkages are cationic.

In one embodiment, the cationic linkages are interspersed along the backbone. The partially charged oligomers preferably contain at least two consecutive uncharged linkages; that is, the oligomer preferably does not have a strictly alternating pattern along its entire length.

Also considered are oligomers having blocks of cationic linkages and blocks of uncharged linkages; for example, a central block of uncharged linkages may be flanked by blocks of cationic linkages, or vice versa. In one embodiment, the oligomer has approximately equal-length 5', 3' and center regions, and the percentage of cationic linkages in the center region is greater than about 50%, preferably greater than about 70%.

Oligomers for use in antisense applications generally range in length from about 10 to about 40 subunits, more preferably about 10 to 30 subunits, and typically 15-25 bases. For example, an oligomer of the invention having 19-20 subunits, a useful length for an antisense compound, may ideally have two to ten, e.g., four to eight, cationic linkages, and the remainder uncharged linkages. An oligomer having 14-15 subunits may ideally have two to seven, e.g., 3, 4, or 5, cationic linkages and the remainder uncharged linkages.

Each morpholino ring structure supports a base pairing moiety, to form a sequence of base pairing moieties which is typically designed to hybridize to a selected antisense target in a cell or in a subject being treated. The base pairing moiety may be a purine or pyrimidine found in native DNA or RNA (e.g., A, G, C, T or U) or an analog, such as hypoxanthine (the base component of the nucleoside inosine) or 5-methyl cytosine.

As noted above, certain embodiments are directed to oligomers comprising novel intersubunit linkages, including PMO-X oligomers and those having modified terminal groups. In some embodiments, these oligomers have higher affinity for DNA and RNA than do the corresponding unmodified oligomers and demonstrate improved cell delivery, potency, and/or tissue distribution properties compared to oligomers having other intersubunit linkages. In one embodiment, the oligomers comprise at least one intersubunit linkage of type (B) as defined herein. The oligomers may also comprise one or more intersubunit linkages of type (A) as defined herein. The structural features and properties of the various linkage types and oligomers are described in more detail in the following discussion. The synthesis of these and related oligomers is described in U.S. application Ser. No. 13/118,298, which is incorporated by reference in its entirety.

In preferred embodiments, the invention provides for an oligonucleotide having a sequence complementary to the target sequence which is associated with a human disease, and comprises a sequence of nucleotides having a formula:

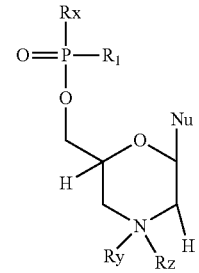

wherein Nu is a nucleobase;
$R_1$ is selected from the group consisting of $R_1'$ and $R_1"$ wherein $R_1'$ is dimethylamino and $R_1"$ is a moiety of the formula

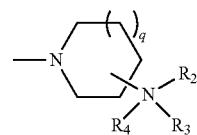

wherein at least one $R_1$ is $R_1"$;
q is 0, 1, 2, 3 or 4;
$R_2$ is selected from the group consisting of hydrogen, $C_1$-$C_5$ alkyl, and a formamidinyl moiety, and $R_3$ is selected from the group consisting of hydrogen and $C_1$-$C_5$ alkyl, or $R_2$ and $R_3$ are joined to form a 5-7 membered heterocyclic ring optionally containing an oxygen hetero atom, where the ring may be optionally substituted with a substituent selected from the group consisting of $C_1$-$C_5$ alkyl, phenyl, halogen, and aralkyl;

$R_4$ is selected from the group consisting of null, hydrogen, a $C_1$-$C_6$ alkyl and aralkyl;

Rx is selected from the group consisting of HO—, a nucleotide, a cell penetrating peptide moiety, and piperazinyl;

Ry is selected from the group consisting of hydrogen, a $C_1$-$C_6$ alkyl, a nucleotide, a peptide moiety, an amino acid, a formamidinyl moiety, and acyl; and, Rz is selected from the group consisting of an null, hydrogen, a $C_1$-$C_6$ alkyl, and acyl; and pharmaceutically acceptable salts thereof.

Nu may be selected from the group consisting of adenine, guanine, thymine, uracil, cytosine, and hypoxanthine. More preferably Nu is thymine or uracil.

About 50-90% of the $R_1$ groups are dimethylamino (i.e., $R_1'$). Most, preferably about 66% (two thirds) of the $R_1$ groups are dimethylamino.

$R_1$ may be selected from the group consisting of

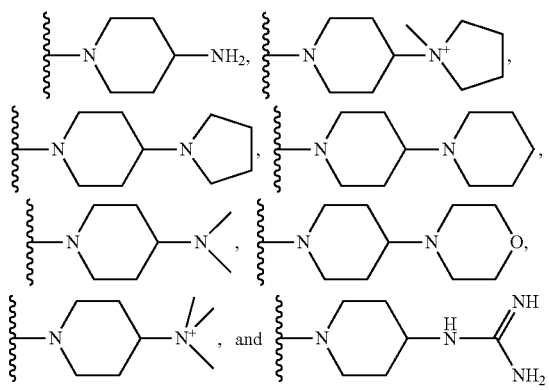

Preferably, at least one nucleotide of the oligonucleotide has the formula:

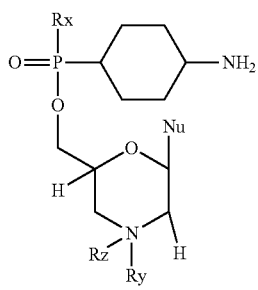

wherein Rx, Ry, Rz, and Nu are as stated above. Most preferably, Nu is thymine or uracil.

Although thymine (T) is the preferred base pairing moiety (Nu or Pi) containing the chemical modifications described above, any base subunit known to a person of skill in the art can be used as the base pairing moiety. Other modifications may be made by methods disclosed in the following published applications each of which is incorporated in its entirety by reference: PMO synthesis—WO2009/064471, PMOplus—WO2008/035127; PPMO—WO2012/150960, and PMO-X—WO2011/150408.

In addition, a recent PCT publication (WO2013/082551) describes the use of a specific class of PMO-X modifications that enhance SMN2 exon 7 inclusion, namely PMO with cationic linkages. The disclosure of which is also hereby incorporated in its entirety by reference.

The preceding forms of modifications can improve the delivery and/or activity of the oligonucleotide reagents of the invention, or also can be used to minimize non-specific effects potentially associated with alternative formulations of the oligonucleotide reagents of the instant invention.

In other embodiments, the oligonucleotide can include other appended groups such as peptides (e.g., for targeting host cell receptors in vivo), or agents facilitating transport across the cell membrane (see, e.g., Letsinger et al., 1989, Proc. Natl. Acad. Sci. USA 86:6553-6556; Lemaitre et al., 1987, Proc. Natl. Acad. Sci. USA 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, Bio/Techniques 6:958-976) or intercalating agents (see, e.g., Zon, 1988, Pharm. Res. 5:539-549). To this end, the oligonucleotide can be conjugated to another molecule, e.g., a peptide, hybridization triggered cross-linking agent, transport agent, hybridization-triggered cleavage agent, etc.

The invention includes bifunctional nucleic acid molecules having at least one region which is complementary to a nucleic acid sequence of the invention, such that the bifunctional nucleic acid recruits stimulatory factors at ISS-N2.

The invention also includes molecular beacon nucleic acid molecules having at least one region which is complementary to a nucleic acid molecule of the invention, such that the molecular beacon is useful for quantitating the presence of the nucleic acid molecule of the invention in a sample. A "molecular beacon" nucleic acid is a nucleic acid molecule comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid molecules are not annealed with one another, fluorescence of the fluorophore is quenched to a lesser degree. Molecular beacon nucleic acid molecules are described, for example, in U.S. Pat. No. 5,876,930.

In another embodiment, oligonucleotide reagents of the invention contain sequences which naturally flank the small intron 7 target sequence (i.e., sequences located at the 5' and 3' ends of the intron 7 critical sequence) in the genomic DNA of an organism. In various embodiments, the isolated oligonucleotide agent can contain about 100 kB, 50 kB, 25 kB, 15 kB, 10 kB, 5 kB, 4 kB, 3 kB, 2 kB, 1 kB, 0.5 kB or 0.1 kB of nucleotide sequences which naturally flank the intron 7 critical target sequence in genomic DNA of the targeted cell. Moreover, an oligonucleotide reagent can be substantially free of other cellular material or culture medium when produced by recombinant techniques, or substantially free of chemical precursors or other chemicals when chemically synthesized.

The target RNA (e.g., pre-mRNA) blocking reaction guided by oligonucleotide reagents of the invention is highly sequence specific. In general, oligonucleotide reagents containing nucleotide sequences perfectly complementary to a portion of the target RNA are preferred for blocking of the target RNA. However, 100% sequence complementarity between the oligonucleotide reagent and the target RNA is not required to practice the present invention. Thus, the invention may tolerate sequence variations that might be expected due to genetic mutation, strain polymorphism, or evolutionary divergence. For example, oligonucleotide reagent sequences with insertions, deletions, and single point mutations relative to the target sequence may also be effective for inhibition. Alternatively, oligonucleotide reagent sequences with nucleotide analog substitutions or insertions can be effective for blocking.

Greater than 70% sequence identity (or complementarity), e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% sequence identity, between the oligonucleotide reagent and the target RNA, e.g., target pre-mRNA, is preferred.

In addition, variants of the short target intron 7 sequence which retain the function of same can be used in the methods of the invention. For example, a series of mutants of may be and tested for their ability to inhibit alternative splicing. In one embodiment, such variant sequences are at least about 95% identical in sequence to SEQ ID NO: 1, 5, 6, 7, 8, or 9 over the entire length of the same. In another embodiment, such variant sequences are at least about 90% identical in the sequence over the entire length of the same.

Sequence identity, including determination of sequence complementarity for nucleic acid sequences, may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM 120 weight residue table, a gap length penalty of 12, and a gap penalty of 4 can be used.

Alternatively, the oligonucleotide reagent may be defined functionally as a nucleotide sequence (or oligonucleotide sequence) a portion of which is capable of hybridizing with the target RNA (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, $Tm° C. = 2(\# \text{ of A+T bases}) + 4(\# \text{ of G+C bases})$. For hybrids between 18 and 49 base pairs in length, $Tm° C. = 81.5 + 16.6(\log 10[Na+]) + 0.41(\% G+C) - (600/N)$, where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference. The length of the identical nucleotide sequences may be at least about 10, 12, 15, 17, 20, 22, 25, 27, 30, 32, 35, 37, 40, 42, 45, 47 or 50 bases.

Modifications

In a preferred aspect, the oligonucleotide reagents (e.g., antisense oligonucleotide analogs) of the present invention are modified to improve stability in serum or growth medium for cell cultures, or otherwise to enhance stability during delivery to SMA subjects and/or cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine can be tolerated without affecting the efficiency of oligonucleotide reagent-induced modulation of splice site selection. For example, the absence of a 2' hydroxyl may significantly enhance the nuclease resistance of the oligonucleotide reagents in tissue culture medium.

In an especially preferred embodiment of the present invention the oligonucleotide reagents, e.g., anti-short intron 7 antisense molecules, may contain at least one modified nucleotide analogue. The nucleotide analogues may be located at positions where the target-specific activity, e.g., the splice site selection modulating activity is not substantially effected, e.g., in a region at the 5'-end and/or the 3'-end of the oligonucleotide (in preferred embodiments, oligoribonucleotide) molecule. Particularly, the ends may be stabilized by incorporating modified nucleotide analogues.

Preferred nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

Also preferred are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine in modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined. Oligonucleotide reagents of the invention also may be modified with chemical moieties (e.g., cholesterol) that improve the in vivo pharmacological properties of the oligonucleotide reagents.

A further preferred oligonucleotide modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—$CH_2$—)$_n$ group bridging the 2' oxygen atom and the 4' carbon atom wherein n is 1 or 2. LNAs and preparation thereof are described in WO 98/39352 and WO 99/14226, the entire contents of which are incorporated by reference herein.

Within the oligonucleotide reagents (e.g., oligoribonucleotides) of the invention, as few as one and as many as all nucleotides of the oligonucleotide can be modified. For example, a 20-mer oligonucleotide reagent (e.g., oligoribonucleotide) of the invention may contain 1, 2, 3, 4, 5, 6, 7, 8, 9, 10, 11, 12, 13, 14, 15, 16, 17, 18, 19 or 20 modified nucleotides. In preferred embodiments, the modified oligonucleotides (e.g., oligoribonucleotides) of the invention will contain as few modified nucleotides as are necessary to achieve a desired level of in vivo stability and/or bioaccessibility while maintaining cost effectiveness.

RNA molecules and oligonucleotide reagents may be produced enzymatically or by partial/total organic synthesis, any modified ribonucleotide can be introduced by in vitro enzymatic or organic synthesis. In one embodiment, an RNA molecule, e.g., oligonucleotide reagent, is prepared chemically. Methods of synthesizing RNA and DNA molecules are known in the art, in particular, the chemical synthesis methods as described in Verma and Eckstein (1998) Annul Rev. Biochem. 67:99-134. RNA can be purified from a mixture by extraction with a solvent or resin, precipitation, electrophoresis, chromatography, or a combination thereof. Alternatively, the RNA may be used with no or a minimum of purification to avoid losses due to sample processing. Alternatively, the RNA molecules, e.g., oligonucleotide reagents, can also be prepared by enzymatic transcription from synthetic DNA templates or from DNA plasmids isolated from recombinant bacteria. Typically, phage RNA polymerases are used such as T7, T3 or SP6 RNA polymerase (Milligan and Uhlenbeck (1989) Methods Enzymol. 180:51-62). The RNA may be dried for storage or dissolved in an aqueous solution. The solution may contain buffers or salts to inhibit annealing, and/or promote stabilization of the single strands.

In preferred embodiments of the invention, the target RNA of an oligonucleotide reagent specifies the amino acid sequence of SMN protein. As used herein, the phrase "specifies the amino acid sequence" of a SMN means that the mRNA sequence is translated into a SMN amino acid sequence according to the rules of the genetic code.

By blocking domains within RNAs (e.g., pre-mRNAs) capable of being translated into such proteins, valuable information regarding the function of said oligonucleotide reagent and/or proteins and therapeutic benefits of said blocking may be obtained.

Splice forms and expression levels of surveyed RNAs and proteins may be assessed by any of a wide variety of well-known methods for detecting splice forms and/or expression of a transcribed nucleic acid or protein. Non-limiting examples of such methods include RT-PCR of spliced forms of RNA followed by size separation of PCR products, nucleic acid hybridization methods e.g., Northern blots and/or use of nucleic acid arrays; nucleic acid amplification methods; immunological methods for detection of proteins; protein purification methods; and protein function or activity assays.

RNA expression levels can be assessed by preparing mRNA/cDNA (i.e. a transcribed polynucleotide) from a cell, tissue or organism, and by hybridizing the mRNA/cDNA with a reference polynucleotide which is a complement of the assayed nucleic acid, or a fragment thereof. cDNA can, optionally, be amplified using any of a variety of polymerase chain reaction or in vitro transcription methods prior to hybridization with the complementary polynucleotide; preferably, it is not amplified. Expression of one or more transcripts can also be detected using quantitative PCR to assess the level of expression of the transcript(s).

In one embodiment, oligonucleotide reagents are synthesized either in vivo, in situ, or in vitro. Endogenous RNA polymerase of the cell may mediate transcription in vivo or in situ, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the oligonucleotide reagent. Production of oligonucleotide reagents may be targeted by specific transcription in an organ, tissue, or cell type; stimulation of an environmental condition (e.g., infection, stress, temperature, chemical inducers); and/or engineering transcription at a developmental stage or age. A transgenic organism that expresses an oligonucleotide reagent from a recombinant construct may be produced by introducing the construct into a zygote, an embryonic stem cell, or another multipotent cell derived from the appropriate organism.

II. Methods of Introducing RNAs, Vectors, and Host Cells

An oligonucleotide reagent construct of the present invention can be delivered to cells ex vivo or in vivo, for example, as an expression plasmid which, when transcribed in the cell, produces RNA, which is complementary to at least a unique portion of the cellular pre-mRNA which encodes an SMN protein.

Alternatively, the oligonucleotide reagent can be an oligonucleotide which is generated ex vivo and which, when introduced into the cell, causes inhibition of expression by hybridizing with the pre-mRNA, mRNA and/or genomic sequences of the SMN2 gene. Such oligonucleotides are preferably modified oligonucleotides, which are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of oligonucleotide (see also U.S. Pat. Nos. 5,176,996, 5,294,564 and 5,256,775, which are herein incorporated by reference).

Oligonucleotide sequences can be introduced into cells as is known in the art. Transfection, electroporation, fusion, liposomes, colloidal polymeric particles and viral and non-viral vectors as well as other means known in the art may be used to deliver the oligonucleotide sequences to the cell. The method of delivery selected will depend at least on the cells to be treated and the location of the cells and will be known to those skilled in the art. Localization can be achieved by liposomes, having specific markers on the surface for directing the liposome, by having injection directly into the tissue containing the target cells, by having depot associated in spatial proximity with the target cells, specific receptor mediated uptake, viral vectors, or the like.

In certain embodiments, ribozymes can be used to deliver oligonucleotide reagents of the invention directed against short intron 7 target sequences (including functional variants of the same) to a necessary site within a given intron. Ribozyme design is an art-recognized process, described, e.g., in U.S. Pat. No. 6,770,633, the entire contents of which are incorporated by reference herein.

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus the RNA may be introduced along with components that perform one or more of the following activities: enhance RNA uptake by the cell, inhibit annealing of single strands, stabilize the single strands, or other-wise increase inhibition of the target gene.

As described supra and in the art, oligonucleotide reagents may be delivered using, e.g., methods involving liposome-mediated uptake, lipid conjugates, polylysine-mediated uptake, nanoparticle-mediated uptake, and receptor-mediated endocytosis, as well as additional non-endocytic modes of delivery, such as microinjection, permeabilization (e.g., streptolysin-O permeabilization, anionic peptide permeabilization), electroporation, and various non-invasive non-endocytic methods of delivery that are known in the art (refer to Dokka and Rojanasakul, Advanced Drug Delivery Reviews 44, 35-49, incorporated in its entirety herein by reference).

Oligonucleotide reagents may be directly introduced into the cell (i.e., intracellularly); or introduced extracellularly into a cavity, interstitial space, into the circulation of an organism, introduced orally, or may be introduced by bathing a cell or organism in a solution containing the RNA using methods known in the art for introducing nucleic acid (e.g., DNA) into cells in vivo. Vascular or extravascular circulation, the blood or lymph system, and the cerebrospinal fluid are sites where the RNA may be introduced.

The present invention also provides vectors comprising an expression control sequence operatively linked to the oligonucleotide sequences of the invention. The present invention further provides host cells, selected from suitable eukaryotic and prokaryotic cells, which are transformed with these vectors as necessary. Such transformed cells allow the study of the function and the regulation of malignancy and the treatment therapy of the present invention.

Vectors are known or can be constructed by those skilled in the art and should contain all expression elements necessary to achieve the desired transcription of the sequences. Other beneficial characteristics can also be contained within the vectors such as mechanisms for recovery of the oligonucleotides in a different form. Phagemids are a specific example of such beneficial vectors because they can be used either as plasmids or as bacteriophage vectors. Examples of other vectors include viruses such as bacteriophages, baculoviruses and retroviruses, DNA viruses, liposomes and other recombination vectors. The vectors can also contain elements for use in either prokaryotic or eukaryotic host systems. One of ordinary skill in the art will know which host systems are compatible with a particular vector. The vectors can be introduced into cells or tissues by any one of a variety of known methods within the art. Such methods can be found generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor, Mich. (1995), Vectors: A Survey of Molecular Cloning Vectors and Their Uses, Butterworths, Boston Mass. (1988) and Gilboa et al., BioTechniques 4:504-512 (1986) and include, for example, stable or transient transfection, lipofection, electroporation and infection with recombinant viral vectors. Viral vectors that have been used for gene therapy protocols include, but are not limited to, retroviruses, other RNA viruses such as poliovirus or Sindbis virus, adenovirus, adeno-associated virus, herpes viruses, SV 40, vaccinia and other DNA viruses. Replication-defective murine retroviral vectors are the most widely utilized gene transfer vectors. Murine leukemia retroviruses are composed of a single strand RNA completed with a nuclear core protein and polymerase (pol) enzymes encased by a protein core (gag) and surrounded by a glycoprotein envelope (env) that determines host range. The genomic structure of retroviruses include gag, pol, and env genes enclosed at the 5' and 3' long terminal repeats (LTRs). Retroviral vector systems exploit the fact that a minimal vector containing the 5' and 3' LTRs and the packaging signal are sufficient to allow vector packaging and infection and integration into target cells providing that the viral structural proteins are supplied in trans in the packaging cell line.

Recombinant methods known in the art can also be used to achieve oligonucleotide reagent-induced inhibition of splicing in a target nucleic acid. For example, vectors containing oligonucleotide reagents can be employed to express, e.g., an antisense oligonucleotide to inhibit splicing of an exon of a targeted pre-mRNA.

Examples of methods to introduced oligonucleotide sequences into cells encompass both non-viral and viral methods, as well as in vivo and ex vivo methods and include, for example:

Direct Injection: Naked DNA can be introduced into cells in vivo by directly injecting the DNA into the cells (see e.g., Acsadi et al. (1991) Nature 332:815-818; Wolff et al. (1990)

Science 247:1465-1468). For example, a delivery apparatus (e.g., a "gene gun") for injecting DNA into cells in vivo can be used. Such an apparatus is commercially available (e.g., from BioRad).

Cationic Lipids: Naked DNA can be introduced into cells in vivo by complexing the DNA with cationic lipids or encapsulating the DNA in cationic liposomes. Examples of suitable cationic lipid formulations include N-[-1-(2,3-dioleoyloxy)propyl]N,N,N-triethylammonium chloride (DOTMA) and a 1:1 molar ratio of 1,2-dimyristyloxy-propyl-3-dimethylhydroxyethylammonium bromide (DMRIE) and dioleoyl phosphatidylethanolamine (DOPE) (see e.g., Logan, J. J. et al. (1995) Gene Therapy 2:38-49; San, H. et al. (1993) Human Gene Therapy 4:781-788).

Receptor-Mediated DNA Uptake: Naked DNA can also be introduced into cells in vivo by complexing the DNA to a cation, such as polylysine, which is coupled to a ligand for a cell-surface receptor (see for example Wu, G. and Wu, C. H. (1988) J. Biol. Chem. 263:14621; Wilson et al. (1992) J. Biol. Chem. 267:963-967; and U.S. Pat. No. 5,166,320). Binding of the DNA-ligand complex to the receptor facilitates uptake of the DNA by receptor-mediated endocytosis. A DNA-ligand complex linked to adenovirus capsids which naturally disrupt endosomes, thereby releasing material into the cytoplasm can be used to avoid degradation of the complex by intracellular lysosomes (see for example Curiel et al. (1991) Proc. Natl. Acad. Sci. USA 88:8850; Cristiano et al. (1993) Proc. Natl. Acad. Sci. USA 90:2122-2126). Carrier mediated gene transfer may also involve the use of lipid-based compounds which are not liposomes. For example, lipofectins and cytofectins are lipid-based positive ions that bind to negatively charged DNA and form a complex that can ferry the DNA across a cell membrane. Another method of carrier mediated gene transfer involves receptor-based endocytosis. In this method, a ligand (specific to a cell surface receptor) is made to form a complex with a gene of interest and then injected into the bloodstream. Target cells that have the cell surface receptor will specifically bind the ligand and transport the ligand-DNA complex into the cell.

Retroviruses: Defective retroviruses are well characterized for use in gene transfer for gene therapy purposes (for a review see Miller, A. D. (1990) Blood 76:271). A recombinant retrovirus can be constructed having a nucleotide sequences of interest incorporated into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include ΨCrip, ΨCre, Ψ2 and ΨAm. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

Adenoviruses: The genome of an adenovirus can be manipulated such that it encodes and expresses a gene product of interest but is inactivated in terms of its ability to replicate in a normal lytic viral life cycle. See for example Berkner et al. (1988) BioTechniques 6:616; Rosenfeld et al. (1991) Science 252:431-434; and Rosenfeld et al. (1992) Cell 68:143-155. Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) Proc. Natl. Acad. Sci. USA 89:6482-6486), hepatocytes (Herz and Gerard (1993) Proc. Natl. Acad. Sci. USA 90:2812-2816) and muscle cells (Quantin et al. (1992) Proc. Natl. Acad. Sci. USA 89:2581-2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) J. Virol. 57:267). Most replication-defective adenoviral vectors currently in use are deleted for all or parts of the viral E1 and E3 genes but retain as much as 80% of the adenoviral genetic material.

Adeno-Associated Viruses: Adeno-associated virus (AAV) is a naturally occurring defective virus that requires another virus, such as an adenovirus or a herpes virus, as a helper virus for efficient replication and a productive life cycle. (For a review see Muzyczka et al. Curr. Topics in Micro. and Immunol. (1992) 158:97-129). It is also one of the few viruses that may integrate its DNA into non-dividing cells, and exhibits a high frequency of stable integration (see for example Flotte et al. (1992) Am. J. Respir. Cell. Mol. Biol. 7:349-356; Samulski et al. (1989) J. Virol. 63:3822-3828; and McLaughlin et al. (1989) J. Virol. 62:1963-1973). Vectors containing as little as 300 base pairs of AAV can be packaged and can integrate. Space for exogenous DNA is limited to about 4.5 kb. An AAV vector such as that described in Tratschin et al. (1985) Mol. Cell. Biol. 5:3251-3260 can be used to introduce DNA into cells. A variety of nucleic acids have been introduced into different cell types using AAV vectors (see for example Hermonat et al. (1984) Proc. Natl. Acad. Sci. USA 81:6466-6470; Tratschin et al. (1985) Mol. Cell. Biol. 4:2072-2081; Wondisford et al.

(1988) Mol. Endocrinol. 2:32-39; Tratschin et al. (1984) J. Virol. 51:611-619; and Flotte et al. (1993) J. Biol. Chem. 268:3781-3790).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product.

In a preferred embodiment, a retroviral expression vector encoding an oligonucleotide of the invention is used in vivo, to thereby inhibit the activity of the short target intron 7 splice inhibiting domain of SMN2, and thus promote SMN2 exon 7 inclusion in vivo. Such retroviral vectors can be prepared according to standard methods known in the art.

A modulatory agent, such as a chemical compound, can be administered to a subject as a pharmaceutical composition. Such compositions typically comprise the modulatory agent and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutical compositions can be prepared as described herein.

Cells targeted or used in the methods of the instant invention are preferably mammalian cells, in particular, human cells. Cells may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands. Neurons and muscle cells (e.g., myocytes, myoblasts, myotubes, myofibers, and the like) are preferred target cells of the invention.

Depending on the particular target gene and the dose of oligonucleotide reagent material delivered, this process may modulate function of the target gene. In exemplary embodiments of the instant invention, exon 7-containing SMN protein production is enhanced in a treated cell, cell extract, organism or patient, with an enhancement of exon 7-containing SMN protein levels of at least about 1.1-, 1.2-, 1.5-, 2-, 3-, 4-, 5-, 7-, 10-, 20-, 100-fold and higher values being exemplary. Enhancement of gene expression refers to the presence (or observable increase) in the level of protein and/or mRNA product from a target RNA. Specificity refers to the ability to act on the target RNA without manifest effects on other genes of the cell. The consequences of modulation of the target RNA can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS).

For oligonucleotide reagent-mediated modulation of an RNA in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentarnycin, hygromycin, kanamycin, lincomycin, methotrexate, phosphinothricin, puromycin, and tetracyclin. Depending on the assay, quantitation of the amount of gene expression allows one to determine a degree of modulation which is greater than 10%, 33%, 50%, 90%, 95% or 99% as compared to a cell not treated according to the present invention. Lower doses of injected material and longer times after administration of oligonucleotide reagents may result in modulation in a smaller fraction of cells (e.g., at least 10%, 20%, 50%, 75%, 90%, or 95% of targeted cells). Quantitation of gene expression in a cell may show similar amounts of modulation at the level of accumulation of target mRNA or translation of target protein. As an example, the efficiency of modulation may be determined by assessing the amount of gene product in the cell; pre-mRNA or mRNA may be detected with a hybridization probe having a nucleotide sequence outside the region used for the oligonucleotide reagent, or translated polypeptide may be detected with an antibody raised against the polypeptide sequence of that region.

The oligonucleotide reagent may be introduced in an amount which allows delivery of at least one copy per cell. Higher doses (e.g., at least 5, 10, 100, 500 or 1000 copies per cell) of material may yield more effective modulation; lower doses may also be useful for specific applications.

III. Methods of Treatment

The present invention provides for both prophylactic and therapeutic methods of treating a subject at risk of (or susceptible to) a disorder or having a disorder associated with aberrant or unwanted target gene expression or activity (e.g., in exemplary embodiments, underexpression of SMN protein). "Treatment", or "treating" as used herein, is defined as the application or administration of a therapeutic agent (e.g., an oligonucleotide reagent (e.g., oligoribonucleotide) or vector or transgene encoding same, a small molecule short intron 7 splice inhibiting blocking agent, etc.) to a patient, or application or administration of a therapeutic agent to an isolated tissue or cells (including fetal cells) from a patient, who has a disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the target gene molecules of the present invention or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant or unwanted target gene expression or activity, by administering to the subject a therapeutic agent (e.g., an oligonucleotide reagent (e.g., oligoribonucleotide) or vector or transgene encoding same, a small molecule short intron 7 splice inhibiting blocking agent, etc.). Subjects at risk for a disease which is caused or contributed to by aberrant or unwanted target gene expression or activity can be identified by, for example, any or a combination of diagnostic or prognostic assays as described herein. Administration of a prophylactic agent can occur prior to the manifestation of symptoms characteristic of the target gene aberrancy, such that a disease or disorder is prevented or, alternatively, delayed in its progression. Depending on the type of target gene aberrancy, for example, a target gene, target gene agonist or target gene antagonist agent can be used for treating the subject. The appropriate agent can be determined based on screening assays described herein.

2. Therapeutic Methods

Another aspect of the invention pertains to methods of modulating target gene expression, protein expression or activity for therapeutic purposes. Accordingly, in an exemplary embodiment, the modulatory method of the invention involves contacting a cell capable of expressing target gene with a therapeutic agent (e.g., an oligonucleotide reagent (e.g., oligoribonucleotide) or vector or transgene encoding same, a small molecule short intron7 target blocking agent, etc.) that is specific for the target gene or protein (e.g., is specific for the pre-mRNA encoded by said gene and/or specifying the amino acid sequence of said protein) such that expression or one or more of the activities of target protein is modulated. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a target gene polypeptide or nucleic acid molecule. Modulation of target gene activity is desirable in situations in which target gene is abnormally unregulated and/or in which altered target gene activity is likely to have a beneficial effect.

In one embodiment, cells from a subject having spinal muscular atrophy are contacted with an oligonucleotide reagent of the invention to inhibit splicing of the SMN2 exon 7. Exemplary oligonucleotide reagents include sequences complementary to the short intron 7 target sequence and variants thereof (e.g., as shown herein). In another embodiment, cells from a subject having another disorder that would benefit from inhibition of alternative splicing are contacted with an oligonucleotide reagent of the invention. Target sequences related to the target sequences disclosed herein are present in human intronic sequences. For example, there is a sequence partially homologous to the ISS-N1 sequence located in human CFTR (intron 10). Additional exemplary genes that can be targeted by oligonucleotide reagents of the invention (e.g., sequences complementary to the target sequences and variants thereof (e.g., as shown herein) include, but are not limited to, CFTR, FAS, Caspases, Diablo, NF1, Bcl2, Tau, ApoA-11, p53, Tra2, Cox-1 and Survivin.

3. Delivery of Oligonucleotide Reagents to the Nervous System

The oligonucleotide reagents of the invention can be delivered to the nervous system of a subject by any art-recognized method. For example, peripheral blood injection of the oligonucleotide reagents of the invention can be used to deliver said reagents to peripheral neurons via diffusive and/or active means. Alternatively, the oligonucleotide reagents of the invention can be modified to promote crossing of the blood-brain-barrier (BBB) to achieve delivery of said reagents to neuronal cells of the central nervous system (CNS). Specific recent advancements in oligonucleotide reagent technology and delivery strategies have broadened the scope of oligonucleotide reagent usage for neuronal disorders (Forte, A., et al. 2005. Curr. Drug Targets 6:21-29; Jaeger, L. B., and W. A. Banks. 2005. Methods Mol. Med. 106:237-251; Vinogradov, S. V., et al. 2004. Bioconjug. Chem. 5:50-60; the preceding are incorporated herein in their entirety by reference). For example, the oligonucleotide reagents of the invention can be synthesized to comprise phosphorothioate oligodeoxynucleotides (P-ODN) directed against the short intron 7 target sequence, or may be generated as peptide nucleic acid (PNA) compounds. P-ODN and PNA reagents have each been identified to cross the BBB (Jaeger, L. B., and W. A. Banks. 2005. Methods Mol. Med. 106:237-251). Treatment of a subject with, e.g., a vasoactive agent, has also been described to promote transport across the BBB (ibid.). Tethering of the oligonucleotide reagents of the invention to agents that are actively transported across the BBB may also be used as a delivery mechanism.

In certain embodiments, the oligonucleotide reagents of the invention can be delivered by transdermal methods (e.g., via incorporation of the oligonucleotide reagent(s) of the invention into, e.g., emulsions, with such oligonucleotide reagents optionally packaged into liposomes). Such transdermal and emulsion/liposome-mediated methods of delivery are described for delivery of antisense oligonucleotides in the art, e.g., in U.S. Pat. No. 6,965,025, the contents of which are incorporated in their entirety by reference herein.

The oligonucleotide reagents of the invention may also be delivered via an implantable device (e.g., pacemaker or other such implantable device). Design of such a device is an art-recognized process, with, e.g., synthetic implant design described in, e.g., U.S. Pat. No. 6,969,400, the contents of which are incorporated in their entirety by reference herein.

4. Pharmacogenomics

The therapeutic agents (e.g., an oligonucleotide reagent or vector or transgene encoding same) of the invention can be administered to individuals to treat (prophylactically or therapeutically) disorders associated with aberrant or unwanted target gene activity. In conjunction with such treatment, pharmacogenomics (i.e., the study of the relationship between an individual's genotype and that individual's response to a foreign compound or drug) may be considered.

Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a therapeutic agent as well as tailoring the dosage and/or therapeutic regimen of treatment with a therapeutic agent.

5. Pharmaceutical Compositions

The invention pertains to uses of the above-described agents for therapeutic treatments as described infra. Accordingly, the modulators of the present invention (e.g., oligonucleotides, small molecules and the like) can be incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

This invention is further illustrated by the following examples which should not be construed as limiting. The contents of all references, patents and published patent applications cited throughout this application are incorporated herein by reference.

EXAMPLES

Example 1

Introduction

Alternative splicing is modulated by combinatorial control exerted by overlapping linear motifs called exonic or intronic splicing enhancers (ESEs or ISEs) and silencers (ESSs or ISSs) (1-3). While methods to define linear splicing motifs continue to evolve (4-6), there is a growing appreciation of the role of RNA structure in regulation of alternative splicing (7-10). RNA secondary structure folding occurs on a microsecond time scale (11,12), a rate that is faster than polymerase II-mediated transcription elongation, which is ~100 nucleotides (nts) per second (13). Therefore, terminal stem-loops (TSLs), which represent the most prevalent form of local structures, are formed as soon as the nascent transcript emerges from the polymerase. Multiple studies confirm the role of TSLs in modulation of alternative splicing (14-18). Evidence suggests that internal stems formed by long-range interactions affect pre-mRNA splicing as well (8, 19, 20). However, functional validation of such interactions as critical checkpoints for splicing regulation in the context of a human disease has not been done.

Figure 1A:
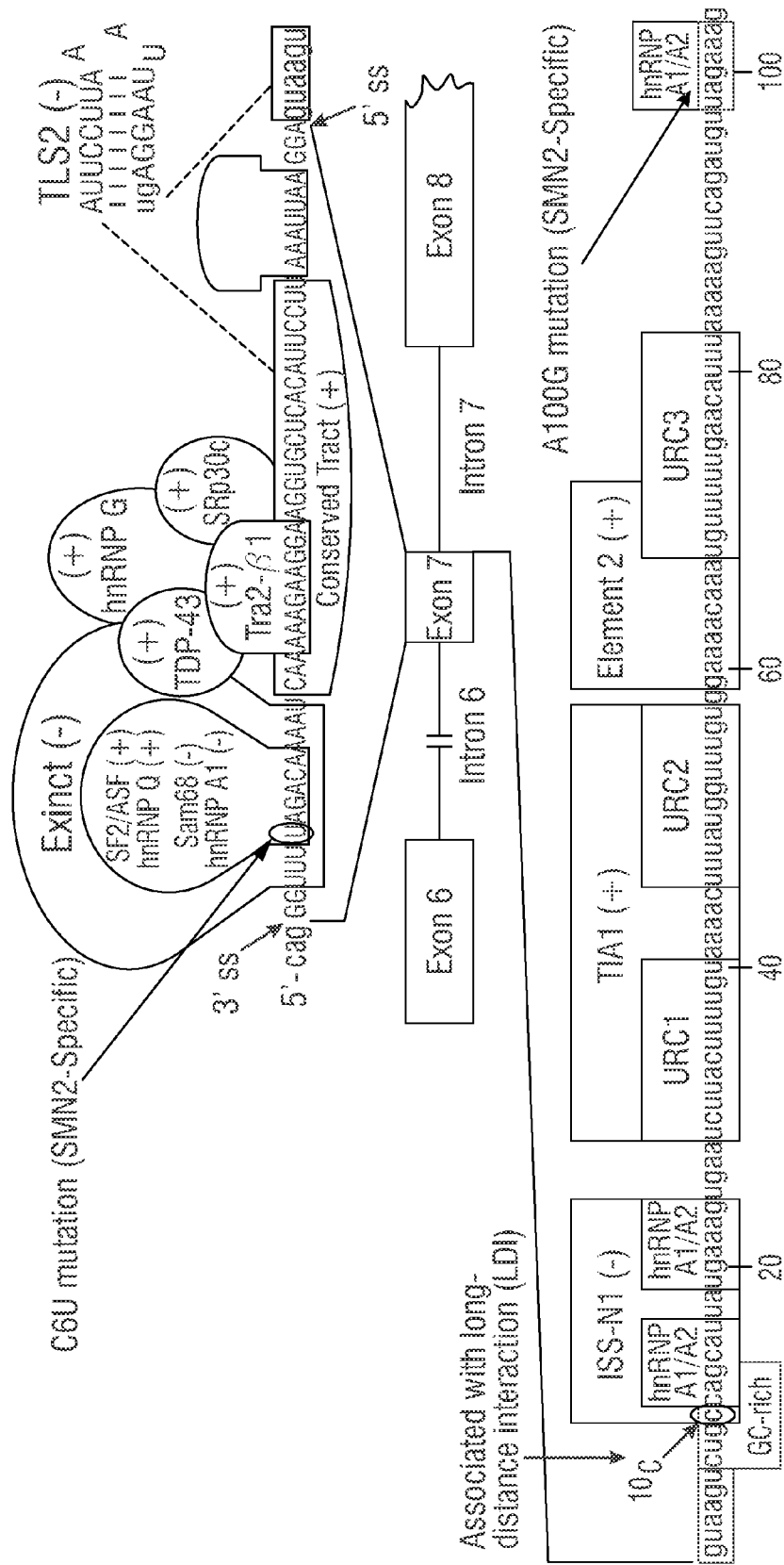
FIGS. 1A and 1B are schematics of SMN2 exon 7. An account of transacting factors and cis-elements including RNA secondary structure that regulate SMN2 exon 7 splicing. (A) Diagrammatic representation of cis-elements located within exon 7 and the first 103 nucleotides of intron 7 of SMN2. The sequence of SMN2 exon 7 and adjacent intron 7 are given (SEQ ID NOs: 54, 55). Numbering of nucleotides starts from the beginning of intron 7. Positive cis-elements/transacting factors that promote exon 7 inclusion and negative cis-elements/transacting factors that promote exon 7 skipping are indicated by (+) and (−), respectively. Extinct, Conserved tract and 3'-Cluster were identified by in vivo selection of the entire exon 7 (33). TSL2 structure sequesters the 5' ss of exon 7 (16). Element 2 and binding sites for SF2/ASF, hnRNP A1/A2, Sam68, hnRNP Q, Tra2-β1, TDP-43, hnRNP G and SRp30c were described by others (refs. in 32). TIA1 was shown to bind to intron 7 U-rich Clusters (URCs) 1 and 2 and promote exon 7 inclusion (31). ISS-N1, along with an overlapping GC-rich sequence and the $^{10}$C involved in LDI all contribute towards exon 7 skipping (refs. in 32). (B) Schematic representation of RNA secondary structure of SMN2 intron 7. The schematic is based on chemical structure probing performed in this study (see FIG. 6). A defining feature of RNA the secondary structure of SMN2 intron 7 is the presence of the three adjacent internal stems formed by LDIs (ISTLs). The adjacent 3'-strands of ISTL1, ISTL2 and ISTL3 constitute ISS-N2, a novel target for splicing correction in SMA (described later) (SEQ ID NO: 12). Of note, $^{10}$C is locked in ISTL1 and base pairs with the $290^{th}$ position of SMN2 intron 7. A sequence identical to LS-1 has been shaded. Descriptions of abbreviations are given in Table 1.

Humans have two nearly identical copies of the Survival Motor Neuron (SMN) gene: SMN1 and SMN2 (21). The two SMN genes code for identical proteins; however, SMN2 predominantly generates a shorter transcript due to skipping of exon 7, which produces a truncated, unstable SMN (22,23). The inability of SMN2 to compensate for the loss of SMN1 results in spinal muscular atrophy (SMA), a debilitating childhood disease (24). SMN2 exon 7 skipping is caused by a C-to-T mutation at the $6^{th}$ position (C6U in transcript) of exon 7 (25). C6U weakens the 3' splice site (3' ss) due to the loss of an ESE associated with SF2/ASF and/or gain of an ESS associated with hnRNP A1 (FIG. 1; 26,27). Another SMN2-specific mutation at the $100^{th}$ position of intron 7 creates an ISS associated with hnRNP A1 (FIG. 1; 28). Sam68 and PTB1 are two additional inhibitory proteins implicated in SMN2 exon 7 skipping (FIG. 1; 29-31). Several positive factors, including hnRNP G, hnRNP Q, SRp30c, TDP43, TIA1 and Tra2-β1 stimulate SMN2 exon 7 inclusion (FIG. 1; 32).

An early in vivo selection study to unravel the position-specific role of residues within exon 7 revealed the suboptimal nature of its 5' ss (33). Subsequent studies uncovered a series of negative cis-elements in the vicinity of the 5' ss of exon 7, including the intronic splicing silencer N1 (ISS-N1), a stem-loop structure (TSL2) and a GC-rich sequence that partially overlaps with ISS-N1 (FIG. 1; 16,34,35). The discovery of ISS-N1 was particularly significant as it served as the first example in which deletion of an inhibitory intronic element fully restored SMN2 exon 7 inclusion even in the absence of the critical positive regulatory elements within exon 7 (34). Further, sequestration of ISS-N1 by an antisense oligonucleotide (ASO) corrected SMN2 exon 7 splicing and restored high levels of SMN protein in SMA patient cells. Of note, different mechanisms may account for the strong stimulatory effect of ISS-N1 deletion and ASO-mediated ISS-N1 sequestration. For example, deletion of ISS-N1 brings a TIA1-binding site (a positive cis-element) very close to the 5' ss of exon 7 (31), whereas, an ASO-mediated sequestration of ISS-N1 destabilizes an inhibitory structure close to the 5' ss of exon 7 (this study). Following the discovery of ISS-N1 in 2006, an unprecedented number of in vivo studies independently confirmed the therapeutic efficacy of ISS-N1-targeting ASOs (36-39).

We have previously reported a unique long-distance interaction (LDI) between a cytosine residue at the $10^{th}$ position ($^{10}$C) of SMN2 intron 7 and a downstream intronic sequence separated from $^{10}$C by hundreds of nucleotides (40). The most surprising aspect of this discovery was the position-specific role of $^{10}$C. An ASO (F14) that sequestered the first fourteen residues (including $^{10}$C) of ISS-N1 promoted SMN2 exon 7 inclusion, while another ASO (L14) that sequestered the last fourteen residues (excluding $^{10}$C) of ISS-N1 increased SMN2 exon 7 skipping. Deletion or substitution of $^{10}$C fully abrogated the inhibitory effect of L14, confirming that the negative impact of this ASO is associated exclusively with the unsequestered $^{10}$C. The first indirect support linking $^{10}$C to a LDI came from experiments in a heterologous system, where the negative effect of L14 on exon 7 splicing was not recapitulated despite the system harboring the entire SMN2 exon 7 and flanking intronic sequences, including ISS-N1 (40). Subsequent experiments revealed that $^{10}$C engages in a LDI with downstream sequences within the 3' portion of SMN2 intron 7. Indeed, deletion of these sequences transformed L14 into a stimulatory ASO (40). These findings offered a unique opportunity to uncover the molecular basis of a rare LDI in the context of a leading genetic disease.

Here we report the mechanistic basis of the $^{10}$C-mediated LDI, which we found to be facilitated by an intricate arrangement of sequence and structural motifs within SMN2 intron 7. Using deletions and site-specific mutations combined with the chemical structure probing, we demonstrate that the $^{10}$C-mediated LDI is linked to a unique RNA structure. We also show that the inhibitory effect of the $^{10}$C-mediated LDI is independent of the widely expressed hnRNP A1/A2B1 and PTB1 proteins that were previously implicated in skipping of SMN2 exon 7. These results provide the first example in which a deep intronic sequence associated with a RNA structure supported by a unique LDI modulates alternative splicing in a major genetic disease. In addition, we demonstrate that a RNA structure within an intron could serve as an effective target for an ASO-mediated splicing correction in SMA.

Materials and Methods

Minigenes and Antisense Oligonucleotides

SMN2 mutant minigenes were generated by PCR using a strategy described earlier (33). The identity of novel minigenes was verified by sequencing. All primers for cloning were from Integrated DNA Technologies. Reagents for PCR and cloning were from New England Biolabs. RNA ASOs were synthesized by Dharmacon Inc., and incorporated a phosphorothioate backbone and 2'-O-methyl modifications at each base (Table 2; 34).

Cell Culture

All tissue culture media and supplies were purchased from Life Technologies. Human cervical adenocarcinoma (HeLa) cells obtained from the American Type Culture Collection were cultured in Dulbecco's modified Eagle's medium supplemented with 10% fetal bovine serum (FBS). Primary patient fibroblasts from an SMA type I patient (repository number GM03813) were obtained from Coriell Cell Repositories. These cells were grown in minimal essential medium (MEM, catalog #10370) supplemented with 1× GlutaMAX-I and 15% FBS.

Cell Transfection

Transient transfections of cells with plasmid DNA and/or antisense oligonucleotides were performed using Lipofectamine-2000 (Life Technologies) following the manufacturer's recommendations. HeLa cells were plated at a density of ~1.1×10$^5$ cells per well of 24-well plates. The next day, cells were cotransfected with 0.1 μg of a given minigene and 50 nM of an ASO of interest. The total amount of transfected nucleic acid was maintained constant (0.8 μg) by adding the control ASO (Table 2; 40). The growth medium was changed six hours post-transfection. In the case of primary fibroblasts, depending on the amount of cells needed for the analysis, GM03813 cells were plated in either a 6-well plate or 100-mm dishes at a density of 1.3×10$^5$ cells per well or 9×10$^5$ cells per dish, respectively. The next day, GM03813 cells were transfected with ASOs. ASO concentrations varied and are indicated in the legend of FIG. 11. The growth medium was replaced six hours after transfection. For isolation of total RNA only, HeLa and GM03813 cells were lysed directly in tissue culture plates ~24 h post-transfection using Trizol Reagent (Life Technologies). For simultaneous RNA and protein analysis, transfected GM03813 cells were collected 48 h post-transfection by scraping. One-third of the cells were taken for RNA isolation with Trizol, and the rest were used for protein isolation and Western blotting.

ASO Transfection Combined with Protein Knockdown

Proteins of interest were knocked down using siRNAs (ON-TARGETplus SMART pool; Dharmacon Inc.). An ON-TARGETplus nontargeting pool served as a control siRNA. To knock down proteins of interest, HeLa cells were reverse transfected with siRNAs twice with an interval of ~48 h. For each siRNA transfection, a siRNA-Lipofectamine-2000 complex was prepared following the manufacturer's suggestions, combined with HeLa cell suspension containing ~1×10$^6$ cells in a total volume of 2 ml, and then the cells were seeded in one well of a 6-well plate. For simultaneous transfection of siRNAs against hnRNP A1 and hnRNPA2B1, two wells were seeded, since simultaneous depletion of hnRNP A1 and hnRNP A2B1 proteins had a negative effect on cell survival. For the first transfection, the final concentration for individual siRNAs was 80 nM and 40 nM each when siRNAs against hnRNP A1 and hnRNP A2B1 were transfected together. The next day, the transfected cells were trypsinized and transferred to 60-mm dishes. The second reverse transfection of HeLa cells with siRNAs were performed ~48 h after the first one essentially as described above, except that the siRNA concentration was increased to 100 nM for individual siRNAs and to 50 nM each when siRNAs against hnRNP A1 and hnRNP A2B1 were transfected together. Twenty-four hours after the second siRNA transfection, HeLa cells were trypsinized and seeded in 24-well plates to be transfected with the ASOs of interest the next day. The remaining cells were returned to 6-well plates to be collected ~22 h later for making cell lysates to monitor the efficiency of protein knockdown. Three wells of a 24-well plate were seeded for each siRNA transfection. The density of plating per well was ~1.4×10$^5$ cells for HeLa transfected with a control siRNA, ~1.6×10$^5$ cells for HeLa transfected with individual siRNA against hnRNPA1, hnRNP A2B1 or PTB1 and ~1.7×10$^5$ cells for HeLa cotransfected with siRNAs against hnRNP A1 and hnRNP A2B1. HeLa cells seeded in 24-well plates were transfected ~24 h later with 100 nM ASO of interest along with corresponding siRNA employing Lipofectamine-2000 followed by cell lysis ~24 hours later and isolation of total RNA.

In Vivo Splicing Assay

Total RNA was isolated using Trizol Reagent following manufacturer's instructions. cDNA was generated as described previously (40). Minigene-specific spliced products were amplified using Taq DNA polymerase and the P1 and P2 primer pair (Table 3; 34). For PCR amplification of endogenous SMN, either P25 and P31 or N-24 and P2 primer pairs were used (Table 3; 31,34). Cloning and sequencing confirmed the identity of splice variants amplified by RT-PCR (33). To accurately determine the relative abundance of splice variants, reduced cycles of PCR reactions were performed either in the presence of a trace amount of [α-$^{32}$P] dATP (3000 Ci/mmole, Perkin-Elmer Life Sciences) or with the P2 primer labeled at the 5'-end with $^{32}$P. To distinguish SMN1 and SMN2 splice isoforms, PCR products amplified with primers P25 and P31 were subjected to overnight DdeI digestion, followed by phenol: chloroform extraction and ethanol precipitation (31). Quantification and analysis of splice products were performed using a FPL-5000 Image Reader and Multi Gauge software (Fuji Photo Film Inc). Results were confirmed by at least three independent experiments. The percentage values of exon 7 skipping given in figures were calculated for the sown representative gel.

Western Blot Analysis

HeLa cells (~3×10$^5$) were harvested and cell lysates were prepared similarly as described before (34). One-seventh of each lysate was used for one blot. Whole-cell extracts from GM03813 cells were prepared as described previously (41). Protein concentrations were determined using the Bio-Rad Protein Assay Dye Reagent Concentrate (Bio-Rad). Protein samples were resolved on 8% or 10% SDS-polyacrylamide gels and transferred onto polyvinylidene fluoride membrane (Bio Trace PVDF, Pall Life Sciences). The following primary and secondary antibodies were used for Western blot analysis: mouse monoclonal anti-PTB1 (Abcam), mouse monoclonal anti-hnRNP A1, clone 9H10 (Abcam), mouse monoclonal anti-hnRNP A2B1, clone DP3B3 (Abcam), mouse monoclonal anti-SMN, clone 8 (BD Transduction Laboratories), mouse monoclonal anti-Gemin 2, clone 2E17 (Sigma), mouse monoclonal anti-GAPDH, clone 6C5 (Abcam), rabbit polyclonal anti-Actin (Sigma-Aldrich), goat anti-mouse horseradish peroxidase-conjugated antibody (Jackson Immunoresearch) and donkey anti-rabbit horseradish peroxidase-conjugated antibody (GE Healthcare). Immunoreactive proteins were visualized with Clarity Western ECL substrate (Bio-Rad), SuperSignal West Dura Extended Duration Substrate or SuperSignal West Femto Maximum Sensitivity Substrate (Thermo Scientific). Membranes were stripped using Restore Western Blot Stripping Buffer (Thermo Scientific) and re-probed for proteins of interest. The membranes were scanned using the UVP BioSpectrum AC Imaging System (UVP). Results were confirmed by at least three independent experiments.

RNA Structure Probing

RNA secondary structure was probed using Selective 2'-Hydroxyl Acylation analyzed by Primer Extension (SHAPE) following recommendations provided in (42). 1-methyl-7-nitroisatoic anhydride (1M7) was synthesized as described (43). RNA substrates for structure probing were in vitro transcribed using T7 MEGAshortscript kit (Ambion) following the manufacturer's recommendations. Templates for T7 in vitro transcription were prepared as follows. Sequences that contained the last 17 nucleotides of exon 7 and all of intron 7 were amplified by PCR using the primer pair 5'T7-Xba-2 (5'-ATA TAT TCT AGA TAA TAC GAC TCA CTA TAG GGA TTC CTT AAA TTA AGG AGT AAG TC-3' (SEQ ID NO:52)) and 3'Hind-2 (5'-ATA TAT AAG CTT TTC TGC AAA TGA GAA ATT AGA ACC AG-3' (SEQ ID NO:53)) and either wild type SMN2ΔI6 minigene (33) or ISTL1-M4 mutant (this study) as a template. The resulting PCR fragments were digested with XbaI and HindIII and cloned into the pUC19 vector to generate the plasmid constructs T7-TSL2-In7 and T7-TSL2-ISTL1-M4. The plasmids were linearized with HindIII and used as templates for RNAs synthesized in an overnight T7 transcription reaction. The DNA template was removed by DNase treatment followed by phenol:chloroform extraction and RNA was recovered by ethanol precipitation, dissolved in water and further purified by centrifugation through a gel-filtration Micro Bio-spin P-30 Chromatography column (Bio-Rad).

Primers used for extension reactions are listed in Table 4. Extension primers (60 pmol each) were 5'end-labeled with [γ-$^{32}$P]ATP (6000 Ci/mmol) and T4 polynucleotide kinase (New England Biolabs), phenol:chloroform extracted, centrifuged through a gel-filtration Micro Bio-spin P-30 Chromatography column to remove unincorporated [γ-$^{32}$P]ATP. The eluted sample was evaporated under vacuum to reduce the volume to ~5 μl to which 10 μl of formamide gel-loading buffer (Ambion) was added. End-labeled primers were then purified on denaturing 15% polyacrylamide gels by the "crush and soak" method (16). The elution was done overnight at 37° C. Primers were ethanol precipitated, dissolved in 70 μl of water and centrifuged through a Micro Bio-spin P-30 Chromatography column. Of note, a total of 1 μl of recovered primer was used for each 5 μl of primer extension reaction.

Prior to structure probing RNA was refolded as follows. Sixteen pmol RNA with the control ASO (40) or ASO of interest was heated to 95° C. for 2 min in 30 mM Tris-HCl (pH 8.0) and snap-cooled on ice. The amount of ASO used was 160 pmol for F14, L14 and ASO-M. The amount was increased to 204 pmol for ASO-D. Folding was performed in a total volume of 72 μl (100 mM Tris-HCl, pH 8.0, 100 mM NaCl and 10 mM MgCl$_2$) at 37° C. for 20 min after which time the reaction was split into two aliquots (36 μl each) and the incubation continued for another 10 min. 4 μl of either 1M7 (100 mM in DMSO) or DMSO (control) were then added to the 36 μl of RNA folding reaction and the mixture was incubated at 37° C. for 2 min. Each modification reaction was then transferred to a tube containing 158 μl of water, 20 μl of potassium acetate (3M, pH 5.5), 0.8 μl of 500 mM EDTA (pH 8.0) and 1.2 μl of GlycoBlue (15 mg/ml, Ambion). RNA was recovered by ethanol precipitation and dissolved in 10 μl of water. 1M7 modification sites were analyzed by primer extension using SuperScript III RTase (42). Briefly, modified RNA (1 μl) was mixed with 5'-end-labeled primer of interest (1 μl), 1 μl of water, 0.25 μl of 5×RT buffer and 0.25 μl of dNTP mixture (10 mM each). The mixture was heated to 65° C. for 5 min and snap-cooled on ice. One μl of RT mix (4 parts 5×RT buffer and 1 part 0.1 M DTT) and 0.5 μl of SuperScript III RTase (100 U/μl) were then added to the primer extension reaction. The reaction was incubated for 2 min at 45° C. and 30 min at 55° C. To prevent RTase falloffs at positions 292 and 293 routinely observed with extension primer#17 and primer#315, ASO-D (5 pmol) was added to the reaction mixture prior to the denaturation step. Denaturation itself was performed at 95° C. for 2 min instead of at 65° C. for 5 min. Also, prior to RTase addition, the reaction was incubated for 5 min at 45° C. to allow ASO-D to invade the ISTL1 structure and release its 3' strand for primer extension. To generate sequencing ladders, primer extension reactions were performed as described above except that 0.5 μl of a given ddNTP (10 mM) was added per 5 μl reaction and 40 ng of the wild type RNA substrate was used as a template. For the primer extension step, the reactions were incubated for 2 min at 45° C. and 15 min at 55° C. To degrade RNA after completion of primer extension, 0.5 μl 2M NaOH was added to the reaction and the mixture was heated at 95° C. for 5 min. The mixture was then allowed to cool to room temperature and 1 μl of 1M unbuffered Tris-HCl solution was added to neutralize the pH. The products of the primer extension reaction were resolved on denaturing 6% polyacrylamide gels and visualized by autoradiography using a FPL-5000 Image Reader.

Band intensities were quantified using Multi Gauge software (Fuji Photo Film Inc). First, 1M7 reactivity for each position was calculated by subtracting the control (DMSO) band intensity from the "1M7-modified" band intensity. For each extension primer, the reactivity of nucleotides was then normalized relative to the most reactive position, which was assigned a value of 1. Nucleotides with normalized reactivity between 0.3 and 0.5 were considered to be moderately reactive with 1M7, while nucleotides with normalized reactivity above 0.5 were considered to be highly reactive with 1M7.

Results

Characterization of Intronic Sequences Involved in LDI

Figure 2A:
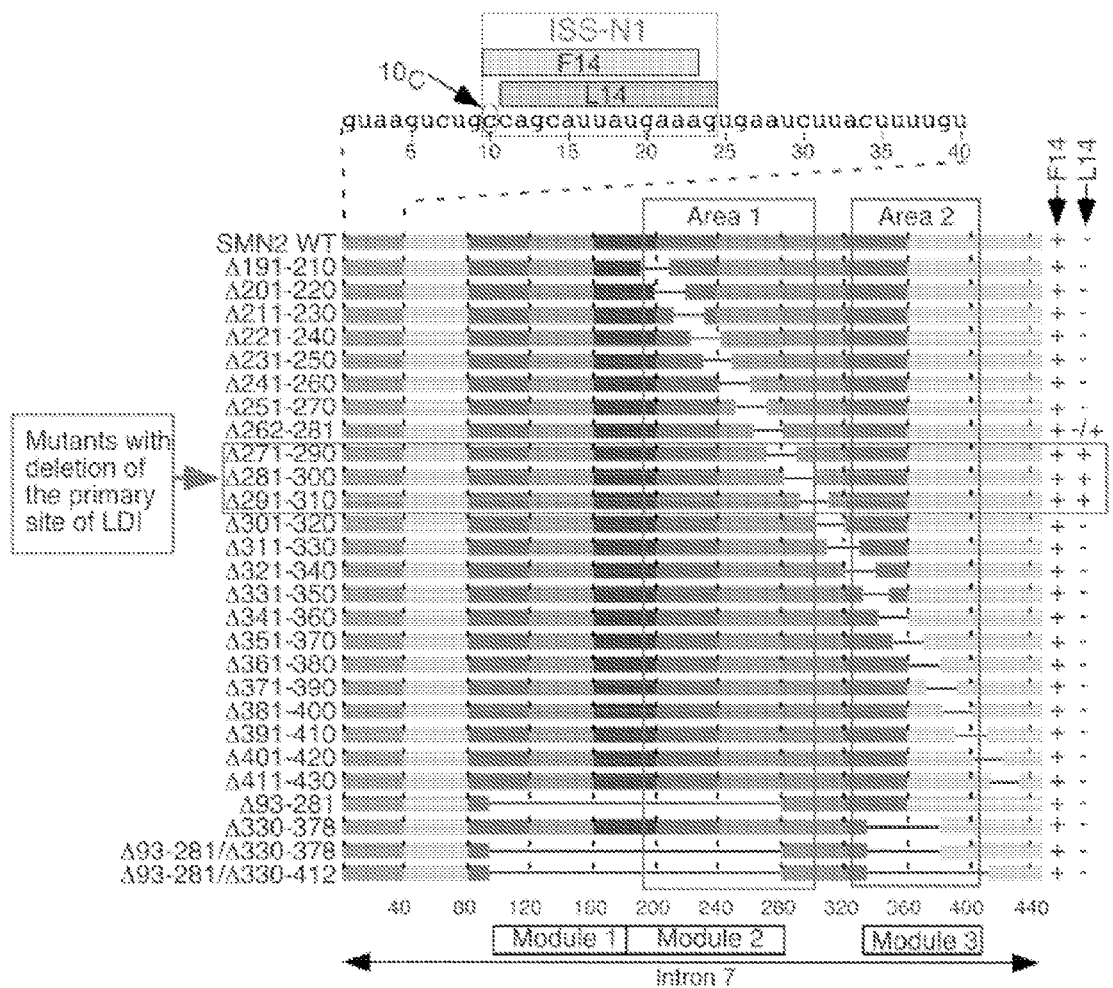
FIGS. 2A and 2B show the identification of the primary site of the $^{10}$C-mediated LDI. (A) Diagrammatic representation of 20-nt long overlapping deletions within SMN2 intron 7. The sequence of the first 40 nucleotides of intron 7 is given at the top (SEQ ID NO: 56), with F14 and L14 target sites within ISS-N1 indicated. Deletions are shown as lines. Mutants' names are given on the left. Numbers in mutants' names represent the positions at which deletions were made. The effect of F14 and L14 on splicing is indicated on the right with "+" (promotes exon 7 inclusion) and "−" (promotes exon 7 skipping). (B) In vivo splicing pattern of the wild type SMN2 minigene and the representative deletion mutants from panel (A) in the presence of the indicated ASO. Exon 7-included (+) and exon 7-skipped (−) spliced products are marked. Control represents transfection with 10-mer ASO (Table 2). Results were analyzed as described in (33). Abbreviation: Ex7, exon 7.
Figure 2B:
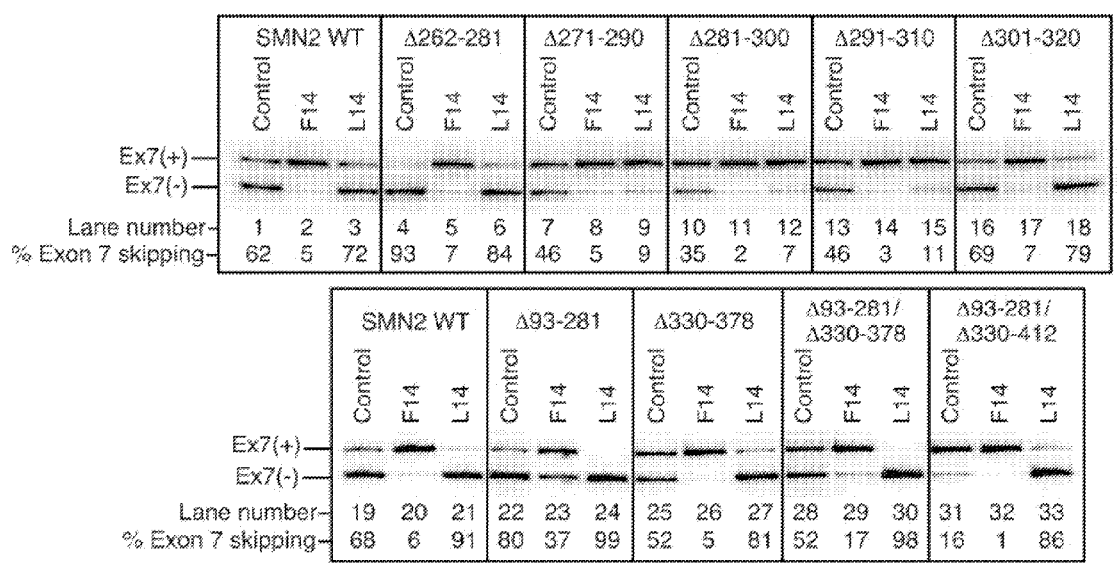

We previously reported that the $^{10}$C-mediated LDI is modulated by sequences from the $195^{th}$ to $306^{th}$ (Area 1) and $325^{th}$ to $405^{th}$ (Area 2) positions of SMN2 intron 7 (FIG. 2A; 40). In order to understand the mechanistic basis of the $^{10}$C-mediated LDI, we thought it essential to link the L14-induced inhibitory effect of $^{10}$C to the smallest possible sequence. For this, we generated a set of 23 SMN2 minigenes carrying 20-nt long overlapping deletion mutations encompassing Area 1 and Area 2 (FIG. 2A). We then co-transfected HeLa cells with these minigenes and F14 or L14 and determined the splicing pattern of exon 7 at ~24 h post transfection. As shown in FIG. 2B, L14 increased exon 7 skipping in the majority of mutants except Δ271-290, Δ281-300 and Δ291-310, and to a lesser extent Δ262-281, while F14 caused predominant exon 7 inclusion in all cases. These results refined the region of the LDI as a single sequence stretch between positions 271 and 300 within Area 1; we consider it to be the primary site of LDI. Consistently, L14 retained the inhibitory effect on exon 7 splicing in SMN2 minigenes carrying large deletions outside of the identified site, namely spanning the region from position 93 to 281 and position 330 and 412 (FIG. 2B, lanes 22-33). Of note, these large deleted sequences fold into independent secondary structures or modules (Modules 1, 2 and 3; FIG. 2A) as determined by structure probing (described later). To summarize, our results of large deletions and the 20-nt long overlapping deletions narrowed the primary site of the $^{10}$C-mediated LDI to an area between the $282^{nd}$ and $300^{th}$ positions of intron 7.

Figure 3A:
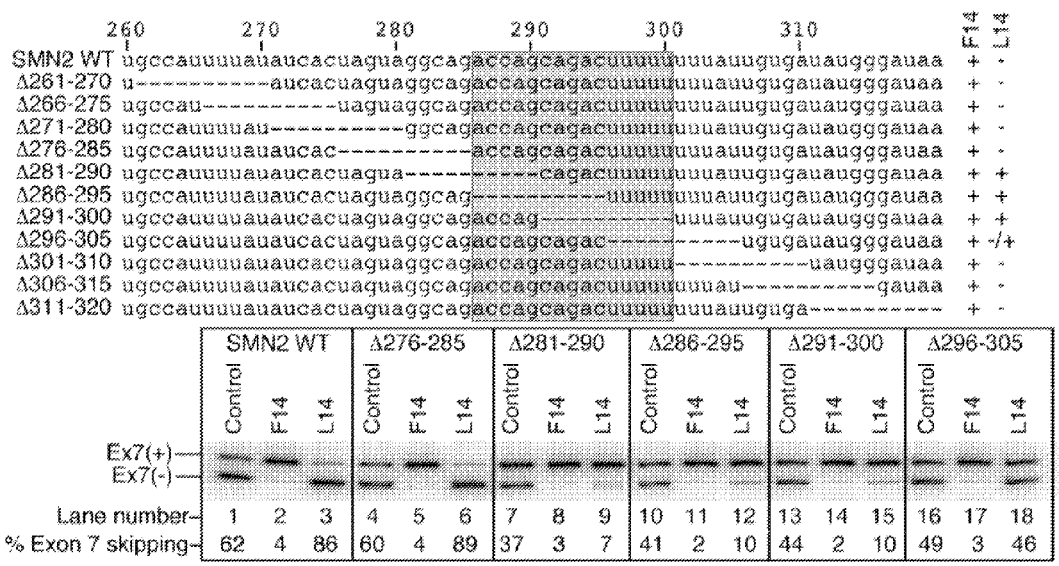
FIG. 3A-3C show the Characterization of the smallest motif of the $^{10}$C-mediated LDI. Intron 7 sequences of 10—(A) (SEQ ID NOs: 57-68), 5—(B) (SEQ ID NOs: 69-78) and 3-nt long (C) (SEQ ID NOs: 79-85) overlapping deletion mutants are shown with deletions indicated as dashed lines. Nucleotide numbering starts from the beginning of intron 7. Mutants' names are given on the left. Numbers in mutants' names represent the positions that were deleted. The effect of F14 and L14 on splicing is indicated similarly as in FIG. 2. The region determined to be an interacting partner of $^{10}$C is highlighted. In vivo splicing patterns of the wild type SMN2 minigene and the representative deletion mutants in the presence of the indicated ASOs are given in the bottom panels. Control ASO was the same as described in FIG. 2. Results were analyzed as described in (33).

To further define the sequence motif that interacts with $^{10}$C, we examined the splicing pattern of SMN2 mutants carrying 10-nt long overlapping deletions from the $261^{st}$ to $320^{th}$ positions of intron 7 (FIG. 3A, upper panel). As expected, F14 effectively stimulated exon 7 inclusion in all eleven mutants examined, whereas L14 inhibited exon 7 inclusion in all but four mutants (Δ281-290, Δ286-295, Δ291-300, and to a lesser extent Δ296-305) (FIG. 3A, lower panel). These results further narrowed the primary site of the $^{10}$C-mediated LDI to a single stretch of 15 nucleotides from the $286^{th}$ to $300^{th}$ positions of intron 7 (FIG. 3A, upper panel). Also, underscoring the inhibitory nature of this sequence, the 10-nt long overlapping deletions within this region themselves produced a noticeable stimulatory effect on SMN2 exon 7 splicing (FIG. 3A, lanes 1, 7, 10, 13, and 16).

Figure 3B:
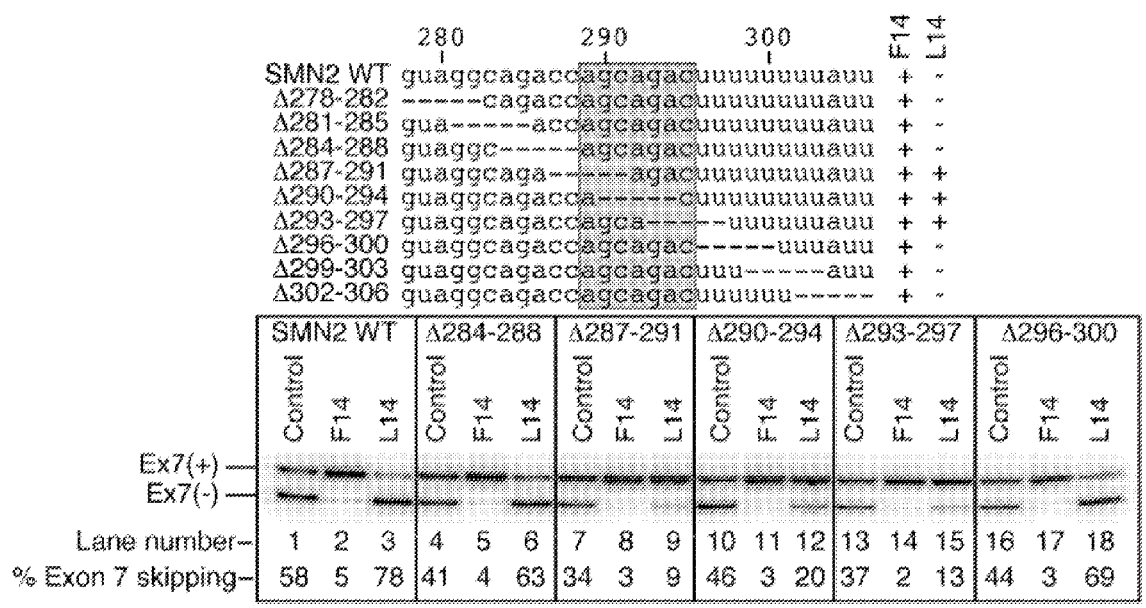
Figure 3C:
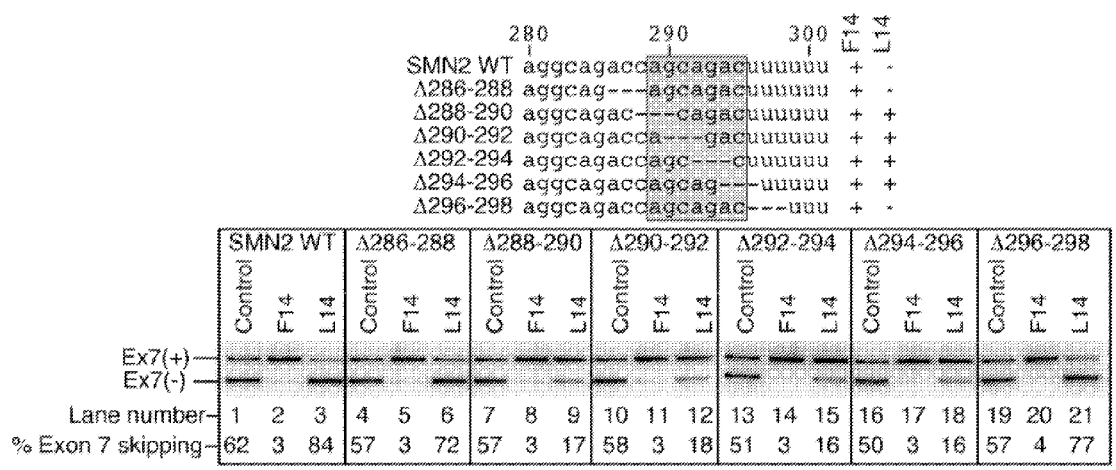

To continue our effort to find the smallest possible motif that is engaged in the LDI with $^{10}$C, we constructed a set of mutants carrying 5-nt long overlapping deletions within the sequence spanning from the $284^{th}$ to $300^{th}$ positions of SMN2 intron 7 (FIG. 3B, upper panel) and examined their splicing pattern in the presence of F14 or L14. We identified three overlapping deletion mutants (Δ287-291, Δ290-294 and Δ293-297) in which the ability of L4 to increase skipping of exon 7 was lost (FIG. 3B, lower panel). Thus, the primary site of the LDI was reduced to a single 7-nt long sequence, AGCAGAC, from the $289^{th}$ to $295^{th}$ positions of intron 7 (FIG. 3B, upper panel). We also performed a parallel experiment using SMN2 mutant minigenes that carried 3-nt long overlapping deletions within the sequence spanning from the $286^{th}$ to $298^{th}$ positions of intron 7 (FIG. 3C, upper panel). The results of this experiment identified the same 7-nt long motif, AGCAGAC, from position 289 to position 295 as the core site of the $^{10}$C-mediated LDI (FIG. 3C).

The Site of LDI Maps to a Unique RNA Secondary Structure

Figure 4A:
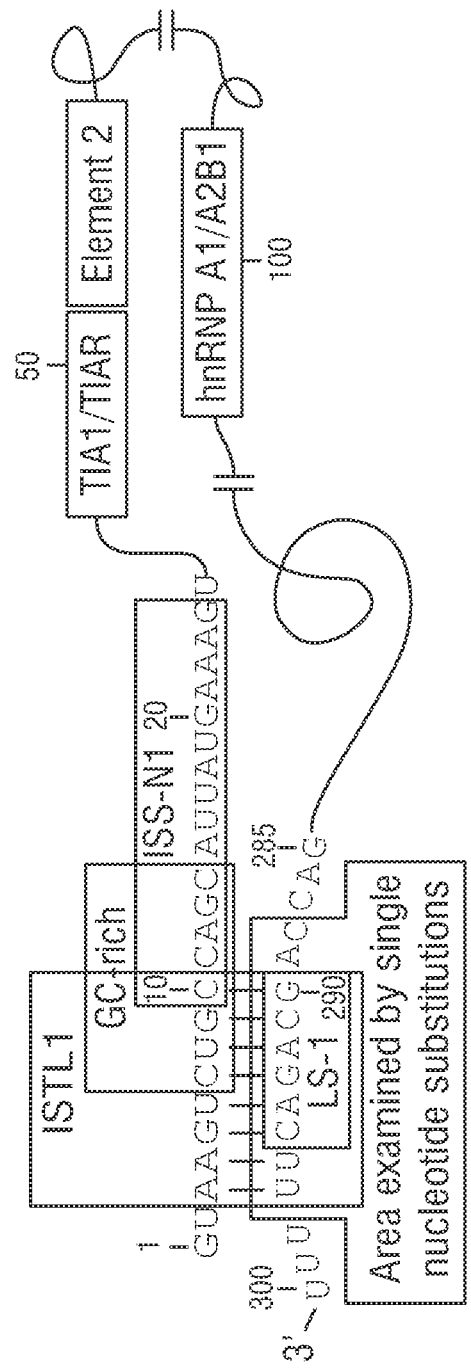
FIG. 4A-4C show the effect of point mutations within the smallest motif associated with the $^{10}$C-mediated LDI. (A) Diagrammatic representation of regulatory cis-elements/transacting factors and their relative arrangement in the context of SMN2 intron 7. The sequences of the first 25 nucleotides (SEQ ID NO: 86) and from the $285^{th}$ to $300^{th}$ positions (SEQ ID NO: 87) of intron 7 are given. The region targeted for single-nucleotide substitutions is highlighted. (B) In vivo splicing pattern of SMN2 mutants with single-nucleotide substitutions. Numbers and letters at the top of the gel represent the positions and the type of substitutions within intron 7. Spliced products are the same as those indicated in FIG. 2B. Results were analyzed as described in (33). (C) Bar diagram showing the percentage of exon 7 skipped in the presence of the control ASO, F14 and L14. Control ASO was the same as described in FIG. 2. Error bars represent standard deviations (minimum of 3 replicates). Numbers and letters at the bottom of the bar diagram represent the positions and the type of substitutions within intron 7. Every non-wild type nucleotide substitution within the highlighted LS-1 abrogated the negative effect of L14.
Figure 4B:
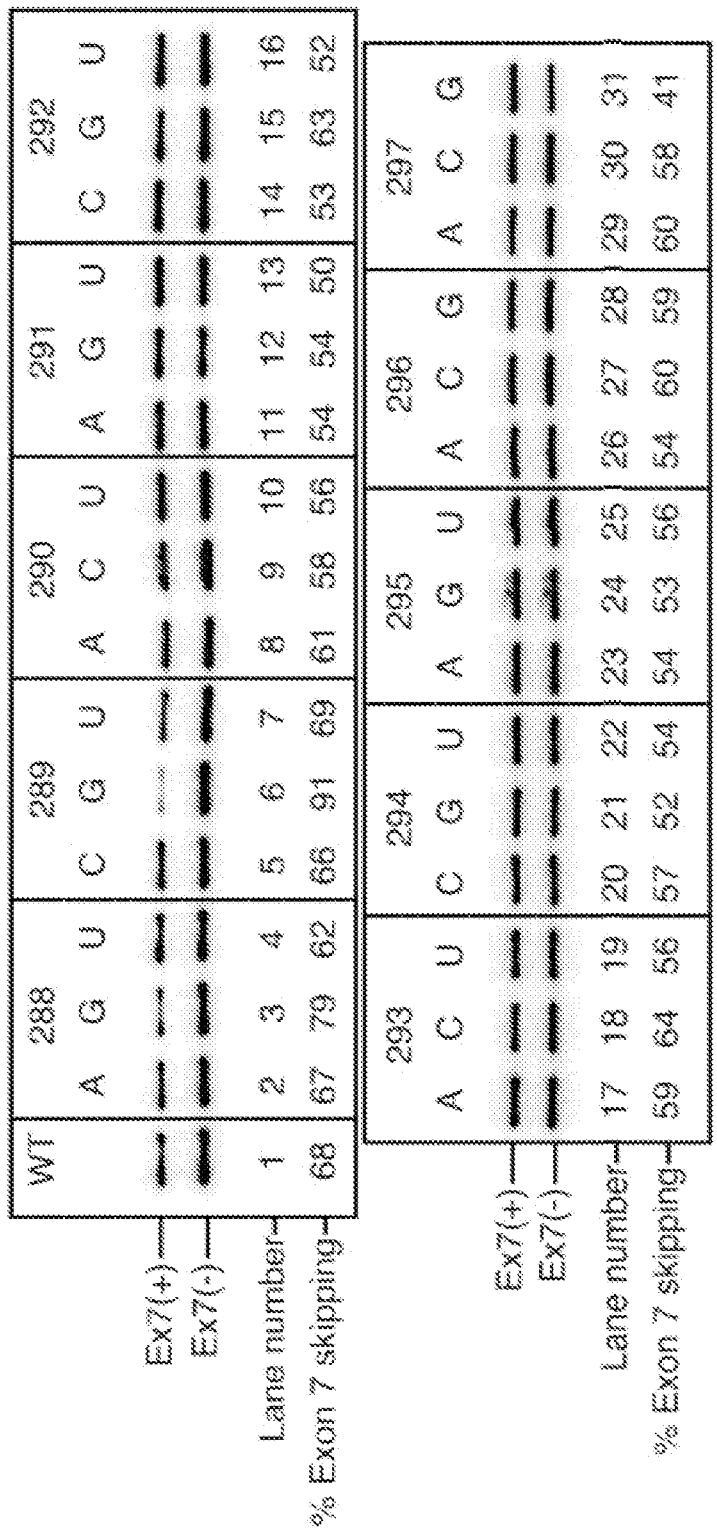

To assess the position-specific impact of residues involved in the interaction with $^{10}$C, we examined the effect of point mutations in a 10-nt long sequence stretch between intronic positions 288 and 297 on splicing of SMN2 exon 7 (FIG. 4). This sequence contains the newly identified site of the $^{10}$C-mediated LDI with a few upstream and downstream residues. Interestingly, all but one nucleotide of this sequence also constitute the 3' strand of a mfold (44) predicted secondary structure that we call internal stem through LDI-1 (ISTL1) (FIG. 4A). Note that the 5' strand of ISTL1 incorporates $^{10}$C. Consistent with the anticipated inhibitory role of ISTL1, a number of point mutations within the 3' strand of ISTL1 caused an improvement in SMN2 exon 7 inclusion (FIG. 4B). At the same time, an A to G substitution at the $289^{th}$ position, which is predicted to extend the size of the ISTL1 duplex by 1-bp, produced a strong inhibitory effect on SMN2 exon 7 splicing (FIG. 4B, lane 6). This finding further underscored the inhibitory role of ISTL1.

Figure 4C:
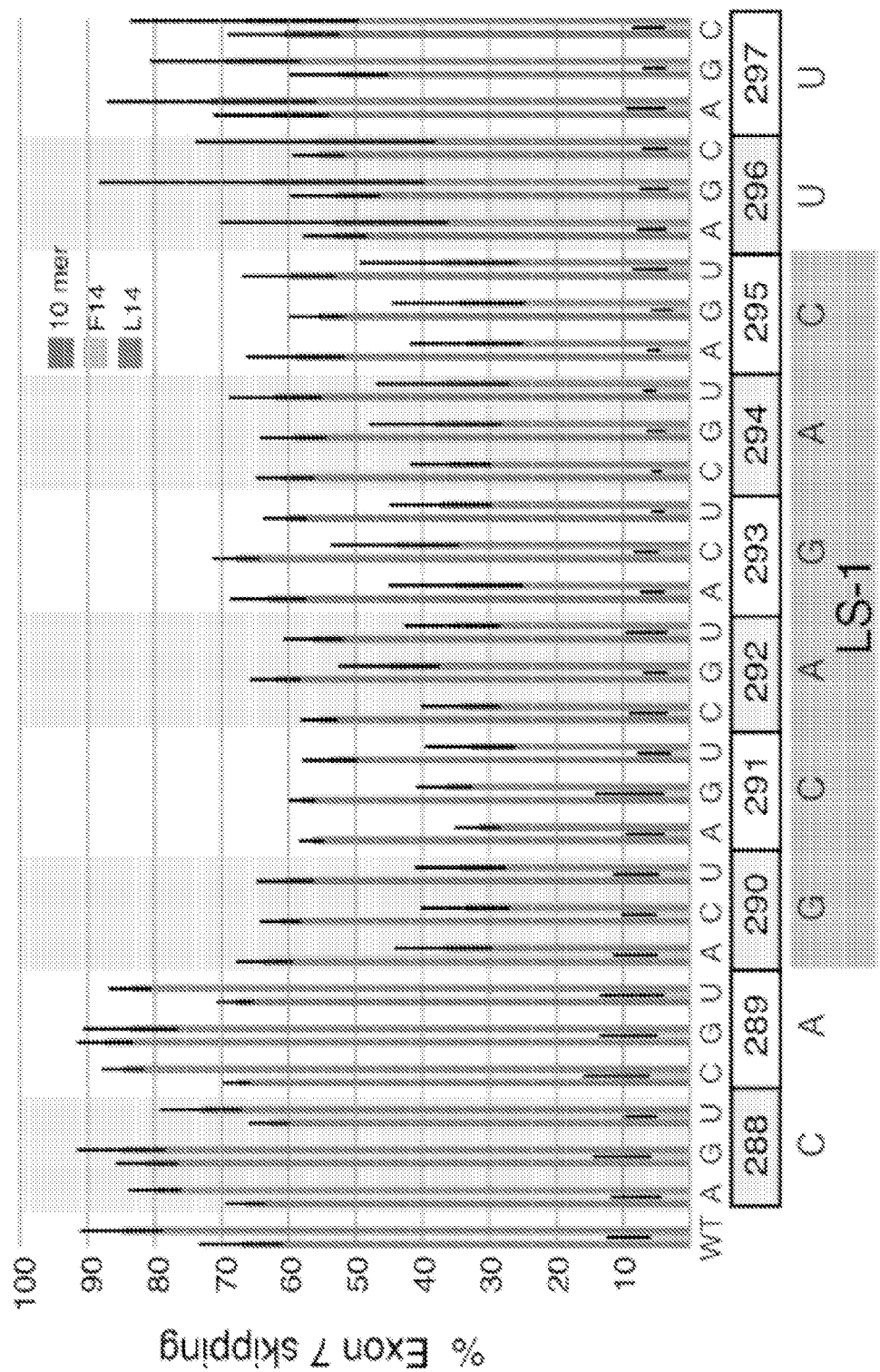

We next examined the effect of F14 and L14 on splicing of exon 7 in SMN2 minigenes carrying point mutations described in FIG. 4B. L14 produced a stimulatory effect on exon 7 splicing in all SMN2 minigenes with point mutations in the sequence spanning the $290^{th}$ to $295^{th}$ positions of SMN2 intron 7 (FIG. 4C). Therefore, we conclude that this sequence (GCAGAC) constitutes the LDI partner of $^{10}$C. To emphasize the sequence-specific and position-dependent nature of the $^{10}$C-mediated LDI, we term the GCAGAC motif spanning the $290^{th}$ to $295^{th}$ positions of intron 7 as LDI Site-1 or LS-1 (FIG. 4C). Since all six residues of LS-1 fall within the 3' strand of ISTL1 (FIG. 4A), we attribute the stimulatory effect of L14 on exon 7 splicing in LS-1 mutants to the destabilization of ISTL1. Remarkably, deletion of LS-1 but not an identical upstream GCAGAC motif abrogated the $^{10}$C-mediated LDI (FIG. 13). These results underlined the requirement of a specific sequence motif at a precise location within intron 7 for the interaction with $^{10}$C. These results are also consistent with a role of RNA structure in which specific positioning of LS-1 in the context of ISTL1 facilitates the LDI.

Role of ISTL1 in Regulation of SMN2 Exon 7 Splicing

Figure 5A:
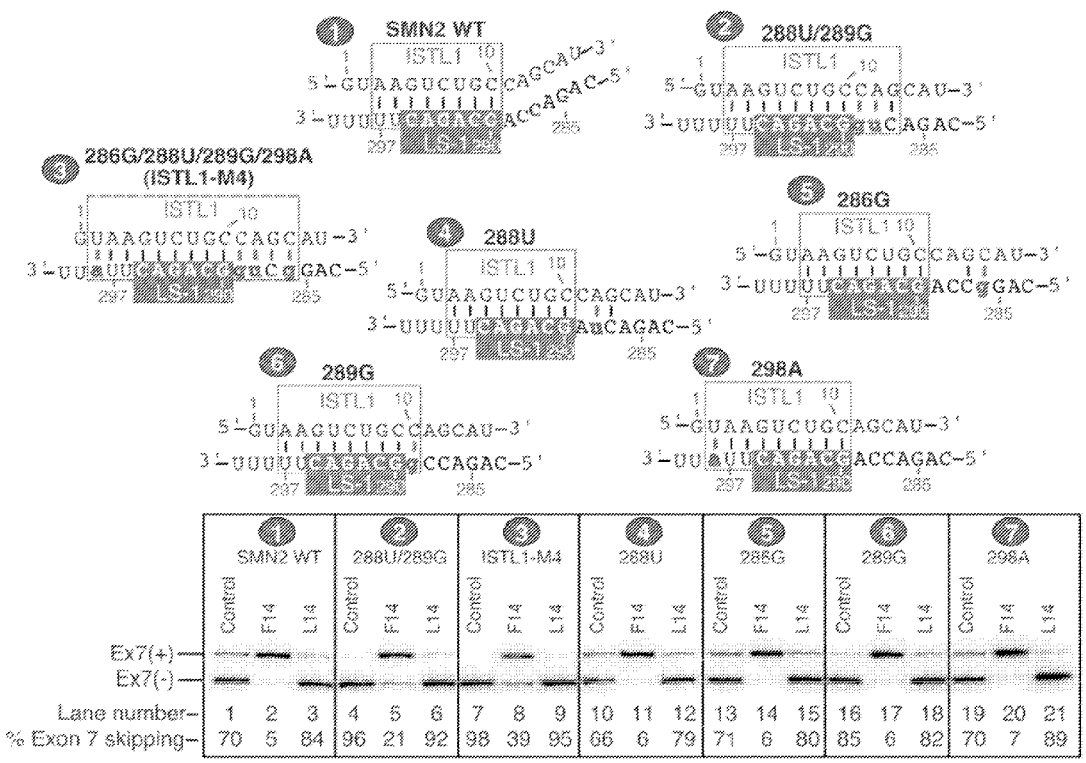
FIGS. 5A and 5B show the effect of structure-associated mutations on the $^{10}$C-mediated LDI. (A) Upper panel shows diagrammatic representation of predicted ISTL1 strengthened by mutations indicated in lower-case letters (SEQ ID NOs: 47, 88-94). New base pairs formed due to these mutations are shown as gray lines. Each minigene was assigned a name and a number as shown at the top of each structure. In vivo splicing patterns of minigenes in the presence of the indicated ASOs are shown in the bottom panel. Spliced products are the same as those marked in FIG. 2B. Control ASO was the same as described in FIG. 2. Results were analyzed as described in (33). (B) Upper panel shows diagrammatic representation of the predicted ISTL1 destabilized or restored by mutations indicated in lower-case letters (SEQ ID NOs: 95-100). Restored base pairs formed due to the mutations are shown as gray lines. Other descriptions are same as in panel A.

To evaluate the impact of the ISTL1 structure on exon 7 splicing, we generated a SMN2 minigene with a double mutation (288U/289G), which is predicted to extend the length of ISTL1 by 3-bp. This mutant showed greatly increased exon 7 skipping as compared to the wild type construct (FIG. 5A, lane 4). Furthermore, another minigene mutant, ISTL1-M4, which carried four substitutions (286G/288U/289G/298A), and therefore is predicted to have at least 13-bp long ISTL1, showed near-total skipping of exon 7 (FIG. 5A, lane 7), confirming that the inhibitory effect of ISTL1 is proportional to the size of the stem. Of note, in both mutants the target site of F14 is partially sequestered by ISTL1. Consequently, in both mutants F14 had a diminished stimulatory effect on exon 7 splicing (FIG. 5A, lanes 5 and 8). We also compared the effect of single nucleotide substitutions at the $286^{th}$, $288^{th}$, $289^{th}$ and $298^{th}$ positions of intron 7. While both 289G and 298A mutants are predicted to extend ISTL1 by 1-bp, only 289G showed a noticeable increase in SMN2 exon 7 skipping (FIG. 5A, lanes 16 and 19). This difference could be due to the fact that the A:U base pair formed by 298A is weaker than the G:C base pair formed by 289G (FIG. 5A, upper panel). As expected, 288U and 286G mutations that did not increase the size of ISTL1 had no appreciable gain in the inhibitory effect on SMN2 exon 7 splicing (FIG. 5A, lanes 10 and 13).

Figure 5B:
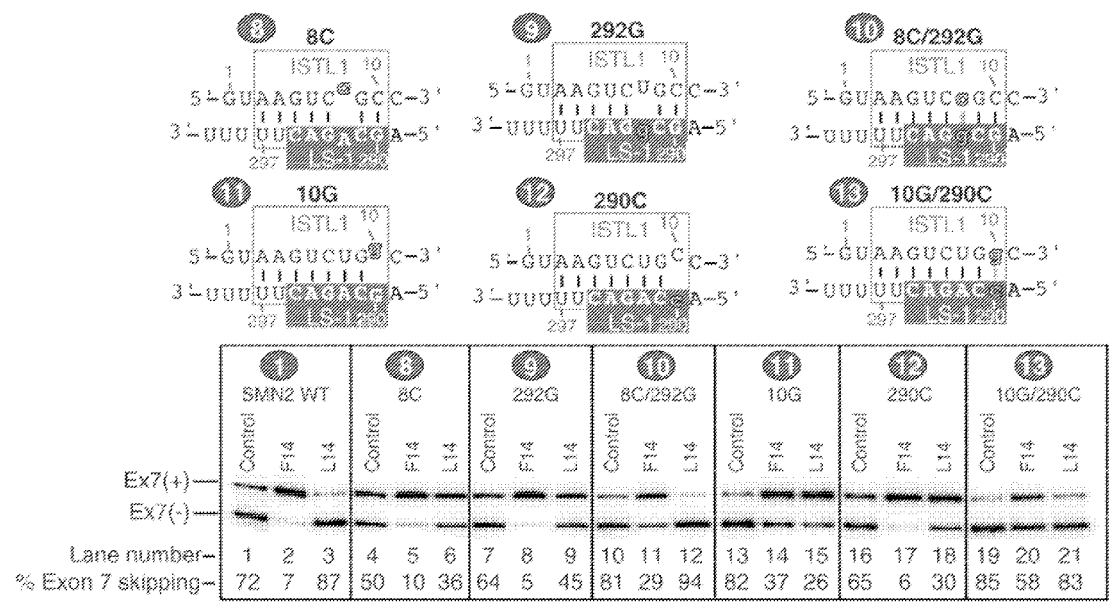

To functionally validate the role of ISTL1 on SMN2 exon 7 splicing we tested the effect of compensatory mutations. In particular, we substituted U for C at the $8^{th}$ (8C) and C for G at the $10^{th}$ (10G) positions of SMN2 intron 7. The 8C and 10G mutants had stimulatory and inhibitory effects on exon 7 splicing, respectively (FIG. 5B, lanes 4 and 13). The unexpected negative effect of the 10G mutation could be due to creation and/or strengthening of an existing inhibitory element. Similar to point mutations within the 3' strand of ISTL1 (FIG. 4), these mutations are predicted to destabilize ISTL1. Consistently, L14 lost its inhibitory effect and promoted inclusion of exon 7 in both 8C and 10G mutants (FIG. 5B, lanes 6 and 15). These results further supported the hypothesis that destabilization of ISTL1 is necessary to abrogate the $^{10}$C-mediated LDI. In the context of the wild type SMN2 intron 7, 8U and 10C residues are predicted to base pair with 292A and 290G, respectively. Mutations at either the $290^{th}$ or $292^{nd}$ positions abrogated the negative effect of L14 (FIG. 4C; FIG. 5B, lanes 9 and 18). We predicted that in the minigenes 8C/292G and 10G/290C that carry restored ISTL1, L14 would either regain its negative effect on exon 7 splicing or suppress the stimulatory effect it produced in minigenes carrying single nucleotide mutations. Indeed, L14 noticeably increased exon 7 skipping in the 8C/292G mutant and suppressed the stimulatory effect in case of 10G/290C (FIG. 5B, lanes 12 and 21). These results provided strong evidence in support of the modulatory role of ISTL1 structure in SMN2 exon 7 splicing.

Structure Probing Supports ISTL1 Formation

To validate the formation of ISTL1, we employed SHAPE, a powerful chemical structure probing technique (42). In this assay, 1-methyl-7-nitroisatoic anhydride (1M7) modifies the freely available 2'-hydroxyl groups (of sugar moieties) of nucleotides. In general, residues located in loops and bulges are reactive, whereas residues that form stems or engage in high-order interactions are protected from modification. We performed all our structure probing experiments using a 467-nt long RNA harboring TSL2, a structure formed at the 3' end of exon 7 (16), and the entire intron 7. The secondary structure of SMN2 intron 7 deduced from the SHAPE analysis showed a substantial overlap with the predicted secondary structure (FIG. 6). According to our results, intron 7 folds into several hairpins (TSLs) and internal stems formed by LDIs (ISTLs). Importantly, the results of SHAPE validated the formation of ISTL1 (FIG. 6A). For instance, fourteen out of sixteen residues of ISTL1 were largely inaccessible for modification. We detected some degree of modification of 3A and 293G that are located at the terminal position and in the middle of ISTL1, respectively. Of note, examples of SHAPE reactivity for nucleotides located within a stem have been reported (45,46). Validating the formation of TSL2, three base pairs in the middle of the stem of TSL2 were completely protected from modification (FIG. 6A). We did observe accessibility of additional residues at the most flexible positions such as loop closing and the base of the stem of TSL2 (FIG. 6A).

The probed structure localized ISTL1 adjacent to two internal stems, which we designated as ISTL2 and ISTL3 (FIG. 6A). The sequence stretch connecting the 5' strand of ISTL1 with the 5' strand of ISTL2 folds into a hairpin structure (TSL3), which partially sequesters the previously reported binding sites of hnRNP A1/A2B1 and TIA1 proteins (FIG. 6A). A few nucleotides in the predicted stem of TSL3 were found to be accessible for modification. These include a U residue (25U) in the loop-closing base pair, a G residue (39G) in the wobble base pair, and an A residue (18A) in the neighboring base pair (FIG. 6A). Residues immediately upstream and downstream of TSL3 are located within internal loops (FIG. 6A). It is likely that the formation of these loops is dictated by the topological constraints imposed by ISTL1 and ISTL2. We also identified two regions where the SHAPE results did not corroborate with the mfold predicted structure. These regions constitute Modules 1 and 2 that occupy a major portion of intron 7 (FIG. 6). We conclude that the formation of ISTL1 is independent of these modules, since their deletion did not abrogate the inhibitory effect of L14 (FIG. 2). Another structural module, Module 3, deletion of which had no consequences on the negative effect of L14, showed substantial agreement between the experimentally derived and the mfold predicted structure (FIG. 6). Simultaneous deletions of Modules 1, 2 and 3 retained the inhibitory effect of L14 (FIG. 2), suggesting that formation of ISTL1 is feasible even in the context of a very short intron 7.

To further confirm the formation of ISTL1, we compared the SHAPE profiles of the wild type and ISTL1-M4 RNAs. As predicted, ISTL1-M4 RNA showed a significantly decreased 1M7 reactivity of the –1A, 1G, 2U, 3A 11C, 12A, 13 G and 14C nucleotides that are located in the extended 5' strand of ISTL1 (FIG. 7A, compare lanes 6 and 7; FIG. 7C, upper panel). SHAPE results also indicated that the extended stem in ISTL1-M4 RNA caused perturbations in several local structures. For instance, multiple residues involved in the formation of TSL3 became accessible for modification by 1M7 (FIG. 7A; FIG. 7C, upper panel). In addition, ISTL2 became destabilized as indicated by the increase in 1M7 modifiability of residues in its 5' strand, particularly at positions 51 and 56 (FIG. 7A; FIG. 7C, upper panel). To obtain additional validation that the 5' and 3' strands of ISTL1 are protected from modifications due to base pairing with each other, we performed SHAPE analysis of ISTL1-M4 RNA refolded and probed in the presence of an ASO (ASO-M) that targeted the mutated 3' strand of ISTL1 (from the $275^{th}$ to $297^{th}$ positions of intron 7) (FIG. 7B). As expected, the presence of ASO-M increased the reactivity of residues from the last position of exon 7 to the $14^{th}$ position of intron 7 (FIG. 7A, compare lanes 7 and 8; FIG. 7C, lower panel). Interestingly, ASO-M had a much lesser effect on accessibility of C residues at the $10^{th}$ and $11^{th}$ positions of intron 7 (FIG. 7A; FIG. 7C, lower panel). This could be due to engagement of these residues in an alternative interaction when the 3' strand of ISTL1 is sequestered by ASO-M. In addition, instances in which C residues in flexible regions display lower SHAPE reactivity than other residues with similar apparent local structure have been reported (45). Overall, our results provided the first validated example in which the sequestration of a deep intronic sequence increased the accessibility of the 5' ss of an exon.

We also compared the SHAPE profiles of the 3' strands of ISTL1 in the wild type and ISTL1-M4 RNAs. Interestingly, we observed a significant falloff of reverse transcriptase (RTase) at positions 292 and 293 in the mutant RNA in both control (DMSO) and 1M7 treated samples that interfered with structure determination (FIG. 14). We attribute these falloffs to a combination of factors, including the presence of a strong secondary structure (ISTL1) in front of the U-rich tract. To obviate the RTase falloff, we modified our primer extension reaction by adding an ASO (ASO-D), which is predicted to disrupt ISTL1 by sequestering its 5' strand (FIG. 8B). Indeed, the presence of ASO-D fully prevented the falloff of RTase at the $292^{nd}$ and $293^{rd}$ positions (FIG. 14).

These results provided additional evidence in support of the formation of ISTL1. With the exception of 293G, residues from the 275$^{th}$ to 297$^{th}$ positions of intron 7 were poorly modifiable by 1M7 due to their incorporation within ISTLs (FIG. 8A, compare lanes 5 and 6; FIG. 8C, upper panel). Yet, ISTL1-M4 RNA showed a further decrease in 1M7 reactivity on residues from the 286$^{th}$ to 297$^{th}$ positions of intron 7 (FIG. 8A; FIG. 8C, upper panel). Also, reactivity at the 298$^{th}$ and 299$^{th}$ positions decreased in the mutant ISTL1, while residues at the 283$^{th}$ to 285$^{th}$ positions located immediately upstream of the strengthened ISTL1 became moderately to highly modifiable (FIG. 8A; FIG. 8C, upper panel). As expected, the SHAPE profile generated for the mutant RNA refolded and probed with ASO-D showed an increase in the 1M7 reactivity of nucleotides from the 286$^{th}$ to 299$^{th}$ positions of intron 7, with the exception of 291C (FIG. 8A; FIG. 8C, lower panel). To summarize, our results of structure probing confirmed the formation of ISTL1.

Effect of F14 and L14 on Stability of ISTL1

To capture the effect of F14 and L14 on ISTL1 and other structures of intron 7, we performed SHAPE analysis in which we refolded the wild type RNA in the presence of F14 or L14 prior to incubation with 1M7. The SHAPE profiles confirmed the appropriate annealing of F14 and L14 to their respective targets (FIG. 9A). Since the target sites of both F14 and L14 overlap the 5' strand of the stem in TSL3, we observed increased 1M7 reactivity of residues from the 33$^{rd}$ to 41$^{st}$ positions of intron 7 in the presence of either F14 or L14 (FIG. 9A: FIG. 9B, upper and middle panels). In addition, both ASOs caused an increase in modifiability of some of the residues in the region that encompasses the 5' strand of ISTL2 (FIG. 9). Importantly, F14 and L14 caused destabilization of the region upstream of their annealing sites as indicated by an increase in the modifiability of residues in the area extending to the two last positions of exon 7 (FIG. 9). Notably, F14 showed a greater destabilizing effect than L14 (FIG. 9B, lower panel).

The presence of F14, but not L14, resulted in a very slight increase in the modifiability of residues that constitute the 3' strand of ISTL1 (FIG. 15). Consistent with the increased 1M7 reactivity of residues between the 50$^{th}$ and 58$^{th}$ positions of intron 7 (FIG. 9), we also observed increased modifiability of residues in the complementary 3' strand of ISTL2 in the presence of both ASOs, particularly at positions 284 and 285 (FIG. 15). A comparison of SHAPE profiles did not reveal any novel secondary structure whose formation was induced by annealing of either F14 or L14 to their respective targets. However, it is possible that the minor structural differences induced by F14 and L14 may be sufficient to create distinct topological context for the RNA-protein interactions.

Role of Protein Factors in $^{10}$C-Mediated LDI

The abundantly expressed proteins hnRNP A1/A2B1 and PTB1 have been implicated in skipping of SMN2 exon 7 (refs. in 32). Due to the proximity of ISS-N1 to ISTL1 in the folded RNA, there is a probability that the in vivo interaction of hnRNP A1/A2B1 with ISS-N1 is facilitated by ISTL1. It is also possible that hnRNP A1/A2B1 assists folding of or stabilizes ISTL1. Considering the longest U-rich tract of intron 7 is located immediately downstream of the LS-1 sequence (FIG. 6), PTB1 may be involved in ISTL1 formation as well. To explore whether hnRNP A1/A2B1 and PTB1 are at all associated with the $^{10}$C-mediated LDI, we first depleted HeLa cells of these proteins using a siRNA-based approach and then transfected these cells with F14 or L14 followed by determination of splicing pattern of endogenous exon 7 from both SMN1 and SMN2. To distinguish between SMN1 and SMN2 transcripts, we took advantage of a DdeI restriction site specific to SMN2 exon 8 (25). As expected, depletion of either hnRNP A1 or A2B1 produced a noticeable stimulatory effect on SMN2 exon 7 splicing (FIG. 10A; FIG. 10B, lanes 4 and 7). In particular, SMN2 exon 7 inclusion was substantially higher in hnRNP A2B1-depleted compared to hnRNP A1-depleted cells. However, the inhibitory effect of L14 on SMN2 exon 7 splicing was not abrogated by knockdown of hnRNP A1 and A2B1, individually or together (FIG. 10, lanes 6, 9 and 12). Interestingly, depletion of hnRNP A2B1 alone or together with hnRNP A1 produced more than a three-fold increase in L14-induced skipping of SMN2 exon 7 compared to only about two-fold increase when control siRNA treated HeLa cells were transfected with L14 (FIG. 10B, compare lane 3 with lanes 6, 9 and 12). Since hnRNP A1 and A2B1 are involved in several other processes, including but not limited to transcription and microRNA biogenesis (47), we attribute these differences to indirect factors. Similar to hnRNP A1/A2B1, depletion of PTB1 did not eliminate the inhibitory effect of L14 on SMN2 exon 7 splicing (FIG. 10B, lane 15). Therefore, our results clearly ruled out the role of hnRNP A1/A2B1 and PTB1 in the $^{10}$C-mediated LDI.

ISTL1 as a Potential Therapeutic Target for Splicing Correction in SMA

The widely used GM03813 cell line (SMA type I fibroblasts) contains only SMN2 and provides an ideal cell-based disease model to check the efficacy of compounds to modulate SMN2 exon 7 splicing in vivo. To evaluate the impact of ISTL1 in the context of the endogenous gene, we transfected GM03813 cells with ASOs that annealed to overlapping intronic targets encompassing the 3' strand of ISTL1 and neighboring sequences. To avoid off target effects, we performed this experiment at a low nanomolar (15 nM) concentration of ASOs. Supporting the inhibitory nature of ISTL1, ASOs that sequestered the 3' strand of ISTL1 promoted SMN2 exon 7 inclusion (FIG. 11A, lanes 4-8). ASO 283-297, which sequestered the entire 3' strands of ISTL1 and ISTL2, emerged as the most effective ASO, whose stimulatory effect was comparable to that of F14, which targeted ISS-N1 (FIG. 11A, lanes 6 and 11). ASO 276-290, which predominantly targeted the 3' strands of ISTL2 and ISTL3, also stimulated exon 7 inclusion, albeit to a substantially lower extent (FIG. 11A, lane 4). This reduced response may be due in part to partial destabilization of the neighboring ISTL1 and/or TSL3. For the convenience of distinction from our previously reported antisense target ISS-N1 (34), we designate sequences from the 275$^{th}$ to 297$^{th}$ position of intron 7 as ISS-N2 (FIG. 11A, upper panel). The inhibitory nature of ISS-N2 is fully supported by the results of antisense microwalk (FIG. 11A) and the overlapping deletions (FIGS. 2 and 3). Similar to ASO 283-297, a 23-nt long ASO that fully sequestered ISS-N2 stimulated exon 7 inclusion see FIG. 17.

We also examined the effect of ASO 283-297 on the levels of SMN in SMA patient cells. As a positive control we used a 20-mer ASO (Anti-N1) that is known to stimulate SMN2 exon 7 inclusion by binding to ISS-N1 (34). As a negative control we used a 10-mer ASO described previously (40). We transfected GM03813 cells with 40 nM of a given ASO and determined the splicing pattern of SMN2 exon 7 as well as the protein levels at 48 h post-transfection. As expected, ASO 283-297 effectively stimulated SMN2 exon 7 inclusion and up-regulated SMN protein levels in SMA patient cells (FIG. 11B). We also observed a noticeable increase in the level of SMN-interacting protein Gemin2 (FIG. 11B, left panel). The stimulatory effect of ASO 283-297 on SMN2 exon 7 splicing and levels of SMN and Gemin2 was comparable to that of Anti-N1 (FIG. 11B). Taken together, these results represent the first example in which an ASO annealing to a deep intronic sequence to corrects aberrant splicing and restores high levels of a full-length protein in a cell-based model of a genetic disease.

Discussion

SMA is the leading genetic cause of infant mortality. The disease has the potential to be corrected through prevention of SMN2 exon 7 skipping. Our previous discovery of the 15-nt long ISS-N1 has emerged as the most promising target for an ASO-mediated restoration of SMN2 exon 7 inclusion (34-39). This study began with the aim to uncover how two 14-mer ISS-N1-targeting ASOs (F14 and L14) produced opposite effects on alternative splicing of SMN2 exon 7. We established that the inhibitory effect of L14 is exclusively linked to the unsequestered $^{10}$C and is contingent upon the presence of a downstream intronic sequence separated from $^{10}$C by hundreds of nucleotides; there was no precedence of any similar finding. To identify the motif associated with the $^{10}$C-mediated LDI, we adopted an unbiased approach in which we tested the effect of L14 on splicing of SMN2 minigene mutants harboring large deletions and 20-nt long overlapping deletions within the entire 3'-half of intron 7. Our results delineated a single 19-nt long sequence stretch from the $282^{nd}$ to $300^{th}$ positions of intron 7 as the primary site of the LDI associated with $^{10}$C (FIG. 2). Subsequent screening of minigenes with shorter overlapping deletions and with point mutations narrowed the site of the LDI to a 6-nt long motif (LS-1) that spans from the $290^{th}$ to $295^{th}$ positions of intron 7 (FIGS. 3 and 4). LS-1 is located within the 3' strand of an mfold-predicted structure we term ISTL1 (FIG. 4A). The 5' strand of ISTL1 harbors $^{10}$C, which base pairs with the first residue (290G) of LS-1 (FIG. 4A). Another motif identical to LS-1 (GCAGAC) spans the $282^{nd}$ d to $287^{th}$ positions of intron 7. Interestingly, deletion of LS-1 (Δ290-295) and not the identical upstream sequence (Δ282-287) abrogated the formation of ISTL1 and led to the complete loss of the inhibitory effect associated with L14 (FIG. 13). These results underscored the critical role of structural context of LS-1 for the realization of the inhibitory effect associated with $^{10}$C. Consistent with this statement, all intronic deletions that retained the inhibitory effect of L14 maintained the formation of ISTL1.

Compared to ISS-N1 deletion that produced a strong stimulatory effect on SMN2 exon 7 splicing (34), deletion of LS-1 and intronic sequences immediately upstream of LS-1 produced a moderate but noticeable stimulatory effect on exon 7 splicing (FIG. 2B, lanes 7, 10 and 13; FIG. 3A, lanes 7, 10, 13 and 16; FIG. 3B, lanes 7, 10, 13 and 16; FIG. 3C, lanes 13 and 16). However, due to potential creation of artificial cis-element and/or relocation of the existing cis-elements, results of deletion mutations should be interpreted with caution. For instance, since deletion of LS-1 and sequences immediately upstream of LS-1 still retained ISS-N1 that kept the TIA1 binding site away from the 5' ss of exon 7, it did not have the similar additive stimulatory effect on SMN2 exon 7 splicing as was observed in case of ISS-N1 deletion. Nonetheless, our results of deletion mutations combined with the enhanced stimulatory effects of F14/L14 on SMN2 exon 7 splicing produced sufficient enough lead for the identification of ISTL1 that we determined to be the sole facilitator of a unique LDI associated with $^{10}$C. Interestingly, Δ262-281 and Δ301-320 mutants showed a noticeable increase in SMN2 exon 7 skipping (FIG. 2B, lanes 4 and 16). This could be due to the loss of the stimulatory cis-elements in these mutants. It is also likely that these mutants somehow strongly enforce the formation of ISTL1.

The strongest evidence supporting the role of the ISTL1 structure in the $^{10}$C-mediated LDI came from the results of compensatory mutations. For example, 8C/292G and 10G/290C mutations, which altered the composition of ISTL1 but maintained the structure, were able to restore the inhibitory effect of L14 (FIG. 5B). These results also precluded the role of a linear motif encompassing the $10^{th}$ position of intron 7 in $^{10}$C-mediated LDI. While competing intronic RNA secondary structures have been predicted to play a positive role in the selection of mutually exclusive exons during splicing of the insect Dscam pre-mRNA (8), our results of compensatory mutations provide the first validated evidence that an intra-intronic RNA secondary structure formed by a LDI can play a negative role in splicing regulation. Previous studies have suggested that the weak 5' ss of SMN2 exon 7 is due to the presence of a local secondary structure (TSL2) and the close proximity of the 5' ss to hnRNP A1/A2B1 binding motifs within ISS-N1 (16, 32-35,48). The 5' strand of ISTL1 sequesters four out of the six residues involved in base pairing with U1 snRNA, a component of U1 snRNP, recruitment of which is critical for the definition of the 5' ss of exon 7 (16; FIG. 12). Supporting the negative role of ISTL1, mutations that extended the length of ISTL1 led to an increased skipping of SMN2 exon 7 (FIG. 5A). Therefore, our discovery of ISTL1 reveals an additional layer of control of SMN2 exon 7 splicing, where a deep intronic sequence may affect recruitment of U1 snRNP by a direct interaction with the 5' ss.

Having determined the functional significance of ISTL1, we next performed SHAPE analysis of a large RNA substrate harboring the entire intron 7 and the upstream exonic sequences encompassing TSL2. We also compared the structure of the wild type RNA with the ISTL1-M4 mutant that possessed a significantly strengthened ISTL1. The results of structure probing validated the formation of ISTL1. Consistently, the ISTL1-M4 mutant, predicted to greatly extend the length of ISTL1, showed protection of additional residues involved in the extension of the 5' and 3' strands of ISTL1 (FIGS. 7 and 8). The SHAPE profile of ISTL1-M4 confirmed that mutations deep inside intron 7 are able to affect the structure of a region located hundreds of nucleotides away, which is possible only when ISTL1 is formed (FIGS. 7 and 8). Overall, the pattern of 1M7-modified positions supported that intron 7 folds into a complex structure, including the formation of multiple adjacent helices (FIG. 6). Considering residues at the interface of adjacent helices generate co-axial stacking that imposes topological constraints on three-dimensional helix organization (49-51), we predict the existence of complex tertiary interactions involving loop-to-loop contacts. Consistently, SHAPE results indicated the presence of large terminal and internal loops as well as extended single stranded regions. Interestingly, two out of three reported intronic binding sites of hnRNP A1/A2B1 were localized in the structurally accessible regions of intron 7 (FIG. 6). On the other hand, most of the U-rich motifs associated with TIA1 were trapped within stems of TSL3 and ISTL2 (FIG. 6). Our findings suggest that the structural context of intron 7 is not conducive for the recruitment of TIA1, a critical positive regulator of SMN2 exon 7 splicing (31). Of note, TIA1 is the sole splicing factor whose mutation has been recently linked to defective SMN2 exon 7 splicing in the context of a genetic disease (52).

ISTL1 formation requires looping out of a 279-nt sequence, of which 189 residues are occupied by the independently folding Modules 1 and 2 (FIG. 6). A 147-nt long sequence downstream of ISTL1 contains another independently folding module (Module 3) that occupies 89 residues of intron 7 (FIG. 6). Simultaneous deletion of Modules 1, 2 and 3 reduced the size of intron 7 by more than half and yet preserved the inhibitory effect of L14 (FIG. 2). These results demonstrate that the formation of ISTL1 is independent of most of the local secondary structures within intron 7. However, the relative positioning of ISTL1 with respect to ISTL2 appears to modulate other local structures, particularly TSL3. This is quite evident in the ISTL1-M4 mutant, in which residues involved in the formation of TSL3 become modifiable by 1M7 (FIG. 7). Of note, strengthening of ISTL1 in this mutant did not sequester residues directly engaged in TSL3 formation and yet led to perturbation of TSL3. An increase in length of the ISTL1 helix in the ISTL1-M4 mutant also destabilized ISTL2 (FIGS. 7 and 8). These results suggest that the ISTL1 and ISTL2 in the wild type context have stabilizing roles on folding of local structures. Such roles for these structures would be analogous to tertiary interactions that are known to dictate the accuracy of local folding (50).

Upon comparing the 1M7 modification profiles of RNA refolded and probed in the presence of F14 and L14, we observed a link between destabilization of ISTL1 and a stimulatory effect of the ASOs on SMN2 exon 7 splicing. Although both F14 and L14 are predicted to generate a 14-bp long helix when bound to their respective targets, the F14 helix also invades ISTL1. Therefore, we found that F14 caused a somewhat greater increase in 1M7 modifiability of residues associated with ISTL1 as compared to L14 (FIG. 9). It is possible that the co-axial stacking of residues at the interface of the L14-duplex and ISTL1 brings topological constraint that prevents recruitment of U1 snRNP at the 5' ss of exon 7. Consistently, substitution at the $10^{th}$ intronic position has been shown to fully eliminate the inhibitory effect of L14 (40). Although both F14 and L14 disrupt TSL3, the constraint of co-axial stacking at the interface of ISTL1 and L14-duplex are likely to provide a different orientation of the TIA1 binding site located within the disrupted TSL3. Therefore, the inhibitory effect of L14 might be due to the unfavorable conformational changes that prevent recruitment of positive regulatory factors.

Previous reports have implicated hnRNP A1/A2B1 and PTB1 in skipping of SMN2 exon 7 (27,28,48). Incidentally, these abundantly expressed proteins are also involved in a looping mechanism that brings distantly located intronic motifs in close proximity (2,53).

To examine whether the inhibitory effect of L14 is linked to hnRNP A1/A2B1 and/or PTB1, we assessed the effect of L14 on splicing of endogenous SMN2 exon 7 in HeLa cells depleted of these proteins. Our results did not reveal any significant change in the negative effect of L14, suggesting that these proteins are not involved in L14-induced skipping of SMN2 exon 7 (FIG. 10). Based on our results, it is likely that the ISTL1-assisted sequestration of the 5' ss is a sufficient enough trigger to promote SMN2 exon 7 skipping. RNA helicases that bind and/or change the orientation of a RNA helix have been implicated in regulation of alternative splicing in pathological conditions (54,55). Future experiments will determine if RNA helicases affect SMN2 exon 7 splicing by targeting specifically ISTL1.

Having determined that ISTL1 imparts a negative effect on SMN2 exon 7 splicing by sequestration of the 5' ss of exon 7, we next evaluated the potential of ISTL1 as a target for an ASO-mediated splicing correction in SMA patient cells. Sequestration of the 3' strand of ISTL1 by an ASO is predicted to make the 5' ss of SMN2 exon 7 accessible for base pairing to U1 snRNA, a component of U1 snRNP (FIG. 12). In addition, TIA1 is known to enhance the recruitment of U1 snRNP to the 5' ss of exons (56). Therefore, we hypothesize that the sequestration of the 3' strand of ISTL2 might also promote U1 snRNP recruitment by releasing TIA1 binding sites located within the helices of ISTL2 and TSL3 (FIG. 12). Hence, we expected to see a better stimulatory effect on SMN2 exon 7 splicing when the 3' strands of ISTL1 and ISTL2 were sequestered simultaneously. Indeed, a 15-nt long ASO (ASO 283-297) that targeted the 3' strands of ISTL1 and ISTL2 significantly increased SMN2 exon 7 inclusion (FIG. 11A). Consistent with the stimulatory effect of ASO 283-297 on SMN2 exon 7 splicing, this ASO also increased the levels of SMN in SMA patient cells (FIG. 11B). SMN has high affinity for Gemin2. SMN:Gemin2 interaction has been considered to be one of the critical steps for the assembly of all SMN complexes (57,58). Consistent with the increase in SMN, we found increased levels of Gemin2 in SMA patient cells treated with ASO 283-297. Most importantly, the stimulatory effect of ASO 283-297 was found to be comparable to Anti-N1, a 20-mer ASO that targets ISS-N1.

While we have used only a 15-mer ASO to demonstrate the therapeutic potential of a deep intronic target, our results of deletion mutations support a larger inhibitory region that we term ISS-N2, which encompasses the 3' strands of ISTL1, ISTL2 and ISTL3 (FIG. 11A). Therefore, different oligonucleotide chemistries, particularly those that work better for longer ASOs, may be more useful when targeting the entire ISS-N2. Presently SMA has no cure. An ISS-N1-targeting ASO with phosphorothioate backbone and 2'-O-methoxyethyl (MOE) modification, a proprietary of ISIS Pharmaceuticals, is currently undergoing the $2^{nd}$ phase of clinical trial (Clinicaltrials.gov ID NCT01839656). For SMA therapy, our finding of ISS-N2 comes at a time when lack of additional targets has prevented clinical trials of ASOs with other promising chemistries that have shown encouraging results in recent pre-clinical and clinical trials (39,59). There is a substantial difference in sequence composition between ISS-N1 and ISS-N2. In view of the fact that sequence composition alone can affect pharmacokinetics and pharmacodynamics of an ASO, availability of ISS-N2 as a novel target has additional significance for developing an entirely new class of therapeutic ASOs for the treatment of SMA.

The coding sequence of mammalian SMN is mostly conserved. However, there is a noticeable divergence among intronic sequences. For example, mouse Smn intron 7 is 1640-nt long, while human SMN intron 7 is only 444-nt long. In addition to the absence of ISS-N1, mouse Smn intron 7 lacks $^{10}$C (34). Consistently, the mfold-predicted structure of mouse Smn intron 7 did not reveal a structure analogous to ISTL1/ISTL2/ISTL3 (not shown). Our results combined with the prior reports clearly suggest an evolutionarily distinct intra-intronic regulatory network that fine-tunes and modulates with utmost precision the splicing of human SMN exon 7 (FIGS. 6 and 12, FIG. 164; 32). Currently, the literature is replete with studies that focus on linear cis-elements, particularly in the beginning of introns (60,61). Our findings suggest that the information content of a linear cis-element at the beginning of intron can be tightly controlled by a deep intronic sequence. About 50% of all genetic disorders are caused by mutations that alter pre-mRNA splicing (62). Intronic sequences occupy a major portion (~26%) of human genome and represent ~94% of pre-mRNA (63). There is growing appreciation that a significant portion of the transcriptome's regulatory information is trapped in secondary and high-order RNA structures (64). Our discovery of ISTL1 provides the proof of principle how the structural information locked in the deep intronic sequence could impact the context of the 5' ss, which is often populated by a multitude of linear cis-elements. Our results also demonstrate that an ASO-mediated sequestration of a deep intronic sequence could in fact remodel the 5' ss by disrupting a LDI associated with an RNA structure. While these findings advance our understanding of splicing regulation in SMA, they also signify the enormous potential for uncovering the structure-associated regulatory network of general splicing.

REFERENCES

1. Lin, S. and Fu, X. D. (2007) SR proteins and related factors in alternative splicing. *Adv. Exp. Med. Biol.*, 623, 107-122.
2. Martinez-Contreras, R., Cloutier, P., Shkreta, L., Fisette, J. F., Revil, T. and Chabot, B. (2007) hnRNP proteins and splicing control. *Adv. Exp. Med. Biol.*, 623, 123-147.
3. David, C. J. and Manley, J. L. (2008) The search for alternative splicing regulators: new approaches offer a path to a splicing code. *Genes Dev.*, 22, 279-285.
4. Wang, E. T., Sandberg, R., Luo, S., Khrebtukova, I., Zhang, L., Mayr, C., Kingsmore, S. F., Schroth, G. P. and Burge, C. B. (2008) Alternative isoform regulation in human tissue transcriptomes. *Nature*, 456, 470-476.
5. Yu, Y., Maroney, P. A., Denker, J. A., Zhang, X. H., Dybkov, O., Lührmann, R., Jankowsky, E., Chasin, L. A. and Nilsen, T. W. (2008) Dynamic regulation of alternative splicing by silencers that modulate 5' splice site competition. *Cell*, 135, 1224-1236.
6. Barash, Y., Calarco, J. A., Gao, W., Pan, Q., Wang, X., Shai, O., Blencowe, B. J. and Frey, B. J. (2010) Deciphering the splicing code. *Nature*, 465, 53-59.
7. Buratti, E. and Baralle, F. E. (2004) Influence of RNA secondary structure on the pre-mRNA splicing process. *Mol. Cell. Biol.*, 24, 10505-10514.
8. Graveley, B. R. (2005) Mutually exclusive splicing of the insect Dscam pre-mRNA directed by competing intronic RNA secondary structures. *Cell*, 123, 65-73.
9. Shepard, P. J. and Hertel, K. J. (2008) Conserved RNA secondary structures promote alternative splicing. *RNA*, 14, 1463-1469.
10. Warf, M. B. and Berglund, J. A. (2010) Role of RNA structure in regulating pre-mRNA splicing. *Trends Biochem. Sci.*, 35, 169-178.
11. Gralla, J. and Crothers, D. M. (1973) Free energy of imperfect nucleic acid helices. II. Small hairpin loops. *J. Mol. Biol.*, 73, 497-511.
12. Pörschke, D. (1974) Model calculations on the kinetics of oligonucleotide double helix coil transitions. Evidence for a fast chain sliding reaction. *Biophys. Chem.*, 2, 83-96.
13. Darzacq, X., Shav-Tal, Y., de Turris, V., Brody, Y., Shenoy, S. M., Phair, R. D. and Singer, R. H. (2007) In vivo dynamics of RNA polymerase II transcription. *Nat. Struct. Mol. Biol.*, 14, 796-806.
14. Donahue, C. P., Muratore, C., Wu, J. Y., Kosik, K. S. and Wolfe, M. S. (2006) Stabilization of the tau exon 10 stem loop alters pre-mRNA splicing. *J. Biol. Chem.*, 281, 23302-23306.
15. Buratti, E., Dhir, A., Lewandowska, M. A. and Baralle, F. E. (2007) RNA structure is a key regulatory element in pathological ATM and CFTR pseudoexon inclusion events. *Nucleic Acids Res.*, 35, 4369-4383.
16. Singh, N. N., Singh, R. N. and Androphy, E. J. (2007) Modulating role of RNA structure in alternative splicing of a critical exon in the spinal muscular atrophy genes. *Nucleic Acids Res.*, 35, 371-389.
17. Warf, M. B., Diegel, J. V., von Hippel, P. H. and Berglund, J. A. (2009) The protein factors MBNL1 and U2AF65 bind alternative RNA structures to regulate splicing. *Proc. Natl. Acad. Sci. USA*, 106, 9203-9208.
18. Shen, M., Bellaousov, S., Hiller, M., de La Grange, P., Creamer, T. P., Malina, O., Sperling, R., Mathews, D. H., Stoilov, P. and Stamm, S. (2013) Pyrvinium pamoate changes alternative splicing of the serotonin receptor 2C by influencing its RNA structure. *Nucleic Acids Res.*, 41, 3819-3832.
19. Raker, V. A., Mironov, A. A., Gelfand, M. S. and Pervouchine, D. D. (2009) Modulation of alternative splicing by long-range RNA structures in Drosophila. *Nucleic Acids Res.*, 37, 4533-4544.
20. Pervouchine, D. D., Khrameeva, E. E., Pichugina, M. Y., Nikolaienko, O. V., Gelfand, M. S., Rubtsov, P. M. and Mironov, A. A. (2012) Evidence for widespread association of mammalian splicing and conserved long-range RNA structures. *RNA*, 18, 1-15.
21. Lefebvre, S., Bürglen, L., Reboullet, S., Clermont, O., Burlet, P., Viollet, L., Benichou, B., Cruaud, C., Millasseau, P. and Zeviani, M. (1995) Identification and characterization of a spinal muscular atrophy-determining gene. *Cell*, 80, 155-165.
22. Vitte, J., Fassier, C., Tiziano, F. D., Dalard, C., Soave, S., Roblot, N., Brahe, C., Saugier-Veber, P., Bonnefont, J. P. and Melki, J. (2007) Refined characterization of the expression and stability of the SMN gene products. *Am. J. Pathol.*, 171, 1269-1280.
23. Cho, S. and Dreyfuss, G. (2010) A degron created by SMN2 exon 7 skipping is a principal contributor to spinal muscular atrophy severity. *Genes Dev.*, 24, 438-442.
24. Wirth, B., Brichta, L. and Hahnen, E. (2006) Spinal muscular atrophy and therapeutic prospects. *Prog. Mol. Subcell. Biol.*, 44, 109-132.
25. Lorson, C. L., Hahnen, E., Androphy, E. J. and Wirth, B. (1999) A single nucleotide in the SMN gene regulates splicing and is responsible for spinal muscular atrophy. *Proc. Natl. Acad. Sci. USA*, 96, 6307-6311.
26. Cartegni, L. and Krainer, A. R. (2002) Disruption of an SF2/ASF-dependent exonic splicing enhancer in SMN2 causes spinal muscular atrophy in the absence of SMN1. *Nat. Genet.*, 30, 377-384.
27. Kashima, T. and Manley, J. L. (2003) A negative element in SMN2 exon 7 inhibits splicing in spinal muscular atrophy. *Nat. Genet.*, 34, 460-463.
28. Kashima, T., Rao, N. and Manley, J. L. (2007) An intronic element contributes to splicing repression in spinal muscular atrophy. *Proc. Natl. Acad. Sci. USA*, 104, 3426-3431.
29. Baughan, T. D., Dickson, A., Osman, E. Y. and Lorson, C. L. (2009) Delivery of bifunctional RNAs that target an intronic repressor and increase SMN levels in an animal model of spinal muscular atrophy. *Hum. Mol. Genet.*, 18, 1600-1611.
30. Pedrotti, S., Bielli, P., Paronetto, M. P., Ciccosanti, F., Fimia, G. M., Stamm, S., Manley, J. L. and Sette, C. (2010) The splicing regulator Sam68 binds to a novel exonic splicing silencer and functions in SMN2 alternative splicing in spinal muscular atrophy. *EMBO J.*, 29, 1235-1247.
31. Singh, N. N., Seo, J., Ottesen, E. W., Shishimorova, M., Bhattacharya, D. and Singh, R. N. (2011) TIA1 prevents skipping of a critical exon associated with spinal muscular atrophy. *Mol. Cell. Biol.,* 31, 935-954.
32. Singh, N. N. and Singh, R. N. (2011) Alternative splicing in spinal muscular atrophy underscores the role of an intron definition model. *RNA Biol.,* 8, 600-606.
33. Singh, N. N., Androphy, E. J. and Singh, R. N. (2004) In vivo selection reveals combinatorial controls that define a critical exon in the spinal muscular atrophy genes. *RNA,* 10, 1291-1305.
34. Singh, N. K., Singh, N. N., Androphy, E. J. and Singh, R. N. (2006) Splicing of a critical exon of human Survival Motor Neuron is regulated by a unique silencer element located in the last intron. *Mol. Cell. Biol.,* 26, 1333-1346.
35. Singh, N. N., Shishimorova, M., Cao, L. C., Gangwani, L. and Singh, R. N. (2009) A short antisense oligonucleotide masking a unique intronic motif prevents skipping of a critical exon in spinal muscular atrophy. *RNA Biol.,* 6, 341-350.
36. Hua, Y., Sahashi, K., Rigo, F., Hung, G., Horev, G., Bennett, C. F. and Krainer, A. R. (2011) Peripheral SMN restoration is essential for long-term rescue of a severe spinal muscular atrophy mouse model. *Nature,* 478, 123-126.
37. Porensky, P. N., Mitrpant, C., McGovern, V. L., Bevan, A. K., Foust, K. D., Kaspar, B. K., Wilton, S. D. and Burghes, A. H. (2012) A single administration of morpholino antisense oligomer rescues spinal muscular atrophy in mouse. *Hum. Mol. Genet.,* 21, 1625-1638.
38. Zhou, H., Janghra, N., Mitrpant, C., Dickinson, R. L., Anthony, K., Price, L., Eperon, I. C., Wilton, S. D., Morgan, J. and Muntoni, F. (2013) A novel morpholino oligomer targeting ISS-N1 improves rescue of severe spinal muscular atrophy transgenic mice. *Hum. Gene Ther.,* 24, 331-342.
39. Sivanesan, S., Howell, M. D., DiDonato, C. J. and Singh, R. N. (2013) Antisense oligonucleotide mediated therapy of spinal muscular atrophy. *Transl. Neurosci.* 4: 1-7.
40. Singh, N. N., Hollinger, K., Bhattacharya, D. and Singh, R. N. (2010) An antisense microwalk reveals critical role of an intronic position linked to a unique long-distance interaction in pre-mRNA splicing. *RNA,* 16, 1167-1181.
41. Singh, N. N., Seo, J., Rahn, S. J. and Singh, R. N. (2012) A multi-exon-skipping detection assay reveals surprising diversity of splice isoforms of spinal muscular atrophy genes. *PLoS One,* 7, e49595.
42. Wilkinson, K. A., Merino, E. J. and Weeks, K. M. (2006) Selective 2'-hydroxyl acylation analyzed by primer extension (SHAPE): quantitative RNA structure analysis at single nucleotide resolution. *Nat. Protoc.,* 1, 1610-1616.
43. Mortimer, S. A. and Weeks, K. M. (2007) A fast-acting reagent for accurate analysis of RNA secondary and tertiary structure by SHAPE chemistry. *J. Am. Chem. Soc.,* 129, 4144-4145.
44. Zuker, M. (2003) Mfold web server for nucleic acid folding and hybridization prediction. *Nucleic Acids Res.,* 31, 3406-3415.
45. Wilkinson, K. A., Vasa, S. M., Deigan, K. E., Mortimer, S. A., Giddings, M. C. and Weeks, K. M. (2009) Influence of nucleotide identity on ribose 2'-hydroxyl reactivity in RNA. *RNA,* 15, 1314-1321.
46. Deigan, K. E., Li, T. W., Mathews, D. H. and Weeks, K. M. (2009) Accurate SHAPE-directed RNA structure determination. *Proc. Natl. Acad. Sci. USA,* 106, 97-102.
47. Michlewski, G., Guil, S. and Cáceres, J. F. (2010) Stimulation of pri-miR-18a processing by hnRNP A1. *Adv. Exp. Med. Biol.,* 700, 28-35.
48. Hua, Y., Vickers, T. A., Okunola, H. L., Bennett, C. F. and Krainer, A. R. (2008) Antisense masking of an hnRNP A1/A2 intronic splicing silencer corrects SMN2 splicing in transgenic mice *Am. J. Hum. Genet.,* 82, 834-848.
49. Lescoute, A. and Westhof, E. (2006) The interaction networks of structured RNAs. *Nucleic Acids Res.,* 34, 6587-6604.
50. Chauhan, S. and Woodson, S. A. (2008) Tertiary interactions determine the accuracy of RNA folding. *J. Am. Chem. Soc.,* 130, 1296-1303.
51. de la Peña, M., Dufour, D. and Gallego, J. (2009) Three-way RNA junctions with remote tertiary contacts: a recurrent and highly versatile fold. *RNA,* 15, 1949-1964.
52. Klar, J., Sobol, M., Melberg, A., Mäbert, K., Ameur, A., Johansson, A. C., Feuk, L., Entesarian, M., Orlén, H., Casar-Borota, O. et al. (2013) Welander distal myopathy caused by an ancient founder mutation in TIA1 associated with perturbed splicing. *Hum. Mutat.,* 34, 572-577.
53. Lamichhane, R., Daubner, G. M., Thomas-Crusells, J., Auweter, S. D., Manatschal, C., Austin, K. S., Valniuk, O., Allain, F. H. and Rueda, D. (2010) RNA looping by PTB: Evidence using FRET and NMR spectroscopy for a role in splicing repression. *Proc. Natl. Acad. Sci. USA,* 107, 4105-4110.
54. Laurent, F. X., Sureau, A., Klein, A. F., Trouslard, F., Gasnier, E., Furling, D. and Marie, J. (2012) New function for the RNA helicase p68/DDX5 as a modifier of MBNL1 activity on expanded CUG repeats. *Nucleic Acids Res.,* 40, 3159-3171.
55. Dardenne, E., Pierredon, S., Driouch, K., Gratadou, L., Lacroix-Triki, M., Espinoza, M. P., Zonta, E., Germann, S., Mortada, H., Villemin, J. P. et al. (2012) Splicing switch of an epigenetic regulator by RNA helicases promotes tumor-cell invasiveness. *Nat. Struct. Mol. Biol.,* 19, 1139-1146.
56. Förch, P., Puig, O., Martinez, C., Séraphin, B. and Valcárcel, J. (2002) The splicing regulator TIA-1 interacts with U1-C to promote U1 snRNP recruitment to 5' splice sites. *EMBO J.,* 21, 6882-6892.
57. Kolb, S. J., Battle, D. J. and Dreyfuss, G. (2007) Molecular functions of the SMN complex. *J. Child Neurol.,* 22, 990-994.
58. Fallini, C., Zhang, H., Su, Y., Silani, V., Singer, R. H., Rossoll, W. and Bassell, G. J. (2011) The survival of motor neuron (SMN) protein interacts with the mRNA-binding protein HuD and regulates localization of poly(A) mRNA in primary motor neuron axons. *J. Neurosci.,* 31, 3914-3925.
59. Cirak, S., Arechavala-Gomeza, V., Guglieri, M., Feng, L., Torelli, S., Anthony, K., Abbs, S., Garralda, M. E., Bourke, J., Wells, D. J. et al. (2011) Exon skipping and dystrophin restoration in patients with Duchenne muscular dystrophy after systemic phosphorodiamidate morpholino oligomer treatment: an open-label, phase 2, dose-escalation study. *Lancet,* 378, 595-605.
60. Aznarez, I., Barash, Y., Shai, O., He, D., Zielenski, J., Tsui, L. C., Parkinson, J., Frey, B. J., Rommens, J. M. and Blencowe, B. J. (2008) A systematic analysis of intronic sequences downstream of 5' splice sites reveals a widespread role for U-rich motifs and TIA1/TIAL1 proteins in alternative splicing regulation. *Genome Res.,* 18, 1247-1258.
61. Ankö, M. L. and Neugebauer, K. M. (2012) RNA-protein interactions in vivo: global gets specific. *Trends Biochem. Sci.,* 37, 255-262.

62. Mills, J. D. and Janitz, M. (2012) Alternative splicing of mRNA in the molecular pathology of neurodegenerative diseases. *Neurobiol. Aging,* 33, 1012.e1011-1024.
63. Gregory, T. R. (2005) Synergy between sequence and size in large-scale genomics. *Nat. Rev. Genet.,* 6, 699-708.
64. Wan, Y., Qu, K., Ouyang, Z., Kertesz, M., Li, J., Tibshirani, R., Makino, D. L., Nutter, R. C., Segal, E. and Chang, H. Y. (2012) Genome-wide measurement of RNA folding energies. *Mol. Cell,* 48, 169-181.

Tables

TABLE 1

Abbreviations used in this study

| Abbreviation | Full Name | Applicable Figure(s) |
|---|---|---|
| 1M7 | 1-methyl-7-nitroisatoic anhydride | NA |
| $^{10}$C | Cytosine residue at the 10$^{th}$ position of SMN intron 7 | NA |
| A100G | An adenosine to guanosine substitution at the 100$^{th}$ position of SMN2 intron 7 | 1 |
| ASO | Antisense oligonucleotide | NA |
| C6U | A cytosine to uridine substitution at the 6$^{th}$ position of SMN2 exon 7 | 1 |
| Ex | Exon | NA |
| Exinct | Extended inhibitory context | 1 |
| GC-rich | Sequence from the 7$^{th}$ to 14$^{th}$ positions of SMN intron 7 | 1 |
| hnRNP | Hetero-nuclear ribonucleoprotein | 1,16 |
| ISS-N1 | Intronic splicing silencer N1 | 1, 2,4,16 |
| ISS-N2 | Intronic splicing silencer N2 | 1,11,16 |
| ISTL1 | Internal stem through LDI 1 | 1,4-9,11,12,16 |
| ISTL1-M4 | Four substitutions that strengthen ISTL1 | 5,7,8,14 |
| ISTL2 | Internal stem through LDI 2 | 1,6,11,12,16 |
| ISTL3 | Internal stem through LDI 3 | 1,6,11,12,16 |
| LDI | Long distance interaction | 1 |
| LS-1 | LDI Site 1 | 1,4-6,11,16 |
| nt | Nucleotide | NA |
| RTase | Reverse transcriptase | |
| SHAPE | Selective 2'-Hydroxyl Acylation analyzed by Primer Extension | NA |
| SMA | Spinal muscular atrophy | NA |
| SMN (Italics) | Survival motor neuron gene or transcript | NA |
| SMN | Survival motor neuron protein | NA |
| TIA1 | T-cell intracellular antigen-1 | NA |
| TSL2 | Terminal stem-loop 2 | 6,12 |
| TSL3 | Terminal stem-loop 3 | 6,16 |
| TSL4 | Terminal stem-loop 4 | 6,16 |
| TSL5 | Terminal stem-loop 5 | 6,16 |
| TSL6 | Terminal stem-loop 6 | 6,16 |
| TSL7 | Terminal stem-loop 7 | 6,16 |
| U1 snRNP | U1 small nuclear ribonucleoprotein | 12 |
| URC1 | U-rich cluster 1 | 1,16 |
| URC2 | U-rich cluster 2 | 1,16 |
| URC3 | U-rich cluster 3 | 1,16 |

TABLE 2

Sequences of antisense oligonucleotides

| No. | Name | Sequence (5' to 3') |
|---|---|---|
| 1 | Anti-N1[#] | A*mU*mU*mC*mA*mC*mU*mU*mU*mC*mA*mU*mA*mA*mU*mG*mC*mU*mG*mG (SEQ ID NO: 15) |
| 2 | F14[#] | mU*mU*mU*mC*mA*mU*mA*mA*mU*mG*mC*mU*mG* mG (SEQ ID NO: 11) |
| 3 | L14[#] | mC*mU*mU*mU*mC*mA*mU*mA*mA*mU*mG*mC*mU* mG (SEQ ID NO: 10) |
| 4 | Control (10-mer)[#] | mU*mU*mG*mC*mC*mU*mU*mU*mC*mU (SEQ ID NO: 16) |
| 5 | ASO 261-278[#] | mC*mU*mA*mG*mU*mG*mA*mU*mA*mU*mA*mA*mA* mA*mU*mG*mG*mC (SEQ ID NO: 1) |
| 6 | ASO 271-285[#] | mC*mU*mG*mC*mC*mU*mA*mC*mU*mU*mA*mG*mU*mG* mA*mU (SEQ ID NO: 2) |
| 7 | ASO 276-290[#] | mC*mU*mG*mG*mU*mC*mU*mG*mC*mC*mU*mA*mC* mU*mA (SEQ ID NO: 3) |
| 8 | ASO 281-295[#] | mG*mU*mC*mU*mG*mC*mU*mG*mG*mU*mC*mU*mG* mC*mC (SEQ ID NO: 5) |
| 9 | ASO 283-297[#] | mA*mA*mG*mU*mC*mU*mG*mC*mU*mG*mG*mU*mC* mU*mG (SEQ ID NO: 6) |
| 10 | ASO 286-300[#] | mA*mA*mA*mA*mA*mG*mU*mC*mU*mG*mC*mU*mG* mG*mU (SEQ ID NO: 7) |
| 11 | ASO 290-307[#] | mC*mA*mA*mU*mA*mA*mA*mA*mA*mA*mA*mA*mG* mU*mC*mU*mG*mC (SEQ ID NO: 8) |
| 12 | ASO 301-318[#] | mA*mU*mC*mC*mC*mA*mU*mU*mA*mU*mC*mA*mC*mA* mA*mU*mA*mA*mA (SEQ ID NO: 17) |

TABLE 2-continued

Sequences of antisense oligonucleotides

| No. | Name | Sequence (5' to 3') |
|---|---|---|
| 13 | ASO-M[#] | mA*mA*mG*mU*mC*mU*mG*mC*mC*mA*mG*mC*mC*mU*mG*mC*mC*mU*mA*mC*mU*mA*mG (SEQ ID NO: 18) |
| 14 | ASO-D[¶] | ATTCACTTTCATAATGCTGGCAGACTTAC (SEQ ID NO: 19) |

[#]These are RNA ASOs synthesized by Dharmacon/ThermoScientific Molecular Biology. Letter m represents O-methyl modification at the $2^{nd}$ position of a sugar residue and a star
*represents phosphorothioate modification of the backbone.
[¶]DNA oligonucleotide

TABLE 3

Sequences of primers used for RT-PCR

| No. | Name | Annealing position | Sequence (5' to 3') |
|---|---|---|---|
| 1 | N-24 | SMN Exon 6 | CCAGATTCTCTTGATGATGCTGAT GCTTTGGG (SEQ ID NO: 20) |
| 2 | P1 | Vector-specific | CGACTCACTATAGGCTAGCC (SEQ ID NO: 21) |
| 3 | P2 | SMN Exon 8 | GCATGCAAGCTTCCTTTTTTCTTT CCCAACAC (SEQ ID NO: 22) |
| 4 | P25 | SMN Exon 8 | CTCGAAGCGGCCGCAGCTCATAAA ATTACCA (SEQ ID NO: 23) |
| 5 | P31 | SMN Exon 6 | CATGAGTGGCTATCATACTG (SEQ ID NO: 24) |

TABLE 4

Sequences of primers used for RTase extensions in SHAPE structure probing

| No. | Name | Annealing position within SMN2 intron 7 | Sequence (5' to 3') |
|---|---|---|---|
| 1 | Primer #51 | 51-81 | AATGTTCAAAAACATTTGTTTTCCACAAACC (SEQ ID NO: 25) |
| 2 | Primer#10 | 88-112 | CCTTTCAACTTTCTAACATCTGAAC (SEQ ID NO: 26) |
| 3 | Primer#107 | 107-138 | CTTTAATATTGATTGTTTTACATTAACCTTTC (SEQ ID NO: 27) |
| 4 | Primer#181 | 181-206 | AGTTAAGTATGAGAATTCTAGTAGGG (SEQ ID NO: 28) |
| 5 | Primer#211 | 211-237 | GTGAAAGTATGTTTCTTCCACACAACC (SEQ ID NO: 29) |
| 6 | Primer#252 | 252-281 | CTACTAGTGATATAAAATGGCATCATATCC (SEQ ID NO: 30) |
| 7 | Primer#315 | 315-340 | TACAGTGCAGTATGCCTAGGTTATCC (SEQ ID NO: 31) |
| 8 | Primer#17 | 338-362 | GAGCACTTCATATGTCAGAGTGTAC (SEQ ID NO: 32) |
| 9 | Primer#3L | 411-436 | GAGAAATTAGAACCAGAGGCTTGACG (SEQ ID NO: 33) |
| 10 | Primer#414 | 414-442 | GCAAATGAGAAATTAGAACCAGAGGCTTG (SEQ ID NO: 34) |

Example 2

Microwalk with Morpholino Antisense Oligonucleotides Against ISS-N2

Applicants concluded an ASO microwalk using 21 (twenty one) morpholino ASOs targeting ISS-N2 in SMA patient cells (GM 03813). They employed RT-PCR as an assay to determine the splicing-correction efficacy of ISS-N2 targeting ASOs as described earlier (Singh et al., 2013). Sarepta Therapeutics synthesized all morpholino ASOs utilized in this study. The purpose of antisense microwalk was to determine the optimum ASO size and its target site (ASO annealing position) within ISS-N2. Location of ISS-N2 within SMN2 intron 7 and annealing positions of the morpholino ASOs used in this study are shown in FIG. 18. Initial screening was performed using a broad range of ASO concentrations starting from 0.3 µM to 24 µM. Even at the highest concentrations of 24 µM morpholino ASOs, we did not observe any adverse effect on cell survival and cell growth.

The screening identified three lead morpholino ASOs: SMA-759 (20-mer) (SEQ ID NO:4), SMA-657 (18-mer) (SEQ ID NO:41) and SMA-719 (15-mer) (SEQ ID NO:5) (FIG. 19). All three ASOs sequestered LS-1 and caused a concentration dependent increase in SMN2 exon 7 inclusion in experiments carried out independently with three batches of patient cells (FIG. 20). Of note, LS-1 is the core motif for inhibitory long-distance interaction that we have recently reported (Singh et al., 2013). One of the common features among lead ASOs was the identical 3' end that sequestered GGC residues spanning from the $281^{st}$ to $283^{rd}$ positions of intron 7 (FIG. 18). Due to an additional hydrogen bond formed in G:C base pair as compared to A:U base pair, we reason that GGC sequence within ISS-N2 stabilizes the duplex formed between each of the lead ASO and their intronic target. All three lead ASOs had variable 5' ends and sequestered different lengths of sequences downstream of LS-1. SMA-759, a 20-mer ASO was the longest ASO and sequestered five uridine residues downstream of LS-1. These results confirm ISS-N2 as a valid novel target for a morpholino ASO-based therapy of SMA. Considering recent pre-clinical studies support a better tolerance for morpholino ASOs when directly injected into brain of SMA mice (Sivanesan et al., 2013; Seo et al., 2013), our results hold a high promise for SMA therapy.

FIG. 18 is a schematic representation of antisense target (ISS-N2) within SMN2 intron 7. Role of ISS-N2 on SMN2 exon 7 splicing has been recently described (Singh et al., 2013). Numbering starts from the first position of intron 7. Horizontal bars of various colors represent ASOs. Horizontal bars in dark red colors represent the most effective ISS-N2-targeting ASOs in promoting SMN2 exon 7 inclusion. GCC sequence and LS-1 are highlighted.

FIG. 19 shows the effect of morpholino ASOs on splicing of SMN2 exon 7 in SMA patient cells. ASOs were delivered into SMA type I patient fibroblasts (GM 03813) using Nucleofector technology, and the effect on splicing of exon 7 was tested ~24 hours later by RT-PCR using total RNA prepared from nucleofected cells. Effect of a given ASO on SMN2 exon 7 splicing was compared with the mock (water) nucleofected sample. Skipping of SMN2 exon 7 in water-transfected sample was considered as 100%. SMA-759 (ASO 281-300), SMA-657 (ASO 281-297) and SMA-719 (ASO 281-295) emerged as three lead ISS-N2-targeting morpholino ASOs. A control ASO (SMA-090) with scrambled sequence produced a negligible effect on SMN2 exon 7 splicing at all concentrations tested.

FIG. 20 shows the effect of lead morpholino ASOs on splicing of SMN2 exon 7 in SMA patient cells. Experiments were performed similarly as in FIG. 2, except effect of ASOs on SMN2 exon 7 splicing was determined ~48 hours post nucleofection. Bars represent an average of three independent experiments performed for each ASO concentration. All three ISS-N2-targeting lead ASOs (SMA-657, SMA-759 and SMA-719) showed substantial inclusion of SMN2 exon 7 at 1 μM concentration. A control ASO (SMA-090) with scrambled sequence produced a negligible effect on SMN2 exon 7 splicing at all concentrations tested.

(Sequences with prefix In7 are linear sequence motifs that start and finish at designated positions within SMN intron 7. Sequences with prefix ASO are antisense oligonucleotides, which anneal to specific motifs that start and finish at designated positions within SMN intron 7. Abbreviation of specific sequences or ASOs are shown in brackets)

REFERENCES

Seo J, Howell M D, Singh N N and Singh R N (2013). Spinal muscular atrophy: An update on therapeutic progress. Biochim Biophys Acta 1832, 2180-2190.

Singh N N, Lawler M N, Ottesen E W, Upreti D, Kaczynski J R and Singh R N (2013). An intronic structure enabled by a long-distance interaction serves as a novel target for splicing correction in spinal muscular atrophy. Nucleic Acids Research 41, 8144-8165.

Sivanesan S, Howell M D, DiDonato C J and Singh R N (2013). Antisense oligonucleotide mediated therapy of spinal muscular atrophy. Translational Neuroscience 4, 1-7.

| | | |
|---|---|---|
| In7-3-10 | GUCUGCC | |
| ASO-261-278 | CUAGUGAUAUAAAAUGGC | SEQ ID NO: 1 |
| ASO-271-285 | CUGCCUACUAGUGAU | SEQ ID NO: 2 |
| ASO-276-290 | CUGGUCUGCCUACUA | SEQ ID NO: 3 |
| ASO-281-300 (795) | AAAAAGUCUGCUGGUCUGCC | SEQ ID NO: 4 |
| ASO-281-295 (719) | GUCUGCUGGUCUGCC | SEQ ID NO: 5 |
| ASO-283-297 (523) | AAGUCUGCUGGUCUG | SEQ ID NO: 6 |
| ASO-286-300 | AAAAAGUCUGCUGGU | SEQ ID NO: 7 |
| ASO-290-307 | CAAUAAAAAAAGUCUGC | SEQ ID NO: 8 |
| ASO-299-316 | AUCCCAUAUCACAAUAAA | SEQ ID NO: 9 |
| ASO-10-23 (L14) | CUUUCAUAAUGCUG | SEQ ID NO: 10 |
| ASO-11-24 (F14) | UUUCAUAAUGCUGG | SEQ ID NO: 11 |
| In7-290-295 (LS-1) | GCAGAC | |
| In7-275-297 (ISS-N2) (517) | CUAGUAGGCAGACCAGCAGACUU | SEQ ID NO: 12 |
| In7-290-297 (3'ISTL1) | -GCAGACUU | |
| In7-283-289 (3'ISTL2) | CAGACCA | |
| In7-275-282 (3'ISTL3) | CUAGUAGG | |

-continued

Figure 1B:
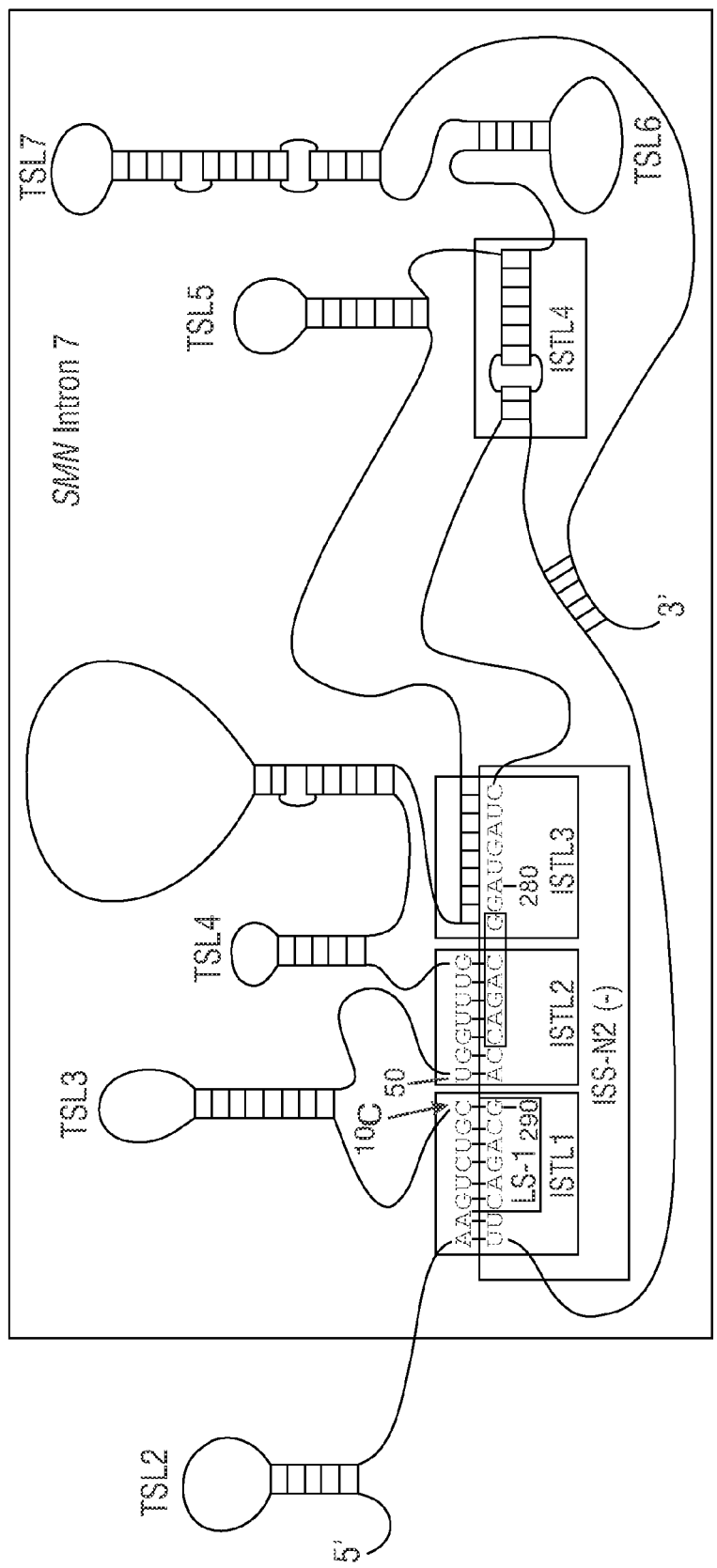

| Name | Sequence | SEQ ID |
|---|---|---|
| ASO-ISTL | AAGUCUGCUGGUCUGCCUACUAG | SEQ ID NO: 13 |
| Intron 7 (entire sequence) FIG. 1b | | SEQ ID NO: 14 |
| Anti-N1 | AUUCACUUUCAUAAUGCUGG | SEQ ID NO15 |
| Control (10-mer) | UUGCCUUUCU | SEQ ID NO: 16 |
| ASO 301-318m | AUCCCAUAUCACAAUAAA | SEQ ID NO: 17 |
| ASO-M | AAGUCUGCCAGCCUGCCUACUAG | SEQ ID NO: 18 |
| ASO-D¶ | ATTCACTTTCATAATGCTGGCAGACTTAC | SEQ ID NO: 19 |
| N-24 | CCAGATTCTCTTGATGATGCTGATGCTTTGGG | SEQ ID NO: 20 |
| P1 | CGACTCACTATAGGCTAGCC | SEQ ID NO: 21 |
| P2 | GCATGCAAGCTTCCTTTTTTCTTTCCCAACAC | SEQ ID NO: 22 |
| P25 | CTCGAAGCGGCCGCAGCTCATAAAATTACCA | SEQ ID NO: 23 |
| P31 | CATGAGTGGCTATCATACTG | SEQ ID NO: 24 |
| Primer #51 | AATGTTCAAAAACATTTGTTTTCCACAAACC | SEQ ID NO: 25 |
| Primer#10 | CCTTTCAACTTTCTAACATCTGAAC | SEQ ID NO: 26 |
| Primer#107 | CTTTAATATTGATTGTTTTACATTAACCTTTC | SEQ ID NO: 27 |
| Primer#181 | AGTTAAGTATGAGAATTCTAGTAGGG | SEQ ID NO: 28 |
| Primer#211 | GTGAAAGTATGTTTCTTCCACACAACC | SEQ ID NO: 29 |
| Primer#252 | CTACTAGTGATATAAAATGGCATCATATCC | SEQ ID NO: 30 |
| Primer#315 | TACAGTGCAGTATGCCTAGGTTATCC | SEQ ID NO: 31 |
| Primer#17 | GAGCACTTCATATGTCAGAGTGTAC | SEQ ID NO: 32 |
| Primer#3L | GAGAAATTAGAACCAGAGGCTTGACG | SEQ ID NO: 33 |
| Primer#414 | GCAAATGAGAAATTAGAACCAGAGGCTTG | SEQ ID NO: 34 |
| ISS-N1 | CCAGCAUUAUGAAAG | SEQ ID NO: 35 |
| 871 | CUAGUAGGCAGACCAGCAGACUU | SEQ ID NO: 36 |
| 745 | UAGUAGGCAGACCAGCAGACUU | SEQ ID NO: 37 |
| 748 | AGUAGGCAGACCAGCAGACUU | SEQ ID NO: 38 |
| 043 | GUAGGCAGACCAGCAGACUU | SEQ ID NO: 39 |
| 524 | UAGGCAGACCAGCAGACUU | SEQ ID NO: 40 |
| 657 | AGGCAGACCAGCAGACUU | SEQ ID NO: 41 |
| 177 | GGCAGACCAGCAGACUU | SEQ ID NO: 42 |
| 235 | CUAGUAGGCAGACCAGCAGACUUUUU | SEQ ID NO: 43 |
| 288 | AGUAGGCAGACCAGCAGACUUUUU | SEQ ID NO: 44 |
| 002 | UAGGCAGACCAGCAGACUUUUU | SEQ ID NO: 45 |
| 885 | GGCAGACCAGCAGACUUUUU | SEQ ID NO: 46 |
| 578 | CAGACCAGCAGACUUUUU | SEQ ID NO: 47 |
| 172 | CCAGCAGACUUUUU | SEQ ID NO: 48 |
| 568 | AUCACUAGUAGGCAGACCAGCAGAC | SEQ ID NO: 49 |
| 774 | UAGUAGGCAGACCAGCAGAC | SEQ ID NO: 50 |
| 684 | AUCACUAGUAGGCAGACCAG | SEQ ID NO: 51 |

```
                                              -continued
5'T7-Xba-2             ATA TAT TCT AGA TAA TAC GAC TCA CTA        SEQ ID NO: 52
                       TAG GGA TTC CTT AAA TTA AGG AGT AAG TC 3'Hind-2               ATA TAT AAG CTT TTC TGC AAA TGA GAA        SEQ ID NO: 53
                       ATT AGA ACC AG
```

The contents of any patents, patent applications, and references cited throughout this specification are hereby incorporated by reference in their entireties.

Those skilled in the art will recognize, or be able to ascertain using no more than routine experimentation, many equivalents to the specific embodiments of the invention described herein. Such equivalents are intended to be encompassed by the following claims.

What is claimed is:

1. An antisense oligonucleotide analog of 15 to 40 nucleotides in length comprising: a nucleotide sequence which is complementary to and which targets nucleotides 275-300 of intron 7 (SEQ ID NO:14) of the Survival Motor Neuron 2 (SMN2) gene, wherein the antisense oligonucleotide analog is modified by the substitution of at least one nucleotide with a modified nucleotide, such that in vivo stability is enhanced as compared to a corresponding unmodified antisense oligonucleotide analog.

2. The antisense oligonucleotide analog of claim 1 having at least 5 nucleotides complementary to nucleotides 5' or 3' to nucleotides 290-295 of intron 7 (SEQ ID NO:14) of the Survival Motor Neuron 2 (SMN2) gene.

3. The antisense oligonucleotide analog of claim 1 comprising a sequence complementary to the sequence 5'-GCAGAC-3'.

4. The antisense oligonucleotide analog of claim 1, comprising a sequence selected from the group consisting of SEQ ID NOS: 1, 4, 5, 6, 7, 8, 9, or 13, or a sequence complementary to SEQ ID NOS: 36, 37, 38, 39, 40, 41, 42, 43, 44, 45, 46, 47, 48, 49, 50, or 51.

5. The antisense oligonucleotide analog of claim 1, comprising a sequence selected from the group consisting of SEQ ID NOS: 4, 5, 6, 7, 8, 9, or 13, or a sequence complementary to SEQ ID NO: 41.

6. The antisense oligonucleotide analog of claim 1, comprising a sequence selected from the group consisting of SEQ ID NOS: 5, 6, 7, 8, or 9, or a sequence complementary to SEQ ID NO: 41 wherein uracil bases are optionally thymine bases.

7. The antisense oligonucleotide analog of claim 1, comprising SEQ ID NO: 6, wherein uracil bases are optionally thymine bases.

8. The antisense oligonucleotide analog of claim 1, comprising SEQ ID NO: 4, wherein uracil bases are optionally thymine bases.

9. The antisense oligonucleotide analog of claim 1, comprising a sequence complementary to SEQ ID NO: 41, wherein uracil bases are optionally thymine bases.

10. The antisense oligonucleotide analog of claim 9 comprising a nucleotide sequence which is 20-25 nucleotides in length.

11. The antisense oligonucleotide analog of claim 1, comprising SEQ ID NO: 5, wherein uracil bases are optionally thymine bases.

12. The antisense oligonucleotide analog of claim 8 comprising a nucleotide sequence which is 20-25 nucleotides in length.

13. The antisense oligonucleotide analog of claim 1, comprising a nucleotide sequence which is complementary to and which targets nucleotides 283-297 of intron 7 (SEQ ID NO:14) of the Survival Motor Neuron 2 (SMN2) gene.

14. The antisense oligonucleotide analog of claim 1, comprising a nucleotide sequence which is complementary to and which targets nucleotides 281-295 of intron 7 (SEQ ID NO:14) of the Survival Motor Neuron 2 (SMN2) gene.

15. The antisense oligonucleotide analog of claim 1, comprising the sequence of SEQ ID NO:13, wherein uracil bases are optionally thymine bases.

16. The antisense oligonucleotide analog of claim 1, comprising at least 15 contiguous nucleotides of SEQ ID NO:13.

17. The antisense oligonucleotide analog of claim 1, comprising at least 10 contiguous nucleotides of SEQ ID NO: 6.

18. The antisense oligonucleotide analog of claim 1, comprising at least 10 contiguous nucleotides of SEQ ID NO:5.

19. The antisense oligonucleotide analog of claim 1, said antisense oligonucleotide analog having a sequence of SEQ ID NO:13.

20. The antisense oligonucleotide analog of claim 1, said antisense oligonucleotide analog comprising a sequence greater than 80% identical to SEQ ID NO:13.

21. The antisense oligonucleotide analog of claim 1, wherein the modified nucleotide is a sugar-modified nucleotide.

22. The antisense oligonucleotide analog of claim 1, wherein the modified nucleotide is a nucleobase-modified nucleotide.

23. The antisense oligonucleotide analog of claim 1, wherein the modified nucleotide is a 2'-deoxy ribonucleotide.

24. The antisense oligonucleotide analog of claim 23, wherein the 2'-deoxy ribonucleotide is 2'-deoxy adenosine or 2'-deoxy guanosine.

25. The antisense oligonucleotide analog of claim 1, wherein the modified nucleotide is a 2'-O-methyl ribonucleotide.

26. The antisense oligonucleotide analog of claim 1, wherein the modified nucleotide is selected from the group consisting of a 2'-fluoro, 2'-amino and 2'-thio modified ribonucleotide.

27. The antisense oligonucleotide analog of claim 1, wherein the modified nucleotide is selected from the group consisting of 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine and 2'-amino-butyryl-pyrene-uridine.

28. The antisense oligonucleotide analog of claim 1, wherein the modified nucleotide is selected from the group consisting of 5-bromo-uridine, 5-iodo-uridine, 5-methyl-cytidine, ribo-thymidine, 2-aminopurine, 5-fluoro-cytidine, and 5-fluoro-uridine, 2,6-diaminopurine, 4-thio-uridine, and 5-amino-allyl-uridine.

29. The antisense oligonucleotide analog of claim 1, wherein the modified nucleotide is a backbone-modified nucleotide.

30. The antisense oligonucleotide analog of claim 29, wherein the backbone-modified nucleotide contains a phosphorothioate group.

31. The antisense oligonucleotide analog of claim 1, wherein the modified nucleotide is a locked nucleic acid (LNA).

32. The antisense oligonucleotide analog of claim 1 wherein said antisense oligonucleotide analog has an internucleoside linkage containing both a basic nitrogen and an alkyl, aryl, or aralkyl group.

33. The antisense oligonucleotide analog of claim 1 wherein said antisense oligonucleotide analog comprises a morpholino.

34. The antisense oligonucleotide analog of claim 1 wherein said antisense oligonucleotide analog includes at least one nucleotide having a formula:

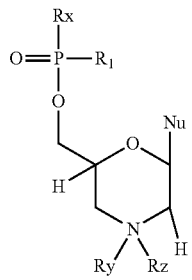

wherein Nu is a nucleobase;
R$_1$ is a moiety of the formula

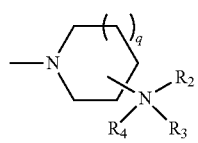

q is 0, 1, 2, 3 or 4;
R$_2$ is selected from the group consisting of hydrogen, C$_1$-C$_5$ alkyl, and a formamidinyl moiety, and
R$_3$ is selected from the group consisting of hydrogen and C$_1$-C$_5$ alkyl, or
R$_2$ and R$_3$ are joined to form a 5-7 membered heterocyclic ring optionally containing an oxygen hetero atom, where the ring may be optionally substituted with a substituent selected from the group consisting of C$_1$-C$_5$ alkyl, phenyl, halogen, and aralkyl;
R$_4$ is selected from the group consisting of null, hydrogen, a C$_1$-C$_6$ alkyl and aralkyl;
Rx is selected from the group consisting of HO—, a nucleotide, a cell penetrating peptide moiety, and piperazinyl;
Ry is selected from the group consisting of hydrogen, a C$_1$-C$_6$ alkyl, a nucleotide, a peptide moiety, an amino acid, a formamidinyl moiety, and acyl; and,
Rz is selected from the group consisting of null, hydrogen, a C$_1$-C$_6$ alkyl, and acyl; and
pharmaceutically acceptable salts thereof.

35. The antisense oligonucleotide analog of claim 34 wherein said nucleobase is selected from the group consisting of adenine, guanine, thymine, uracil, cytosine, and hypoxanthine.

36. The antisense oligonucleotide analog of claim 1 wherein said antisense oligonucleotide analog has at least one nucleoside that has the formula:

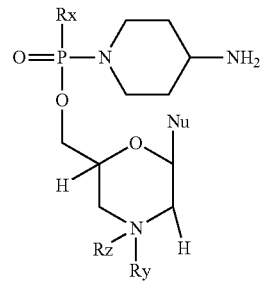

wherein Rx is selected from the group consisting of HO—, a nucleotide, a cell penetrating peptide moiety, and piperazinyl;
Ry is selected from the group consisting of hydrogen, a C$_1$-C$_6$ alkyl, a nucleotide, a peptide moiety, an amino acid, a formamidinyl moiety, and acyl; and,
Rz is selected from the group consisting of null, hydrogen, a CrC6 alkyl, and acyl; and
pharmaceutically acceptable salts thereof.

37. A composition comprising the antisense oligonucleotide analog of claim 1 and a pharmaceutically acceptable carrier.

38. A method of enhancing the level of exon 7-containing Survival Motor Neuron 2 (SMN2) mRNA relative to exon-deleted SMN2 mRNA in a cell or cell extract, comprising contacting the cell or cell extract with the antisense oligonucleotide analog of claim 1, such that the level of exon 7-containing SMN2 mRNA relative to exon-deleted SMN2 mRNA in the cell or cell extract is enhanced.

39. The method of claim 38, wherein the cell or cell extract is a spinal muscular atrophy (SMA) patient-derived neuronal cell, muscle cell or fibroblast, or extract thereof.

40. The method of claim 38, wherein the cell or cell extract is selected from the group consisting of an embryonic stem cell, an embryonic stem cell extract, a neuronal stem cell and a neuronal stem cell extract.

41. A method of enhancing the level of exon 7-containing Survival Motor Neuron 2 (SMN2) mRNA relative to exon-deleted SMN2 mRNA in an organism, comprising administering to the organism the antisense oligonucleotide analog of claim 1, such that the level of exon 7-containing SMN2 mRNA relative to exon-deleted SMN2 mRNA in the organism is enhanced.

42. The method of claim 41, wherein the organism is a mammal.

43. The method of claim 42, wherein the organism is a human.

44. The method of claim 43, wherein the human has spinal muscular atrophy (SMA).

45. A method of treating spinal muscular atrophy (SMA) in a patient, comprising administering to the patient the antisense oligonucleotide analog of claim 1 in a dose effective to enhance the level of exon 7-containing Survival Motor Neuron 2 (SMN2) mRNA relative to exon-deleted SMN2 mRNA in cells of the patient, such that SMA in the patient is treated.

46. A method for inhibiting a Survival Motor Neuron 2 (SMN2) pre-mRNA intronic splicing silencer site in a cell comprising contacting the cell with the antisense oligonucleotide analog of claim 1, such that the SMN2 intronic splicing silencer site is inhibited.

47. A method of enhancing the level of exon 7-containing Survival Motor Neuron 2 (SMN2) mRNA relative to exon-deleted SMN2 mRNA in a cell or cell extract, comprising contacting the cell or cell extract with the antisense oligonucleotide analog of claim 6, such that the level of exon 7-containing SMN2 mRNA relative to exon-deleted SMN2 mRNA in the cell or cell extract is enhanced.

48. The method of claim 47, wherein the cell or cell extract is a spinal muscular atrophy (SMA) patient-derived neuronal cell, muscle cell or fibroblast, or extract thereof.

49. The method of claim 47, wherein the cell or cell extract is selected from the group consisting of an embryonic stem cell, an embryonic stem cell extract, a neuronal stem cell and a neuronal stem cell extract.

50. A method of enhancing the level of exon 7-containing Survival Motor Neuron 2 (SMN2) mRNA relative to exon-deleted SMN2 mRNA in an organism, comprising administering to the organism the antisense oligonucleotide analog of claim 6, such that the level of exon 7-containing SMN2 mRNA relative to exon-deleted SMN2 mRNA in the organism is enhanced.

51. The method of claim 50, wherein the organism is a mammal.

52. The method of claim 51, wherein the organism is a human.

53. The method of claim 52, wherein the human has spinal muscular atrophy (SMA).

54. A method of treating spinal muscular atrophy (SMA) in a patient, comprising administering to the patient the antisense oligonucleotide analog of claim 6 in a dose effective to enhance the level of exon 7-containing Survival Motor Neuron 2 (SMN2) mRNA relative to exon-deleted SMN2 mRNA in cells of the patient, such that SMA in the patient is treated.

55. A method for inhibiting a Survival Motor Neuron 2 (SMN2) pre-mRNA intronic splicing silencer site in a cell comprising contacting the cell with the antisense oligonucleotide analog of claim 6, such that the SMN2 intronic splicing silencer site is inhibited.

56. The antisense oligonucleotide analog of claim 11, wherein the modified nucleotide is a phosphorodiamidate morpholino antisense oligonucleotide analog (PMOs).

57. The antisense oligonucleotide analog of claim 11, wherein the modified nucleotide is a 2'-O-(2-methoxyethyl) antisense oligonucleotide analog (MOE).

58. The antisense oligonucleotide analog of claim 11, wherein the modified nucleotide is a mixed backbone oligonucleotide.

* * * * *

```
                              SEQUENCE LISTING

<160> NUMBER OF SEQ ID NOS: 116

<210> SEQ ID NO 1
<211> LENGTH: 18
<212> TYPE: RNA
<213> ORGANISM: Homo sapiens

<400> SEQUENCE: 1
cuagugauau aaaauggc                                               18

<210> SEQ ID NO 2
<211> LENGTH: 15
<212> TYPE: RNA
<213> ORGANISM: Homo sapiens

<400> SEQUENCE: 2
cugccuacua gugau                                                  15

<210> SEQ ID NO 3
<211> LENGTH: 15
<212> TYPE: RNA
<213> ORGANISM: Homo sapiens

<400> SEQUENCE: 3
cuggucugcc uacua                                                  15

<210> SEQ ID NO 4
<211> LENGTH: 20
<212> TYPE: RNA
<213> ORGANISM: Homo sapiens

<400> SEQUENCE: 4
aaaaagucug cuggucugcc                                             20

<210> SEQ ID NO 5
<211> LENGTH: 15
<212> TYPE: RNA
<213> ORGANISM: Homo sapiens

<400> SEQUENCE: 5
gucugcuggu cugcc                                                  15

<210> SEQ ID NO 6
<211> LENGTH: 15
<212> TYPE: RNA
<213> ORGANISM: Homo sapiens
```

```
<400> SEQUENCE: 6
aagucugcug gucug                                                    15

<210> SEQ ID NO 7
<211> LENGTH: 15
<212> TYPE: RNA
<213> ORGANISM: Homo sapiens

<400> SEQUENCE: 7
aaaaagucug cuggu                                                    15

<210> SEQ ID NO 8
<211> LENGTH: 18
<212> TYPE: RNA
<213> ORGANISM: Homo sapiens

<400> SEQUENCE: 8
caauaaaaaa aagucugc                                                 18

<210> SEQ ID NO 9
<211> LENGTH: 18
<212> TYPE: RNA
<213> ORGANISM: Homo sapiens

<400> SEQUENCE: 9
aucccauauc acaauaaa                                                 18

<210> SEQ ID NO 10
<211> LENGTH: 14
<212> TYPE: RNA
<213> ORGANISM: Homo sapiens

<400> SEQUENCE: 10
cuuucauaau gcug                                                     14

<210> SEQ ID NO 11
<211> LENGTH: 14
<212> TYPE: RNA
<213> ORGANISM: Homo sapiens

<400> SEQUENCE: 11
uuucauaaug cugg                                                     14

<210> SEQ ID NO 12
<211> LENGTH: 23
<212> TYPE: RNA
<213> ORGANISM: Homo sapiens

<400> SEQUENCE: 12
cuaguaggca gaccagcaga cuu                                           23

<210> SEQ ID NO 13
<211> LENGTH: 23
<212> TYPE: RNA
<213> ORGANISM: Homo sapiens

<400> SEQUENCE: 13
aagucugcug gucugccuac uag                                           23

<210> SEQ ID NO 14
<211> LENGTH: 444
<212> TYPE: RNA
<213> ORGANISM: Homo sapiens
```

<400> SEQUENCE: 14

```
guagucugc cagcauuaug aaagugaauc uuacuuuugu aaaacuuuau gguuugugga    60
aaacaaaugu uuuugaacau uuaaaaaguu cagaauguuag aaaguugaaa gguuaaugua  120
aaacaaucaa uauuaaagaa uuuugaugcc aaaacuauua gauaaaaggu uaaucuacau  180
cccuacuaga auucucauac uuaacugguu gguugugugg aagaaacaua cuuucacaau  240
aaagagcuuu aggauaugau gccauuuuau aucacuagua ggcagaccag cagacuuuuu  300
uuuauguga uaugggauaa ccuaggcaua cugcacugua cacucugaca uaugaagugc   360
ucuagucaag uuuaacgguu guccacagag gacaugguuu aacuggaauu cgucaagccu  420
cugguucuaa uuucucauuu gcag                                         444
```

<210> SEQ ID NO 15
<211> LENGTH: 20
<212> TYPE: RNA
<213> ORGANISM: Homo sapiens

<400> SEQUENCE: 15
auucacuuuc auaaugcugg    20

<210> SEQ ID NO 16
<211> LENGTH: 10
<212> TYPE: RNA
<213> ORGANISM: Homo sapiens

<400> SEQUENCE: 16
uugccuuucu    10

<210> SEQ ID NO 17
<211> LENGTH: 18
<212> TYPE: RNA
<213> ORGANISM: Homo sapiens

<400> SEQUENCE: 17
aucccauauc acaauaaa    18

<210> SEQ ID NO 18
<211> LENGTH: 23
<212> TYPE: RNA
<213> ORGANISM: Homo sapiens

<400> SEQUENCE: 18
aagucugcca gccugccuac uag    23

<210> SEQ ID NO 19
<211> LENGTH: 29
<212> TYPE: DNA
<213> ORGANISM: Homo sapiens

<400> SEQUENCE: 19
attcactttc ataatgctgg cagacttac    29

<210> SEQ ID NO 20
<211> LENGTH: 32
<212> TYPE: DNA
<213> ORGANISM: Homo sapiens

<400> SEQUENCE: 20
ccagattctc ttgatgatgc tgatgctttg gg    32

```
<210> SEQ ID NO 21
<211> LENGTH: 20
<212> TYPE: DNA
<213> ORGANISM: Homo sapiens

<400> SEQUENCE: 21
cgactcacta taggctagcc                                              20

<210> SEQ ID NO 22
<211> LENGTH: 32
<212> TYPE: DNA
<213> ORGANISM: Homo sapiens

<400> SEQUENCE: 22
gcatgcaagc ttccttttt ctttcccaac ac                                32

<210> SEQ ID NO 23
<211> LENGTH: 31
<212> TYPE: DNA
<213> ORGANISM: Homo sapiens

<400> SEQUENCE: 23
ctcgaagcgg ccgcagctca taaaattacc a                                 31

<210> SEQ ID NO 24
<211> LENGTH: 20
<212> TYPE: DNA
<213> ORGANISM: Homo sapiens

<400> SEQUENCE: 24
catgagtggc tatcatactg                                              20

<210> SEQ ID NO 25
<211> LENGTH: 31
<212> TYPE: DNA
<213> ORGANISM: Homo sapiens

<400> SEQUENCE: 25
aatgttcaaa aacatttgtt ttccacaaac c                                 31

<210> SEQ ID NO 26
<211> LENGTH: 25
<212> TYPE: DNA
<213> ORGANISM: Homo sapiens

<400> SEQUENCE: 26
cctttcaact ttctaacatc tgaac                                        25

<210> SEQ ID NO 27
<211> LENGTH: 32
<212> TYPE: DNA
<213> ORGANISM: Homo sapiens

<400> SEQUENCE: 27
ctttaatatt gattgtttta cattaacctt tc                                32

<210> SEQ ID NO 28
<211> LENGTH: 26
<212> TYPE: DNA
<213> ORGANISM: Homo sapiens

<400> SEQUENCE: 28
agttaagtat gagaattcta gtaggg                                       26
```

<210> SEQ ID NO 29
<211> LENGTH: 27
<212> TYPE: DNA
<213> ORGANISM: Homo sapiens

<400> SEQUENCE: 29
gtgaaagtat gtttcttcca cacaacc                                27

<210> SEQ ID NO 30
<211> LENGTH: 30
<212> TYPE: DNA
<213> ORGANISM: Homo sapiens

<400> SEQUENCE: 30
ctactagtga tataaaatgg catcatatcc                             30

<210> SEQ ID NO 31
<211> LENGTH: 26
<212> TYPE: DNA
<213> ORGANISM: Homo sapiens

<400> SEQUENCE: 31
tacagtgcag tatgcctagg ttatcc                                 26

<210> SEQ ID NO 32
<211> LENGTH: 25
<212> TYPE: DNA
<213> ORGANISM: Homo sapiens

<400> SEQUENCE: 32
gagcacttca tatgtcagag tgtac                                  25

<210> SEQ ID NO 33
<211> LENGTH: 26
<212> TYPE: DNA
<213> ORGANISM: Homo sapiens

<400> SEQUENCE: 33
gagaaattag aaccagaggc ttgacg                                 26

<210> SEQ ID NO 34
<211> LENGTH: 29
<212> TYPE: DNA
<213> ORGANISM: Homo sapiens

<400> SEQUENCE: 34
gcaaatgaga aattagaacc agaggcttg                              29

<210> SEQ ID NO 35
<211> LENGTH: 15
<212> TYPE: RNA
<213> ORGANISM: Homo sapiens

<400> SEQUENCE: 35
ccagcauuau gaaag                                             15

<210> SEQ ID NO 36
<211> LENGTH: 23
<212> TYPE: RNA
<213> ORGANISM: Homo sapiens

<400> SEQUENCE: 36
cuaguaggca gaccagcaga cuu                                    23

```
<210> SEQ ID NO 37
<211> LENGTH: 22
<212> TYPE: RNA
<213> ORGANISM: Homo sapiens

<400> SEQUENCE: 37
uaguaggcag accagcagac uu                                              22

<210> SEQ ID NO 38
<211> LENGTH: 21
<212> TYPE: RNA
<213> ORGANISM: Homo sapiens

<400> SEQUENCE: 38
aguaggcaga ccagcagacu u                                               21

<210> SEQ ID NO 39
<211> LENGTH: 20
<212> TYPE: RNA
<213> ORGANISM: Homo sapiens

<400> SEQUENCE: 39
guaggcagac cagcagacuu                                                 20

<210> SEQ ID NO 40
<211> LENGTH: 19
<212> TYPE: RNA
<213> ORGANISM: Homo sapiens

<400> SEQUENCE: 40
uaggcagacc agcagacuu                                                  19

<210> SEQ ID NO 41
<211> LENGTH: 18
<212> TYPE: RNA
<213> ORGANISM: Homo sapiens

<400> SEQUENCE: 41
aggcagacca gcagacuu                                                   18

<210> SEQ ID NO 42
<211> LENGTH: 17
<212> TYPE: RNA
<213> ORGANISM: Homo sapiens

<400> SEQUENCE: 42
ggcagaccag cagacuu                                                    17

<210> SEQ ID NO 43
<211> LENGTH: 26
<212> TYPE: RNA
<213> ORGANISM: Homo sapiens

<400> SEQUENCE: 43
cuaguaggca gaccagcaga cuuuuu                                          26

<210> SEQ ID NO 44
<211> LENGTH: 24
<212> TYPE: RNA
<213> ORGANISM: Homo sapiens

<400> SEQUENCE: 44
aguaggcaga ccagcagacu uuuu                                            24
```

```
<210> SEQ ID NO 45
<211> LENGTH: 22
<212> TYPE: RNA
<213> ORGANISM: Homo sapiens

<400> SEQUENCE: 45
uaggcagacc agcagacuuu uu                                              22

<210> SEQ ID NO 46
<211> LENGTH: 20
<212> TYPE: RNA
<213> ORGANISM: Homo sapiens

<400> SEQUENCE: 46
ggcagaccag cagacuuuuu                                                 20

<210> SEQ ID NO 47
<211> LENGTH: 18
<212> TYPE: RNA
<213> ORGANISM: Homo sapiens

<400> SEQUENCE: 47
cagaccagca gacuuuuu                                                   18

<210> SEQ ID NO 48
<211> LENGTH: 14
<212> TYPE: RNA
<213> ORGANISM: Homo sapiens

<400> SEQUENCE: 48
ccagcagacu uuuu                                                       14

<210> SEQ ID NO 49
<211> LENGTH: 25
<212> TYPE: RNA
<213> ORGANISM: Homo sapiens

<400> SEQUENCE: 49
aucacuagua ggcagaccag cagac                                           25

<210> SEQ ID NO 50
<211> LENGTH: 20
<212> TYPE: RNA
<213> ORGANISM: Homo sapiens

<400> SEQUENCE: 50
uaguaggcag accagcagac                                                 20

<210> SEQ ID NO 51
<211> LENGTH: 20
<212> TYPE: RNA
<213> ORGANISM: Homo sapiens

<400> SEQUENCE: 51
aucacuagua ggcagaccag                                                 20

<210> SEQ ID NO 52
<211> LENGTH: 56
<212> TYPE: DNA
<213> ORGANISM: Homo sapiens

<400> SEQUENCE: 52
atatattcta gataatacga ctcactatag ggattcctta aattaaggag taagtc         56
```

```
<210> SEQ ID NO 53
<211> LENGTH: 38
<212> TYPE: DNA
<213> ORGANISM: Homo sapiens

<400> SEQUENCE: 53
atatataagc ttttctgcaa atgagaaatt agaaccag                            38

<210> SEQ ID NO 54
<211> LENGTH: 63
<212> TYPE: RNA
<213> ORGANISM: Homo sapiens

<400> SEQUENCE: 54
caggguuuua gacaaaauca aaagaagga aggugcucac auuccuuaaa uuaaggagua     60
agu                                                                  63

<210> SEQ ID NO 55
<211> LENGTH: 104
<212> TYPE: RNA
<213> ORGANISM: Homo sapiens

<400> SEQUENCE: 55
guaagucugc cagcauuaug aaagugaauc uuacuuuugu aaacuuuau gguuugugga     60 aaacaaaugu uuugaacau uuaaaaaguu cagauguuag aaag                     104

<210> SEQ ID NO 56
<211> LENGTH: 40
<212> TYPE: RNA
<213> ORGANISM: Homo sapiens

<400> SEQUENCE: 56
guaagucugc cagcauuaug aaagugaauc uuacuuuugu                          40

<210> SEQ ID NO 57
<211> LENGTH: 61
<212> TYPE: RNA
<213> ORGANISM: Homo sapiens

<400> SEQUENCE: 57
ugccauuuua uaucacuagu aggcagacca gcagacuuuu uuuuauugug auaugggaua   60
a                                                                    61

<210> SEQ ID NO 58
<211> LENGTH: 51
<212> TYPE: RNA
<213> ORGANISM: Homo sapiens

<400> SEQUENCE: 58
uaucacuagu aggcagacca gcagacuuuu uuuuauugug auaugggaua a             51

<210> SEQ ID NO 59
<211> LENGTH: 51
<212> TYPE: RNA
<213> ORGANISM: Homo sapiens

<400> SEQUENCE: 59
ugccauuagu aggcagacca gcagacuuuu uuuuauugug auaugggaua a             51
```

```
<210> SEQ ID NO 60
<211> LENGTH: 51
<212> TYPE: RNA
<213> ORGANISM: Homo sapiens

<400> SEQUENCE: 60
ugccauuuua uggcagacca gcagacuuuu uuuuauugug auaugggaua a          51

<210> SEQ ID NO 61
<211> LENGTH: 51
<212> TYPE: RNA
<213> ORGANISM: Homo sapiens

<400> SEQUENCE: 61
ugccauuuua uaucacacca gcagacuuuu uuuuauugug auaugggaua a          51

<210> SEQ ID NO 62
<211> LENGTH: 51
<212> TYPE: RNA
<213> ORGANISM: Homo sapiens

<400> SEQUENCE: 62
ugccauuuua uaucacuagu acagacuuuu uuuuauugug auaugggaua a          51

<210> SEQ ID NO 63
<211> LENGTH: 51
<212> TYPE: RNA
<213> ORGANISM: Homo sapiens

<400> SEQUENCE: 63
ugccauuuua uaucacuagu aggcaguuuu uuuuauugug auaugggaua a          51

<210> SEQ ID NO 64
<211> LENGTH: 51
<212> TYPE: RNA
<213> ORGANISM: Homo sapiens

<400> SEQUENCE: 64
ugccauuuua uaucacuagu aggcagacca guuuauugug auaugggaua a          51

<210> SEQ ID NO 65
<211> LENGTH: 51
<212> TYPE: RNA
<213> ORGANISM: Homo sapiens

<400> SEQUENCE: 65
ugccauuuua uaucacuagu aggcagacca gcagacugug auaugggaua a          51

<210> SEQ ID NO 66
<211> LENGTH: 51
<212> TYPE: RNA
<213> ORGANISM: Homo sapiens

<400> SEQUENCE: 66
ugccauuuua uaucacuagu aggcagacca gcagacuuuu uuaugggaua a          51

<210> SEQ ID NO 67
<211> LENGTH: 51
<212> TYPE: RNA
<213> ORGANISM: Homo sapiens

<400> SEQUENCE: 67
ugccauuuua uaucacuagu aggcagacca gcagacuuuu uuuuaugaua a          51
```

```
<210> SEQ ID NO 68
<211> LENGTH: 51
<212> TYPE: RNA
<213> ORGANISM: Homo sapiens

<400> SEQUENCE: 68
ugccauuuua uaucacuagu aggcagacca gcagacuuuu uuuuauugug a          51

<210> SEQ ID NO 69
<211> LENGTH: 29
<212> TYPE: RNA
<213> ORGANISM: Homo sapiens

<400> SEQUENCE: 69
guaggcagac cagcagacuu uuuuuauu                                    29

<210> SEQ ID NO 70
<211> LENGTH: 24
<212> TYPE: RNA
<213> ORGANISM: Homo sapiens

<400> SEQUENCE: 70
cagaccagca gacuuuuuu uauu                                         24

<210> SEQ ID NO 71
<211> LENGTH: 24
<212> TYPE: RNA
<213> ORGANISM: Homo sapiens

<400> SEQUENCE: 71
guaaccagca gacuuuuuu uauu                                         24

<210> SEQ ID NO 72
<211> LENGTH: 24
<212> TYPE: RNA
<213> ORGANISM: Homo sapiens

<400> SEQUENCE: 72
guaggcagca gacuuuuuu uauu                                         24

<210> SEQ ID NO 73
<211> LENGTH: 24
<212> TYPE: RNA
<213> ORGANISM: Homo sapiens

<400> SEQUENCE: 73
guaggcagaa gacuuuuuu uauu                                         24

<210> SEQ ID NO 74
<211> LENGTH: 24
<212> TYPE: RNA
<213> ORGANISM: Homo sapiens

<400> SEQUENCE: 74
guaggcagac cacuuuuuu uauu                                         24

<210> SEQ ID NO 75
<211> LENGTH: 24
<212> TYPE: RNA
<213> ORGANISM: Homo sapiens

<400> SEQUENCE: 75
guaggcagac cagcauuuuu uauu                                        24
```

```
<210> SEQ ID NO 76
<211> LENGTH: 24
<212> TYPE: RNA
<213> ORGANISM: Homo sapiens

<400> SEQUENCE: 76
guaggcagac cagcagacuu uauu                                              24

<210> SEQ ID NO 77
<211> LENGTH: 24
<212> TYPE: RNA
<213> ORGANISM: Homo sapiens

<400> SEQUENCE: 77
guaggcagac cagcagacuu uauu                                              24

<210> SEQ ID NO 78
<211> LENGTH: 24
<212> TYPE: RNA
<213> ORGANISM: Homo sapiens

<400> SEQUENCE: 78
guaggcagac cagcagacuu uuuu                                              24

<210> SEQ ID NO 79
<211> LENGTH: 22
<212> TYPE: RNA
<213> ORGANISM: Homo sapiens

<400> SEQUENCE: 79
aggcagacca gcagacuuuu uu                                                22

<210> SEQ ID NO 80
<211> LENGTH: 19
<212> TYPE: RNA
<213> ORGANISM: Homo sapiens

<400> SEQUENCE: 80
aggcagagca gacuuuuuu                                                    19

<210> SEQ ID NO 81
<211> LENGTH: 19
<212> TYPE: RNA
<213> ORGANISM: Homo sapiens

<400> SEQUENCE: 81
aggcagacca gacuuuuuu                                                    19

<210> SEQ ID NO 82
<211> LENGTH: 19
<212> TYPE: RNA
<213> ORGANISM: Homo sapiens

<400> SEQUENCE: 82
aggcagacca gacuuuuuu                                                    19

<210> SEQ ID NO 83
<211> LENGTH: 19
<212> TYPE: RNA
<213> ORGANISM: Homo sapiens

<400> SEQUENCE: 83
aggcagacca gccuuuuuu                                                    19
```

```
<210> SEQ ID NO 84
<211> LENGTH: 19
<212> TYPE: RNA
<213> ORGANISM: Homo sapiens

<400> SEQUENCE: 84
aggcagacca gcaguuuuu                                                    19

<210> SEQ ID NO 85
<211> LENGTH: 19
<212> TYPE: RNA
<213> ORGANISM: Homo sapiens

<400> SEQUENCE: 85
aggcagacca gcagacuuu                                                    19

<210> SEQ ID NO 86
<211> LENGTH: 25
<212> TYPE: RNA
<213> ORGANISM: Homo sapiens

<400> SEQUENCE: 86
guaagucugc cagcauuaug aaagu                                             25

<210> SEQ ID NO 87
<211> LENGTH: 16
<212> TYPE: RNA
<213> ORGANISM: Homo sapiens

<400> SEQUENCE: 87
gaccagcaga cuuuuu                                                       16

<210> SEQ ID NO 88
<211> LENGTH: 16
<212> TYPE: RNA
<213> ORGANISM: Homo sapiens

<400> SEQUENCE: 88
guaagucugc cagcau                                                       16

<210> SEQ ID NO 89
<211> LENGTH: 18
<212> TYPE: RNA
<213> ORGANISM: Homo sapiens

<400> SEQUENCE: 89
cagacuggca gacuuuuu                                                     18

<210> SEQ ID NO 90
<211> LENGTH: 18
<212> TYPE: RNA
<213> ORGANISM: Homo sapiens

<400> SEQUENCE: 90
caggcuggca gacuuauu                                                     18

<210> SEQ ID NO 91
<211> LENGTH: 18
<212> TYPE: RNA
<213> ORGANISM: Homo sapiens

<400> SEQUENCE: 91
cagacuagca gacuuuuu                                                     18
```

```
<210> SEQ ID NO 92
<211> LENGTH: 18
<212> TYPE: RNA
<213> ORGANISM: Homo sapiens

<400> SEQUENCE: 92
caggccagca gacuuuuu                                                 18

<210> SEQ ID NO 93
<211> LENGTH: 18
<212> TYPE: RNA
<213> ORGANISM: Homo sapiens

<400> SEQUENCE: 93
cagaccggca gacuuuuu                                                 18

<210> SEQ ID NO 94
<211> LENGTH: 18
<212> TYPE: RNA
<213> ORGANISM: Homo sapiens

<400> SEQUENCE: 94
cagaccagca gacuuauu                                                 18

<210> SEQ ID NO 95
<211> LENGTH: 11
<212> TYPE: RNA
<213> ORGANISM: Homo sapiens

<400> SEQUENCE: 95
guaaguccgc c                                                        11

<210> SEQ ID NO 96
<211> LENGTH: 12
<212> TYPE: RNA
<213> ORGANISM: Homo sapiens

<400> SEQUENCE: 96
agcagacuuu uu                                                       12

<210> SEQ ID NO 97
<211> LENGTH: 11
<212> TYPE: RNA
<213> ORGANISM: Homo sapiens

<400> SEQUENCE: 97
guaagucugc c                                                        11

<210> SEQ ID NO 98
<211> LENGTH: 12
<212> TYPE: RNA
<213> ORGANISM: Homo sapiens

<400> SEQUENCE: 98
agcggacuuu uu                                                       12

<210> SEQ ID NO 99
<211> LENGTH: 11
<212> TYPE: RNA
<213> ORGANISM: Homo sapiens

<400> SEQUENCE: 99
guaagucugg                                                          11
```

```
<210> SEQ ID NO 100
<211> LENGTH: 12
<212> TYPE: RNA
<213> ORGANISM: Homo sapiens

<400> SEQUENCE: 100
accagacuuu uu                                                            12

<210> SEQ ID NO 101
<211> LENGTH: 461
<212> TYPE: RNA
<213> ORGANISM: Homo sapiens

<400> SEQUENCE: 101
auuccuuaaa uuaaggagua agucugccag cauuaugaaa gugaaucuua cuuuuguaaa         60
acuuuauggu uguggaaaa caaauguuuu ugaacauuua aaaaguucag auguuagaaa         120
guugaaaggu uaauguaaaa caaucaauau uaaagaauuu ugaugccaaa acauuuagau        180
aaaagguuaa ucuacauccc acuagaauu cucauacuua acugguuggu uguguggaag         240
aaacauacuu ucacaauaaa gagcuuuagg auaugaugcc auuuuauauc acuaguaggc        300
agaccagcag acuuuuuuuu auugugauau gggauaaccu aggcauacug cacuguacac        360
ucugacauau gaagugcucu agucaaguuu aacggguguc cacagaggac augguuuaac        420
uggaauucgu caagccucug guucuaauuu cucauuugca g                           461

<210> SEQ ID NO 102
<211> LENGTH: 89
<212> TYPE: RNA
<213> ORGANISM: Homo sapiens

<400> SEQUENCE: 102
gauguuagaa aguugaaagg uuaauguaaa acaaucaaua uuaaagaauu uugaugccaa         60
aacuauuaga uaaaagguua aucuacauc                                          89

<210> SEQ ID NO 103
<211> LENGTH: 101
<212> TYPE: RNA
<213> ORGANISM: Homo sapiens

<400> SEQUENCE: 103
ccuacuagaa uucucauacu uaacugguug guugugugga agaaacauac uuucacaaua         60
aagagcuuua ggauaugaug ccauuuuaua ucacuaguag g                           101

<210> SEQ ID NO 104
<211> LENGTH: 57
<212> TYPE: RNA
<213> ORGANISM: Homo sapiens

<400> SEQUENCE: 104
aguaagucug ccagcauuau gaaagugaau cuuacuuuug uaaaacuuua ugguuug            57

<210> SEQ ID NO 105
<211> LENGTH: 15
<212> TYPE: RNA
<213> ORGANISM: Homo sapiens

<400> SEQUENCE: 105
aguaagucug ccagc                                                         15
```

```
<210> SEQ ID NO 106
<211> LENGTH: 27
<212> TYPE: RNA
<213> ORGANISM: Homo sapiens

<400> SEQUENCE: 106
acuaguaggc agaccagcag acuuuuu                                        27

<210> SEQ ID NO 107
<211> LENGTH: 27
<212> TYPE: RNA
<213> ORGANISM: Homo sapiens

<400> SEQUENCE: 107
acuaguaggc aggcuggcag acuuauu                                        27

<210> SEQ ID NO 108
<211> LENGTH: 60
<212> TYPE: RNA
<213> ORGANISM: Homo sapiens

<400> SEQUENCE: 108
augccauuuu auaucacuag uaggcagacc agcagacuuu uuuuauugu gauaugggau    60

<210> SEQ ID NO 109
<211> LENGTH: 74
<212> TYPE: RNA
<213> ORGANISM: Homo sapiens

<400> SEQUENCE: 109
auuccuuaaa uuaaggagua agucugccag cauuaugaaa gugaaucuua cuuuuguaaa   60
acuuuauggu uugu                                                     74

<210> SEQ ID NO 110
<211> LENGTH: 15
<212> TYPE: RNA
<213> ORGANISM: Homo sapiens

<400> SEQUENCE: 110
cagaccagca gacuu                                                    15

<210> SEQ ID NO 111
<211> LENGTH: 58
<212> TYPE: RNA
<213> ORGANISM: Homo sapiens

<400> SEQUENCE: 111
auuccuuaaa uuaaggagua agucugccag cauuaugaaa gugaaucuua cuuuugua     58

<210> SEQ ID NO 112
<211> LENGTH: 11
<212> TYPE: RNA
<213> ORGANISM: Homo sapiens

<400> SEQUENCE: 112
uuaugguuug u                                                        11

<210> SEQ ID NO 113
<211> LENGTH: 17
<212> TYPE: RNA
<213> ORGANISM: Homo sapiens
```

```
<400> SEQUENCE: 113
cuaguaggca gaccauu                                                    17

<210> SEQ ID NO 114
<211> LENGTH: 17
<212> TYPE: RNA
<213> ORGANISM: Homo sapiens

<400> SEQUENCE: 114
cuaguagcag cagacuu                                                    17

<210> SEQ ID NO 115
<211> LENGTH: 59
<212> TYPE: RNA
<213> ORGANISM: Homo sapiens

<400> SEQUENCE: 115
augccauuuu auaucacuag uaggcagacc agcagacuuu uuuuuauugu gauauggga      59

<210> SEQ ID NO 116
<211> LENGTH: 37
<212> TYPE: RNA
<213> ORGANISM: Homo sapiens

<400> SEQUENCE: 116
uaucauauca cuaguaggca gaccagcaga cuuuuuu                              37
```